US007879888B2

(12) United States Patent
Quattropani et al.

(10) Patent No.: US 7,879,888 B2
(45) Date of Patent: Feb. 1, 2011

(54) THIAZOLE DERIVATIVES AND USE THEREOF

(75) Inventors: Anna Quattropani, Geneva (CH); David Covini, Neydens (FR); Vincent Pomel, Groisy (FR); Jerome Dorbais, Annecy (FR); Thomas Rueckle, Geneva (CH)

(73) Assignee: Merck Serono SA, Coinsins, Vaud (CH)

( * ) Notice: Subject to any disclaimer, the term of this patent is extended or adjusted under 35 U.S.C. 154(b) by 394 days.

(21) Appl. No.: 11/915,521

(22) PCT Filed: May 24, 2006

(86) PCT No.: PCT/EP2006/062592

§ 371 (c)(1),
(2), (4) Date: Nov. 26, 2007

(87) PCT Pub. No.: WO2006/125803

PCT Pub. Date: Nov. 30, 2006

(65) Prior Publication Data

US 2008/0221180 A1    Sep. 11, 2008

Related U.S. Application Data

(60) Provisional application No. 60/686,266, filed on Jun. 1, 2005.

(30) Foreign Application Priority Data

May 24, 2005    (EP)    ................... 05104418

(51) Int. Cl.
*A61K 31/426*    (2006.01)
*A61K 31/5377*    (2006.01)
*C07D 277/20*    (2006.01)
*C07D 413/14*    (2006.01)

(52) U.S. Cl. ................ 514/370; 548/146; 548/190; 548/194; 546/184; 546/192; 546/209; 544/106; 544/111; 544/133; 514/365; 514/326; 514/235.5

(58) Field of Classification Search ................ 548/146, 548/190, 193, 194; 514/315, 317, 326, 365, 514/370, 371; 546/184, 192, 209; 544/106, 544/111, 133
See application file for complete search history.

(56) References Cited

U.S. PATENT DOCUMENTS

| 6,586,423 | B2 | 7/2003 | Bilodeau et al. |
| 6,586,424 | B2 | 7/2003 | Bilodeau et al. |
| 7,163,952 | B2 | 1/2007 | Inaba et al. |
| 2003/0158199 | A1 | 8/2003 | Stieber et al. |
| 2008/0188531 | A1 | 8/2008 | Quattropani et al. |
| 2008/0200463 | A1 | 8/2008 | Quattropani et al. |

| 2009/0029997 | A1 | 1/2009 | Quattropani et al. |

FOREIGN PATENT DOCUMENTS

| EP | 0 117 082 | 8/1984 |
| WO | WO 00/75120 | 12/2000 |
| WO | WO 01/17995 | 3/2001 |
| WO | WO 03/072557 | 9/2003 |
| WO | WO 2004/033439 | 4/2004 |
| WO | WO 2004/052286 | 6/2004 |
| WO | WO 2004/078754 | 9/2004 |
| WO | WO 2004/096797 | 11/2004 |
| WO | WO 2005/021519 | 3/2005 |
| WO | WO 2005/047273 | 5/2005 |
| WO | WO 2005/068444 | 7/2005 |
| WO | WO 2006/051270 | 5/2006 |

OTHER PUBLICATIONS

Beaton, C. M. et al. "Some Derivatives of 2- and 3-Phenylthiophen" *J. Chem. Soc.*, 1976, pp. 2355-2563, vol. I.
Bellina, F. et al. "Palladium Catalysts for the Suzuki Cross-Coupling Reaction: An Overview of Recent Advances" *Synthesis*, 2004, pp. 2419-2440, No. 15.
Brummond, K. M. et al. "Solid-Phase Synthesis of BRL 49653" *J. Org. Chem.*, 1999, pp. 1723-1726, vol. 64.
Cantley, L.C. "The Phosphoinositide 3-Kinase Pathway" *Science*, May 31, 2002, pp. 1655-1657, vol. 296.
Fraser, J. D. et al. "Regulation of Interleukin-2 Gene Enhancer Activity by the T Cell Accessory Molecule CD28" *Science*, Jan. 18, 1991, pp. 313-316, vol. 251.
Fruman, D.A. et al. "Phosphoinositide Kinases" *Annu. Rev. Biochem.*, 1998, pp. 481-507, vol. 67.
Gerard, C. et al. "Chemokines and disease" *Nature Immunology*, Feb. 2001, pp. 108-115, vol. 2, No. 2.
Grant, S. "Targeted Therapies in Cancer—Second International Congress" *Current Drugs*, 2003, pp. 946-948, vol. 6, No. 10.
Hirsch, E. et al. "Central Role for G Protein-Coupled Phosphoinositide 3-Kinase γ in Inflammation" *Science*, Feb. 11, 2000, pp. 1049-1053, vol. 287.

(Continued)

*Primary Examiner*—Golam M Shameem
(74) *Attorney, Agent, or Firm*—Saliwanchik, Lloyd & Saliwanchik

(57) ABSTRACT

The present invention is related to thiazole derivatives of Formula (I) in particular for the treatment and/or prophylaxis of autoimmune disorders and/or inflammatory diseases, cardiovascular diseases, neurodegenerative diseases, bacterial or viral infections, kidney diseases, platelet aggregation, cancer, transplantation, graft rejection or lung injuries.

10 Claims, 1 Drawing Sheet

OTHER PUBLICATIONS

Hirsch, E. et al. "Resistance to thromboembolism in PI3Kγ-deficient mice" *FASEB J.*, 2001, pp. 2019-2021, vol. 15, No. 11.

Kodomari, M. et al. "One-pot synthesis of 2-aminothiazoles using supported reagents" *Tetrahedron Letters*, 2002, pp. 1717-1720, vol. 43.

Laffargue, M. et al. "Phosphoninositide 3-Kinase γ Is an Essential Amplifier of Mast Cell Function" *Immunity*, Mar. 2002, pp. 441-451, vol. 16.

Lawlor, M. A. et al. "PKB/Akt: a key mediator of cell proliferation, survival and insulin responses?" *Journal of Cell Science*, 2001, pp. 2903-2910, vol. 114.

Parker, P. J. "PI 3-kinase puts GTP on the Rac" *Current Biology*, 1995, pp. 577-599, vol. 5, No. 6.

Stein, R. C. et al. "PI3-kinase inhibition: a target for drug development?" *Molecular Medicine Today*, Sep. 2000, pp. 347-357, vol. 6.

Thelen, M. et al. "Wortmannin binds specifically to 1-phosphatidylinositol 3-kinase while inhibiting guanine nucleotide-binding protein-coupled receptor signaling in neutrophil leukocytes" *Proc. Natl. Acad. Sci. USA*, May 1994, pp. 4960-4964, vol. 91.

Toker, A. "Phosphoinositides and signal transduction" *Cellular and Molecular Life Sciences*, 2002, pp. 761-779, vol. 59.

Vanhaesebroeck, B. et al. "Phosphoinositide 3-kinases: a conserved family of signal transducers" *Trends Biochem. Science*, Jul. 1997, pp. 267-272, vol. 22.

Vanhaesebroeck, B. et al. "Synthesis and Function of 3-Phosphorylated Inositol Lipids" *Ann. Rev. Biochem.*, 2001, pp. 535-602, vol. 70.

Wymann, M. P. et al. "Lipids on the move: phosphoinositide 3-kinases in leukocyte function" *Immunology Today*, Jun. 2000, pp. 260-264, vol. 21, No. 6.

Yao, R. et al. "Requirement for Phosphatidylinositol-3 Kinase in the Prevention of Apoptosis by Nerve Growth Factor" *Science*, Mar. 31, 1995, pp. 2003-2005, vol. 267.

Guarna, A. et al. "Synthesis and Reactivity of Bicycles Derived from Tartaric Acid and α-Amino Acids: A Novel Class of Conformationally Constrained Dipeptide Isosteres Based upon Enantiopure 3-Aza-6, 8-dioxabicyclo [3.2.1] octane-7-carboxylic Acid" *J. Org. Chem.*, 1999, pp. 7347-7364, vol. 64.

Herr, R. J. et al. "A Convenient Method for the Preparation of Primary and Symmetrical N,N'-Disubstituted Thioureas" *Synthesis*, 2000, pp. 1569-1574, No. 11.

Pirrung, M.C. et al. "Trityl Isothiocyanate Support for Solid-Phase Synthesis" *J. Comb. Chem.*, 2001, pp. 90-96, vol. 3.

Sawhney, S. N. et al. "Thiazole Derivatives: Part I—Synthesis & Anti-Inflammatory Activity of some 2'-Alkyl/Aryl-2-Aryl-4-Methyl-4'5-Bithiazolyls & 2'Amino/Substituted Amino-2-Aryl-4-Methyl-4'5-Bithiazolyls" *Indian Journal of Chemistry*, Jul. 1976, pp. 552-555, vol. 14B, No. 7.

Sayed, S.M. et al. "Synthesis and Reactivity of Cyanomethyl 2-Amino-4-methylthiazolyl Ketone. A Facile Synthesis of Novel Pyrazolo [5,1-c] 1,2,4-triazine, 1,2,4-Triazolo [5,1-c] 1, 2,4,-triazine, 1,2,4-Triazino [4,3-a] benzimidazole, Pyridazine-6-imine and 6-Oxopyridazinone Derivatives" *Heteroatom Chemistry*, 1999, pp. 385-390, vol. 10, No. 5.

Wilson, K.J. et al. "Synthesis of Thiophene-2-carboxamidines Containing 2-Amino-thiazoles and their Biological Evaluation as Urokinase Inhibitors" *Bioorganic & Medicinal Chemistry Letters*, 2001, pp. 915-918, vol. 11.

Wittenberger, S.J. et al. "Dialkyltin Oxide Mediated Addition of Trimethylsilyl Azide to Nitriles. A Novel Preparation of 5-Substituted Tetrazoles" *J.Org. Chem.*, 1993, pp. 4139-4141, vol. 58.

Inaba, T. et al., 2002, CAS: 136:177998, pp. 1-4.

Office Action dated Nov. 24, 2009 in U.S. Appl. No. 11/915,476, filed Nov. 26, 2007.

Allowed claims in U.S. Appl. No. 11/915,476, filed Nov. 26, 2007.

Pending claims in U.S. Appl. No. 11/915,508, filed Nov. 26, 2007.

Pending claims in U.S. Appl. No. 12/159,663, filed Jun. 30, 2008.

Office Action dated Mar. 24, 2010 in U.S. Appl. No. 11/915,508, filed Nov. 26, 2007.

STN International HCAPLUS database Accession No. 2001:185751, Bilodeau, M. et al. "Preparation of N-(pyrid-2-yl)-2-thiazolamines as tyrosine kinase inhibitors" 2001, Columbus, OH, pp. 1-3.

STN International HCAPLUS database Accession No. 2005:451371, Bold, G. et al. "Preparation of thiazole and pyrazole derivatives as Flt-3 kinase inhibitors" 2005, Columbus, OH, pp. 1-4.

THIAZOLE DERIVATIVES AND USE THEREOF

CROSS-REFERENCE TO RELATED APPLICATION

This application is the U.S. national stage application of International Patent Application No. PCT/EP2006/062592, filed May 24, 2006, which claims the benefit of U.S. Provisional Patent Application No. 60/686,266, filed Jun. 1, 2005, the disclosures of which are hereby incorporated by reference in their entireties, including all figures, tables and amino acid or nucleic acid sequences.

FIELD OF THE INVENTION

This present invention is related to the use of thiazole derivatives of Formula (I) for the treatment and/or prophylaxis of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, sperm motility, graft rejection or lung injuries. Specifically, the present invention is related to thiazole derivatives for the modulation, notably the inhibition of the activity or function of the phosphoinositide-3-kinases, PI3Ks.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, *Science*, 296, 1655-1657 and Vanhaesebroeck et al., 2001, *Annu. Rev. Biochem.*, 70, 535-602).

The term PI3K is given to a family of lipid kinases which, in mammals, consists of eight identified PI3Ks that are divided into three sub-families according to their structure and their substrate specificity.

Class I group of PI3Ks consists of two sub-groups, Class IA and Class IB.

Class IA consists of an 85 kDa regulatory unit (responsible for protein-protein interactions via the interaction of Src homology 2 (SH2) domain with phosphotyrosine residues of other proteins) and a catalytic sub-unit of 110 kDa. Three catalytic forms (p110α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complexed with a 101-kDa regulatory protein, p101).

Class II PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 1997, *Trends Biochem Sci.*, 22(7), 267-72). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example.

Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)$P_2$), respectively generating three lipid products, namely phosphatidylinositol 3-monophosphate (PI(3)P), phosphatidylinositol 3,4-bisphosphate (PI(3,4)$P_2$) and phosphatidylinositol 3,4,5-trisphosphate (PI(3,4,5)$P_3$ (see Scheme A below).

Scheme A

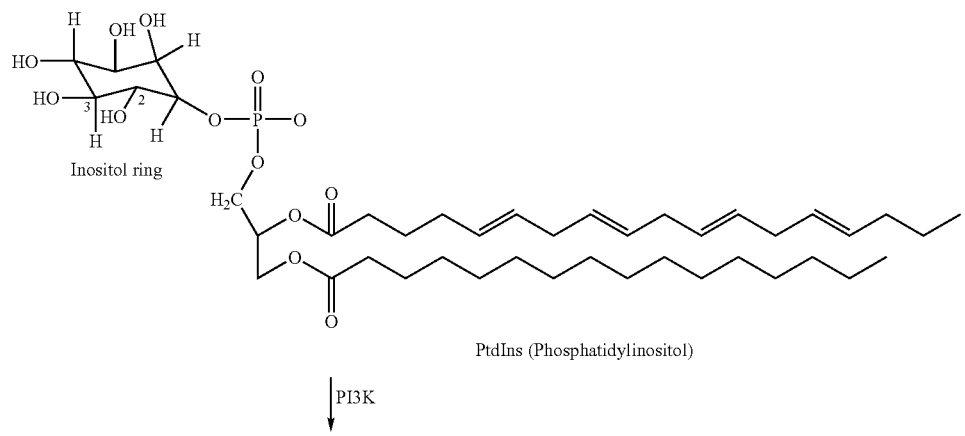

PtdIns (Phosphatidylinositol)

↓ PI3K

-continued

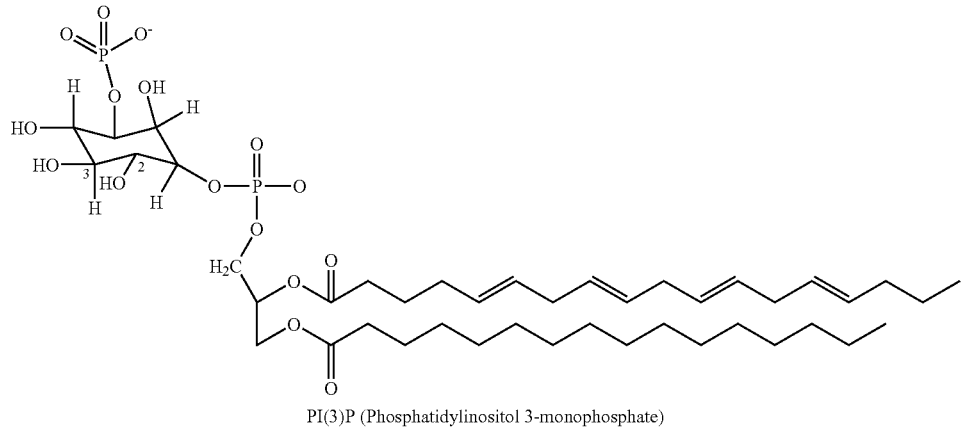

PI(3)P (Phosphatidylinositol 3-monophosphate)

The preferred substrate for Class I PI3Ks is PI(4,5)P$_2$. Class II PIKs have a strong preference for PtdIns as substrate over PI(4)P and PI(4,5)P$_2$. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimerization, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P$_2$ into PI(3,4,5)P$_3$ which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, *Cell Mol. Life Sci.* 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, *Mol. Med. Today* 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, *Immunol Today* 21(6) 260-4; Hirsch et al., 2000, *Science* 287(5455) 1049-53; Hirsch et al., 2001, *FASEB J.* 15(11) 2019-21 and Gerard et al., 2001, *Nat Immunol.* 2(2) 108-15).

PI3-kinase activation, is therefore believed to be involved in a range of cellular responses including cell growth, differentiation and apoptosis (Parker et al., 1995, *Current Biology,* 5, 577-99; Yao et al., 1995, *Science,* 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen. These effects are linked to increases in the transcription of a number of genes including interleukin-2 (IL-2), an important T cell growth factor (Fraser et al., 1991, *Science,* 251, 313-16). Mutation of CD28 such that it can longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3Kγ has been identified as a mediator of G beta-gamma-dependent regulation of JNK activity wherein G beta-gamma are subunits of heterotrimeric G proteins.

Recently, it has been described that PI3Kγ relays inflammatory signals through various G(i)-coupled receptors (Laffargue et al., 2002, *Immunity* 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, *J. Cell. Sci.,* 114 (Pt 16) 2903-1).

Specific inhibitors against individual members of a family of enzymes provide valuable tools for deciphering functions of each enzyme.

Two compounds, LY294002 and wortmannin (cf. hereinafter), have been widely used as PI3-kinase inhibitors. These compounds are non-specific PI3K inhibitors, as they do not distinguish among the four members of Class I PI3-kinases.

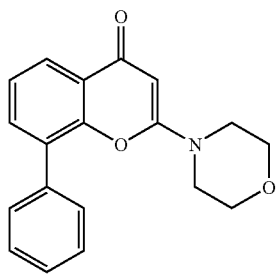
LY 294002

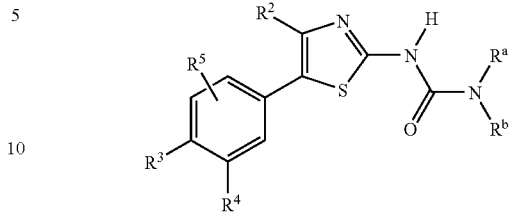

WO 2005/021519 discloses thiazole derivatives of the following structure:

WO 04/078754 discloses thiazole derivatives of the following structure:

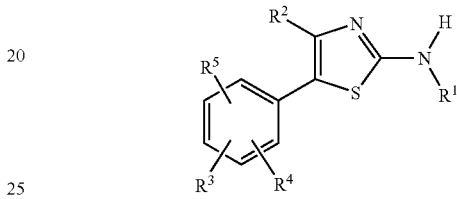

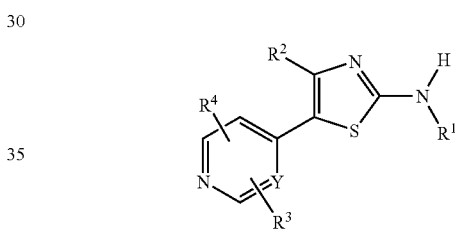

Wortmannin

IC$_{50}$ values of wortmannin against each of the various Class I PI3-kinases are in the range of 1-10 nM and IC$_{50}$ values for LY294002 against each of these PI3-kinases are about 15-20 μM (Fruman et al., 1998, *Ann. Rev. Biochem.*, 67, 481-507), also 5-10 mM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, *Proc. Natl. Acad. Sci. USA*, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using wortmannin, there is evidence that PI3-kinase function is also required for some aspects of leukocyte signaling through G-protein coupled receptors (Thelen et al., 1994). Moreover, it has been shown that wortmannin and LY294002 block neutrophil migration and superoxide release. However, in as much as these compounds do not distinguish among the various isoforms of PI3K, it remains unclear which particular PI3K isoform or isoforms are involved in these phenomena.

Some results have indicated that PI3K inhibitors, for example, LY294002, can increase the in vivo antitumor activity of certain cytotoxic agents (e.g. paclitaxel) (Grant, 2003, *Current Drugs*, 6(10), 946-948).

Recently, thiazole derivatives have been recently developed as PI3K inhibitors (WO 2005/021519; WO 04/078754 and WO 04096797).

WO 04096797 discloses thiazole derivatives of the following structure:

The high relevance of the PI3K pathway in some widely spread diseases stresses the need to develop inhibitors, including selective inhibitors, of PIKs.

SUMMARY OF THE INVENTION

One embodiment of the present invention provides substances which are suitable for the treatment and/or prevention of disorders related to phosphoinositide-3-kinases, PI3Ks.

Another embodiment of the present invention provides substances which are suitable for the treatment and/or prevention of auto-immune and/or inflammatory disorders.

Another embodiment of the present invention provides substances which are suitable for the treatment and/or prevention of cardiovascular diseases.

Another embodiment of the present invention provides substances which are suitable for the treatment and/or prevention of neurodegenerative disorders.

Another embodiment of the present invention provides substances which are suitable for the treatment and/or prevention of a disorder selected from bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

Another embodiment of the present invention provides chemical compounds which are able to modulate, especially inhibit the activity or function of phosphoinositide-3-kinases, PI3Ks in disease states in mammals, especially in humans. In a preferred embodiment the PI3K enzyme is PI3Kinase γ.

Another embodiment of the present invention provides a new category of pharmaceutical formulations for the treatment of and/or diseases mediated selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

Another embodiment of the present invention provides a method for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

In one embodiment, the invention provides thiazole derivatives of Formula (I):

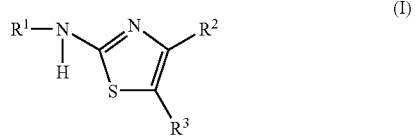

wherein $R^1$, $R^2$ and $R^3$ are defined in the detailed description below.

In another embodiment, the invention provides a compound according to Formula (I) for use as a medicament.

In another embodiment, the invention provides a use of a compound according to Formula (I) for the preparation of a pharmaceutical composition for the treatment of a disorder selected from auto-immune, inflammatory disorders, cardiovascular diseases, neurodegenerative disorders, bacterial and viral infections, allergy, asthma, pancreatitis, multi or; multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks, comprising PI3K α and γ.

In another embodiment, the invention provides a pharmaceutical composition comprising at least one a compound according to Formula (I) and a pharmaceutically acceptable carrier, diluent or excipient thereof.

In another embodiment, the invention provides a method for treating a patient suffering from a disorder selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions and other diseases and disorders associated with the phosphoinositide-3-kinases, PI3Ks. The method comprises administering a compound according to Formula (I).

In another embodiment, the invention provides a method of synthesis of a compound according to Formula (I).

DETAILED DESCRIPTION OF THE INVENTION

Figure 1:
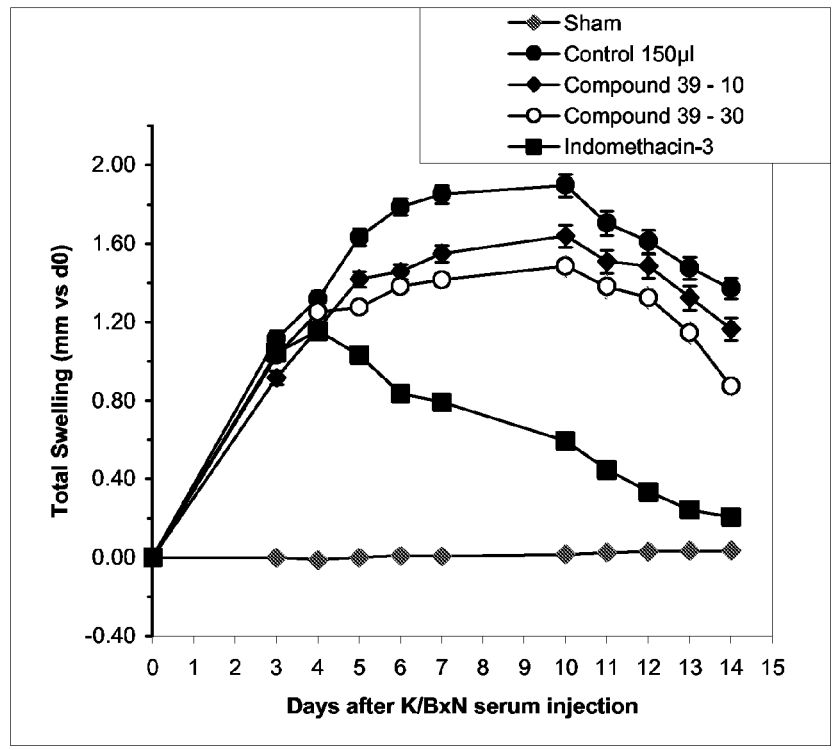
FIG. 1: K/BXN serum transfer model of arthritis after treatment with compound 39.

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups "Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-α]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, N, NR, R being defined as hydrogen or methyl. Heterocycloalkyl include pyrrolidine, piperidine, piperazine, morpholine, tetrahydrofarane, 6,8-dioxa-3-azabicyclo[3.2.1]octane and the like.

"Acyl" refers to the group —C(O)R where R includes H, "$C_1$-$C_{12}$-alkyl", preferably "$C_1$-$C_6$-alkyl", "$C_2$-$C_6$-alkenyl", "$C_2$-$C_6$-alkynyl", "$C_3$-$C_8$-cycloalkyl", "heterocycloalkyl".

"Alkoxy" refers to the group —O—R where R includes "$C_1$-$C_6$-alkyl" or "aryl" or "hetero-aryl".

Preferred alkoxy groups include for example, methoxy, ethoxy, phenoxy and the like.

"Alkoxycarbonyl" refers to the group —C(O)OR where R includes H, "$C_1$-$C_6$-alkyl" or "aryl" or "heteroaryl" or "heteroalkyl".

"Aminocarbonyl" refers to the group —C(O)NRR' where each R, R' includes independently hydrogen or $C_1$-$C_6$-alkyl or aryl or heteroaryl.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl".

"Amino" refers to the group —NRR' where each R,R' is independently hydrogen or "$C_1$-$C_6$-alkyl" or "aryl" or "heteroaryl" or "cycloalkyl", or "heterocycloalkyl", and where R and R', together with the nitrogen atom to which they are attached, can optionally form a 3-8-membered heterocycloalkyl ring.

"Ammonium" refers to a positively charged group —N⁺RR'R", where each R,R',R" is independently "$C_1$-$C_6$-alkyl" or "cycloalkyl", or "heterocycloalkyl", and where R and R', together with the nitrogen atom to which they are attached, can optionally form a 3-8-membered heterocycloalkyl ring.

"Halogen" refers to fluoro, chloro, bromo and iodo atoms.

"Sulfonyl" refers to group "—$SO_2$—R" wherein R is selected from "aryl", "heteroaryl", "$C_1$-$C_6$-alkyl", "$C_1$-$C_6$-alkyl" substituted with halogens, e.g., an —$SO_2$—$CF_3$ group, "$C_1$-$C_6$-alkenyl", "$C_2$-$C_6$-alkynyl", "$C_3$-$C_8$-cycloalkyl", "heterocycloalkyl", "heteroalkyl".

"Sulfinyl" refers to a group "—S(O)—R" wherein R is selected from H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl".

"Sulfanyl" refers to groups —S—R where R includes H, "$C_1$-$C_6$-alkyl", "$C_1$-$C_6$-alkyl" substituted with halogens, e.g., a —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl". Preferred sulfanyl groups include methylsulfanyl, ethylsulfanyl, and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl".

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroary", "heteroalkyl" and where R and R', together with the nitrogen atom to which they are attached, can optionally form a 3-8-membered heterocycloalkyl ring.

"Substituted" refers to groups substituted with from 1 to 5 substituents selected from the group consisting of "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "halogen", "amino", "aminosulfonyl", "ammonium", "aminocarbonyl", "sulfinyl", "sulfanyl", "sulfonyl", hydroxy, "alkoxy", "alkoxycarbonyl", "carbamate", trihalomethyl, cyano, mercapto, nitro, and the like.

"Pharmaceutically acceptable salts or complexes" refers to salts or complexes of the below-identified compounds of Formula (I) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R',R"⁺Z⁻, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism.

It has now been found that compounds according to Formula (I) of the present invention are modulators of the Phosphatoinositides 3-kinases (PI3Ks), comprising PI3K α and γ. When the phosphatoinositides 3-kinase (PI3K) enzyme is inhibited by the compounds of Formula (I), PI3K is unable to exert its enzymatic, biological and/or pharmacological effects.

The compounds of Formula (I) according to the present invention are therefore useful in the treatment and prevention of autoimmune disorders and/or inflammatory diseases, cardiovascular diseases, neurodegenerative diseases, bacterial or viral infections, allergy, asthma, pancreatitis, multi-organ failure, kidney diseases, platelet aggregation, cancer, transplantation, sperm motility, erythrocyte deficiency, graft rejection or lung injuries.

Formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and paratoluenesulfonate salts.

The compounds according to Formula (I) are suitable for the modulation, notably the inhibition of the activity of phosphatoinositides 3-kinases (PI3K). The compounds of the present invention according to Formula (I) are also particularly useful for the treatment and/or prevention of disorders, which are mediated by PI3Ks, particularly PI3K α and/or PI3K γ. Said treatment involves the modulation—notably the inhibition or the down regulation—of the phosphatoinositides 3-kinases.

The compounds according to Formula (I) are suitable for use as a medicament.

In one embodiment, the invention provides thiazole derivatives of Formula (I):

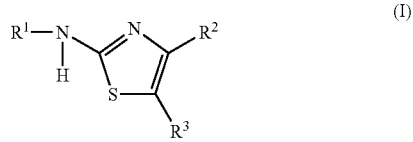

(I)

wherein:
R¹ is selected from H or acyl; optionally a substituted acyl;
R² is a $C_1$-$C_6$-alkyl; optionally a substituted $C_1$-$C_6$-alkyl;
R³ is selected from the following thienyl groups, defined as T1 and T2:

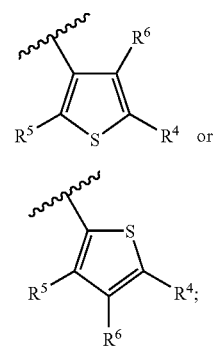

wherein:
R⁴ is selected from
a sulfonyl group $SO_2$—R, wherein R is selected from aryl, heteroaryl, $C_1$-$C_6$-alkyl (e.g. methyl sulfonyl), $C_1$-$C_6$-alkyl substituted with halogens, $C_2$-$C_6$-alkenyl, $C_2$-$C_6$-alkynyl, $C_3$-$C_8$-cycloalkyl, heterocycloalkyl, heteroalkyl; optionally a substituted aryl, heteroaryl, $C_1$-$C_6$-alkyl, $C_2$-$C_6$-alkenyl, $C_2$-$C_6$-alkynyl, $C_3$-$C_8$-cycloalkyl, heterocycloalkyl, such as piperidin (e.g. 3-hydroxypiperidin-1-yl sulfonyl, 4-hydroxypiperidin-1-yl sulfonyl, 4-methoxypiperidin-1-yl sulfonyl, 4-methylaminopiperidin-1-yl sulfonyl, piperidin-4-(tert-butyl methylcarbamate)-yl sulfonyl), morpholin (e.g. morpholin-4-yl sulfonyl), piperazin (e.g. piperazin-1-yl sulfonyl, 4-acetylpiperazin-1-yl sulfonyl, 4-methylpiperazin-1-yl sulfonyl), pyrrolidin (e.g. 3-pyrrolidin-1-yl sulfonyl, 3-hydroxypyrrolidin-1-yl sulfonyl), 6,8-dioxa-3-azabicyclo[3.2.1]oct-3-yl (e.g. 7-(hydroxymethyl)-6,8-dioxa-3-azabicyclo[3.2.1]oct-3-yl), and 8-(1,4-dioxa-8-azaspiro[4.5]decane), heteroalkyl;

an aminosulfonyl group $SO_2$—NRR' wherein each R, R' are independently selected from hydrogen, $C_1$-$C_6$-alkyl, $C_2$-$C_6$-alkenyl (e.g. allylamino sulfonyl), $C_2$-$C_6$-alkynyl (e.g. prop-2-yn-1-ylamino sulfonyl), $C_3$-$C_8$-cycloalkyl, heterocycloalkyl, aryl, heteroaryl, heteroalkyl; optionally a substituted $C_1$-$C_6$-alkyl (e.g. dimethylamino sulfonyl, (2-hydroxyethyl)amino sulfonyl, 2-(methylamino)ethylamino sulfonyl, 2-(dimethylamino)ethylamino sulfonyl, 2-hydroxyethylaminosulfonyl, 2-(acetylamino)ethylamino sulfonyl, 2-(dimethylaminoethyl) methylamino sulfonyl, 2-(dimethylaminoethyl)ethylamino sulfonyl, 2-(diethylaminoethyl) methylamino sulfonyl, 2-(methoxyethyl)methylamino sulfonyl, 3-(dimethylamino) propylamino sulfonyl, 2,3-dihydroxypropylamino sulfonyl, 3-hydroxypropylamino sulfonyl), $C_2$-$C_6$-alkenyl, $C_2$-$C_6$-alkynyl, $C_3$-$C_8$-cycloalkyl, heterocycloalkyl (e.g. 2-morpholin-4-yl-ethylamino sulfonyl, 2-piperidin-1-yl-ethylamino sulfonyl, 1-methyl piperidin-4-ylamino sulfonyl, 4-hydroxycyclohexylamino sulfonyl), aryl, heteroaryl (e.g. 1H-tetrazol-5-ylamino sulfonyl), heteroalkyl, and wherein R and R', together with the nitrogen atom to which they are attached, optionally form a 3-8-membered heterocycloalkyl ring;

R⁵ and R⁶ are independently selected from H, $C_1$-$C_6$-alkyl, $C_2$-$C_6$-alkenyl, $C_2$-$C_6$-alkynyl groups; optionally a substituted $C_1$-$C_6$-alkyl, $C_2$-$C_6$-alkenyl, $C_2$-$C_6$-alkynyl groups and halogen;

as well as its geometrical isomers, its optically active forms as enantiomers, diastereomers and its racemate forms, as well as pharmaceutically acceptable salts thereof.

In a specific embodiment, the invention provides thiazole derivatives of Formula (I) wherein R' is acetyl.

In another specific embodiment, the invention provides thiazole derivatives of Formula (I) wherein R² is methyl.

In another specific embodiment, the invention provides thiazole derivatives of Formula (I) wherein R³ is the thienyl T1.

In another specific embodiment, the invention provides thiazole derivatives of Formula (I) wherein R³ is the thienyl T2.

In another specific embodiment, the invention provides thiazole derivatives of Formula (I) wherein R⁴ is a sulfonyl group $SO_2$—R.

In another specific embodiment, the invention provides thiazole derivatives of Formula (I) wherein R⁴ is an aminosulfonyl group $SO_2$—NRR'.

In another specific embodiment, the invention provides thiazole derivatives of Formula (I) wherein R⁵ and R⁶ are H.

In another preferred embodiment the compounds according to Formula (I) according to the present invention have an IC50 as measured by the PI3K lipid kinase assay of equal or lower than 0.5 µM, preferably 0.05 µM.

Compounds of Formula (I) the present invention include in particular any of the following compounds represented in Table I hereafter:

TABLE I

| Example N° | Name |
|---|---|
| 1 | N-(4-methyl-5-{5-[(prop-2-yn-1-ylamino)sulfonyl]-2-thienyl}-1,3-thiazol-2-yl)acetamide |
| 2 | N-(5-{5-[(4-acetylpiperazin-1-yl)sulfonyl]-2-thienyl}-4-methyl-1,3-thiazol-2-yl)acetamide |
| 3 | N-{5-[5-({[2-(dimethylamino)ethyl]amino}sulfonyl)-2-thienyl]-4-methyl-1,3-thiazol-2-yl}acetamide |

TABLE I-continued

| Example N° | Name |
|---|---|
| 4 | N-[4-methyl-5-(5-{[(1-methylpiperidin-4-yl)amino]sulfonyl}-2-thienyl)-1,3-thiazol-2-yl]acetamide |
| 5 | N-[5-(5-{[[2-(dimethylamino)ethyl](methyl)amino]sulfonyl}-2-thienyl)-4-methyl-1,3-thiazol-2-yl]acetamide |
| 6 | 5-(2-amino-4-methyl-1,3-thiazol-5-yl)-N-(2-morpholin-4-ylethyl)thiophene-2-sulfonamide |
| 7 | methyl 5-{[4-methyl-5-(5-{[(2-morpholin-4-ylethyl)amino]sulfonyl}-2-thienyl)-1,3-thiazol-2-yl]amino}-5-oxopentanoate |
| 8 | N-(4-methyl-5-{5-[(4-methylpiperazin-1-yl)sulfonyl]-2-thienyl}-1,3-thiazol-2-yl)acetamide |
| 9 | N-[4-methyl-5-(5-{[(2-morpholin-4-ylethyl)amino]sulfonyl}-2-thienyl)-1,3-thiazol-2-yl]acetamide |
| 10 | N-{5-[5-({[3-(dimethylamino)propyl]amino}sulfonyl)-2-thienyl]-4-methyl-1,3-thiazol-2-yl}acetamide |
| 11 | N-{4-methyl-5-[5-(piperazin-1-ylsulfonyl)-2-thienyl]-1,3-thiazol-2-yl}acetamide |
| 12 | N~2~-({5-[2-(acetylamino)-4-methyl-1,3-thiazol-5-yl]-2-thienyl}sulfonyl)-N~1~-methylglycinamide |
| 13 | N-{5-[5-({[2-(acetylamino)ethyl]amino}sulfonyl)-2-thienyl]-4-methyl-1,3-thiazol-2-yl}acetamide |
| 14 | N-{5-[5-({[(2,2-dimethyl-1,3-dioxolan-4-yl)methyl]amino}sulfonyl)-2-thienyl]-4-methyl-1,3-thiazol-2-yl}acetamide |
| 15 | methyl N-({5-[2-(acetylamino)-4-methyl-1,3-thiazol-5-yl]-2-thienyl}sulfonyl)serinate |
| 16 | N-({5-[2-(acetylamino)-4-methyl-1,3-thiazol-5-yl]-2-thienyl}sulfonyl)serine |
| 17 | N-[5-(5-{[(2,3-dihydroxypropyl)amino]sulfonyl}-2-thienyl)-4-methyl-1,3-thiazol-2-yl]acetamide |
| 18 | N-(5-{5-[(dimethylamino)sulfonyl]-2-thienyl}-4-methyl-1,3-thiazol-2-yl)acetamide |
| 19 | N-{4-methyl-5-[5-({methyl[2-(methylamino)ethyl]amino}sulfonyl)-2-thienyl]-1,3-thiazol-2-yl}acetamide |
| 20 | N-[5-(5-{[[2-(diethylamino)ethyl](methyl)amino]sulfonyl}-2-thienyl)-4-methyl-1,3-thiazol-2-yl]acetamide |
| 21 | N-[5-(5-{[(2-methoxyethyl)(methyl)amino]sulfonyl}-2-thienyl)-4-methyl-1,3-thiazol-2-yl]acetamide |
| 22 | N-[5-(5-{[[2-(dimethylamino)ethyl](ethyl)amino]sulfonyl}-2-thienyl)-4-methyl-1,3-thiazol-2-yl]acetamide |
| 23 | N-{5-[5-({[2-(dimethylamino)ethyl]amino}sulfonyl)-3-thienyl]-4-methyl-1,3-thiazol-2-yl}acetamide |
| 24 | N-[4-methyl-5-(5-{[(2-morpholin-4-ylethyl)amino]sulfonyl}-3-thienyl)-1,3-thiazol-2-yl]acetamide |
| 25 | N-[4-methyl-5-(5-{[(2-piperidin-1-ylethyl)amino]sulfonyl}-3-thienyl)-1,3-thiazol-2-yl]acetamide |
| 26 | N-{4-methyl-5-[5-(piperazin-1-ylsulfonyl)-3-thienyl]-1,3-thiazol-2-yl}acetamide |
| 27 | N-{5-[5-({[3-(dimethylamino)propyl]amino}sulfonyl)-3-thienyl]-4-methyl-1,3-thiazol-2-yl}acetamide |
| 28 | N-[4-methyl-5-(5-{[(1-methylpiperidin-4-yl)amino]sulfonyl}-3-thienyl)-1,3-thiazol-2-yl]acetamide |
| 29 | N-(4-methyl-5-{5-[(4-methylpiperazin-1-yl)sulfonyl]-3-thienyl}-1,3-thiazol-2-yl)acetamide |
| 30 | tert-butyl [1-({4-[2-(acetylamino)-4-methyl-1,3-thiazol-5-yl]-2-thienyl}sulfonyl)piperidin-4-yl]methylcarbamate |
| 31 | N-(5-{5-[(3-hydroxypyrrolidin-1-yl)sulfonyl]-3-thienyl}-4-methyl-1,3-thiazol-2-yl)acetamide |
| 32 | N-[5-(5-{[(3-hydroxypropyl)amino]sulfonyl}-3-thienyl)-4-methyl-1,3-thiazol-2-yl]acetamide |
| 33 | N-[5-(5-{[(cis-4-hydroxycyclohexyl)amino]sulfonyl}-3-thienyl)-4-methyl-1,3-thiazol-2-yl]acetamide |
| 34 | N-(5-{5-[(4-methoxypiperidin-1-yl)sulfonyl]-3-thienyl}-4-methyl-1,3-thiazol-2-yl)acetamide |
| 35 | N-[4-methyl-5-(5-{[4-(methylamino)piperidin-1-yl]sulfonyl}-3-thienyl)-1,3-thiazol-2-yl]acetamide |
| 36 | N-[5-(5-{[[2-(dimethylamino)ethyl](methyl)amino]sulfonyl}-3-thienyl)-4-methyl-1,3-thiazol-2-yl]acetamide |
| 37 | N-[5-(5-{[(1S,5S,7S)-7-(hydroxymethyl)-6,8-dioxa-3-azabicyclo[3.2.1]oct-3-yl]sulfonyl}-3-thienyl)-4-methyl-1,3-thiazol-2-yl]acetamide |
| 38 | N-[5-(5-{[(2-hydroxyethyl)amino]sulfonyl}-3-thienyl)-4-methyl-1,3-thiazol-2-yl]acetamide |
| 39 | N-(5-{5-[(4-hydroxypiperidin-1-yl)sulfonyl]-3-thienyl}-4-methyl-1,3-thiazol-2-yl)acetamide |
| 40 | N-[5-(5-{[(2,3-dihydroxypropyl)amino]sulfonyl}-3-thienyl)-4-methyl-1,3-thiazol-2-yl]acetamide |
| 41 | N-(4-methyl-5-{5-[(1H-tetrazol-5-ylamino)sulfonyl]-3-thienyl}-1,3-thiazol-2-yl)acetamide |

TABLE I-continued

| Example N° | Name |
|---|---|
| 42 | N-{4-methyl-5-[5-(pyrrolidin-1-ylsulfonyl)-3-thienyl]-1,3-thiazol-2-yl}acetamide |
| 43 | 4-methyl-5-{5-[(4-methylpiperazin-1-yl)sulfonyl]-3-thienyl}-1,3-thiazol-2-amine |
| 44 | methyl 5-[(4-methyl-5-{5-[(4-methylpiperazin-1-yl)sulfonyl]-3-thienyl}-1,3-thiazol-2-yl)amino]-5-oxopentanoate |
| 45 | 1-{[4-(2-amino-4-methyl-1,3-thiazol-5-yl)-2-thienyl]sulfonyl}piperidin-4-ol |
| 46 | N-{4-methyl-5-[5-(morpholin-4-ylsulfonyl)-3-thienyl]-1,3-thiazol-2-yl}acetamide |
| 47 | N-(5-{2-chloro-5-[(4-methylpiperazin-1-yl)sulfonyl]-3-thienyl}-4-methyl-1,3-thiazol-2-yl)acetamide |
| 48 | N-(5-{5-[(3-hydroxypiperidin-1-yl)sulfonyl]-3-thienyl}-4-methyl-1,3-thiazol-2-yl)acetamide |
| 49 | N-(5-{5-[(allylamino)sulfonyl]-3-thienyl}-4-methyl-1,3-thiazol-2-yl)acetamide |

The compounds according to Formula (I) and any of compounds 1 to 49 of Table I of the present invention are useful as medicaments. They may be used for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation, erythrocyte deficiency, graft rejection or lung injuries.

In one embodiment, the compounds of Formula (I) are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another embodiment, the compounds of Formula (I) are useful for the treatment and/or prophylaxis of neurodegenerative diseases including Alzheimer's disease, Huntington's disease, CNS trauma, stroke or ischemic conditions.

In still a further embodiment according to the invention, the compounds of Formula (I) are useful for the treatment and/or prophylaxis of cardiovascular diseases such as atherosclerosis, heart hypertrophy, cardiac myocyte dysfunction, elevated blood pressure or vasoconstriction.

In still a further embodiment according to the invention, the compounds of Formula (I) are useful for the treatment and/or prophylaxis of erythrocyte deficiency such as an anaemia, including haemolytic anaemia, aplastic anaemia and pure red cell anaemia.

In still another embodiment according to the invention, the compounds of Formula (I) are useful for the treatment and/or prophylaxis of chronic obstructive pulmonary disease, anaphylactic shock, fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastisis, in particular melanoma, Karposi's sarcoma, acute and chronic bacterial and viral infections, sepsis, transplantation, graft rejection, glomerulo sclerosis, glomerulo nephritis, progressive renal fibrosis, endothelial and epithelial injuries in the lung or in general lung airways inflammation.

In another embodiment according to the invention, is provided a process for the preparation of thiazole derivative according to Formula (I), comprising the step of reacting a compound of Formula (P1) with a derivative of Formula (P2) in presence of palladium complexes, such as Pd(PPh$_3$)$_4$, [1,1'-bis(diphenylphosphino)ferrocene]palladium(II) chloride (Pd(dppf) Cl$_2$), PdCl$_2$(PPh$_3$)$_2$, Pd(OAc)$_2$ and a base:

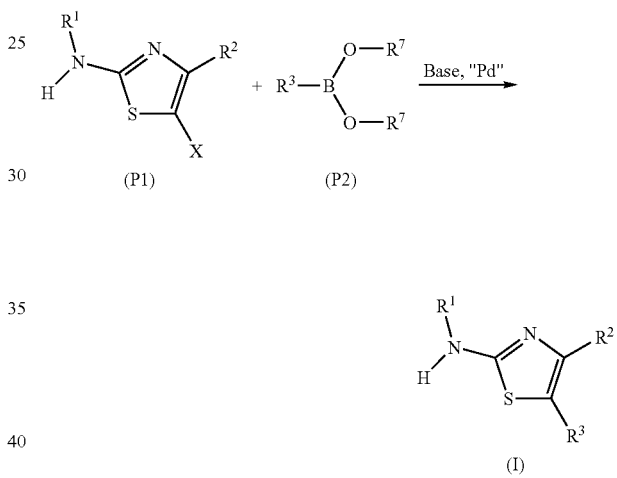

wherein X may be Br or I, R' may be H, for boronic acid derivatives, or any $C_1$-$C_6$ alkyl or substituted $C_1$-$C_6$ alkyl groups for boronic ester derivatives and wherein the group —B(OR$^7$)$_2$ can optionally form a heterocycle such as boronic acid pinacol ester.

In another embodiment according to the invention, is provided a process for the preparation of thiazole derivative according to Formula (I), comprising the step of reacting a compound of Formula (P1) with a tin derivative of Formula (P3) in presence of palladium complexes, such as Pd(PPh$_3$)$_4$, [1,1'-bis(diphenylphosphino)ferrocene]palladium(II) chloride (Pd(dppf) Cl$_2$), PdCl$_2$(PPh$_3$)$_2$, Pd(OAc)$_2$:

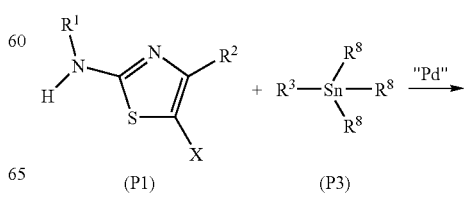

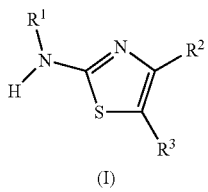

wherein X may be Br or I and $R^8$ is methyl or n-butyl.

The thiazole derivatives according to Formula (I) exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds according to Formula (I) are typically administered in the form of a pharmaceutical composition. Hence, pharmaceutical compositions comprising a compound of Formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds according to Formula (I), together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed Pharmaceutical compositions containing thiazole derivatives of Formula (I) can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, pre-measured ampoules or syringes of the liquid compositions or pills, tablets, capsules or the like in the case of solid compositions. In such compositions, the thiazole derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the thiazole derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences, 20th* Edition, 2000, Marck Publishing Company, Easton, Pa., which is incorporated herein by reference.

The compounds according to Formula (I) of this invention can also be administered in sustained release forms or from sustained release drug delivery systems. A description of representative sustained release materials can also be found in the incorporated materials in *Remington's Pharma-ceutical Sciences*.

Synthesis of Compounds According to Formula (I):

The novel thiazole derivatives according to Formula (I) can be prepared from readily available starting materials by several synthetic approaches, using both solution-phase and solid-phase chemistry protocols (Brummond et al., 1999, *J.O.C.*, 64, 1723-1726). Examples of synthetic pathways for the will be described.

The following abbreviations refer respectively to the definitions below:

Å (Angström), cm (centimeter), eq (equivalent), h (hour), g (gram), M (molar), MHz (Megahertz), µl (microliter), min (minute), mg (milligram), ml (milliliter), mm (millimeter), mmol (millimole), mM (millimolar), nm (nanometer), rt (room temperature), BSA (Bovine Serum Albumin), CDI (N,N'-carbonyldiimidazole), CMC (Carboxymethyl Cellulose), DCC (dicyclohexyl carbodiimide), DCM (dichloromethane), DIEA (diisopropyl ethylamine), DMF (dimethyl formamide), DMSO (Dimethyl Sulfoxide), EDC (1-(3-dimethylaminopropyl)-3-ethyl-carbo diimidehydro-chloride), HOBt (1-hydroxybenzo triazole), HPLC (High Performance Liquid Chromatography), IHC (immunohistochemistry), Ins1P (D-myo-inositol-1-phosphate), LC (Liquid chromatography), MS (mass spectrometry), NBS (N-bromo succinimide), NIS (N-iodo succinimide), NMR (Nuclear Magnetic Resonance), PBS (Phosphate Buffered Saline), $Pd(dppf)Cl_2$ ([1,1'-bis(diphenylphosphino) ferrocene]palladium(II) chloride complex), PIs (Phosphoinositides), PI3Ks (Phosphoinositide 3-kinases), PI(3)P (Phosphatidylinositol 3-monophosphate), PI(3,4)$P_2$ (Phosphatidylinositol 3,4-bisphosphate), PI(3,4,5)$P_3$ (Phosphatidylinositol 3,4,5-trisphosphate), PI(4)P (Phosphatidylinositol-4-phosphate), PI(4,5)$P_2$) (Phosphatidyl inositol-4,5-biphosphate), PtdIns (Phosphatidylinositol), PyBOP (Benzotriazol-1-yloxy) tripyrrolidino-phosphonium hexafluorophosphate), SPA (Scintillation Proximity Assay), TEA (triethylamine), TFA (trifluoroacetic acid), THF (tetrahydrofuran), TLC (Thin Layer Chromatography), UV (Ultraviolet).

The thiazole derivatives 1 to 49 (see Table I) exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In the process illustrated in the following schemes $R^1$, $R^2$, $R^3$, $R^4$, $R^5$ and $R^6$ as above-defined in the description.

Generally, the thiazole derivatives according to the general Formula (I) could be obtained by several synthetic approaches, using both solution-phase and solid-phase chemistry protocols (Kodomari et al., 2002, *Tetrahedron Lett.*, 43, 1717-1720) either by conventional methods or by microwave-assisted techniques.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

Methods of Preparing Intermediates of Compounds of Formula (I).

Depending on the nature of X, $R^1$, $R^2$, $R^3$, $R^4$, $R^5$ and $R^6$ different synthetic strategies may be selected for the synthesis of compounds of Formula (I).

Compounds of Formula (I) may be obtained by metal catalysed cross-coupling reaction. For instance, they may be obtained by Suzuki coupling reaction between an aryl halide (P1), where X may be Br or I, and a boronic acid or ester (P2), where $R^7$ may be H, for boronic acid derivatives, or any alkyl or substituted alkyl groups for boronic ester derivatives, including optionally —B(OR$^7$)$_2$ forming a cycle such as boronic acid pinacol ester (Scheme 1 below) (Bellina et al., 2004, *Synthesis*, 2419).

Different palladium complexes may be used, such as Pd(PPh$_3$)$_4$, [1,1'-bis(diphenyl phosphino)ferrocene]palladium(II) chloride (Pd(dppf)Cl$_2$), PdCl$_2$(PPh$_3$)$_2$, Pd(OAc)$_2$, with the possible addition of phosphine ligands such as PPh$_3$. Different organic or inorganic bases may be used, such as TEA, DIEA, sodium alcoholate, such as NaOMe or NaOEt, KF, or any carbonate salts, such as K$_2$CO$_3$, Na$_2$CO$_3$, Cs$_2$CO$_3$. The solvent or solvents mixture may be selected between THF, Toluene, Dioxane, MeOH, MeCN, DMF, water, etc. The choice of solvent or solvents mixture may depend on the nature of the base, (P1) and (P2). The resulting reaction mixture may be heated, under inert atmosphere, at different temperatures, with the possible use of microwave action. All the different combinations described above may be used.

Scheme 1

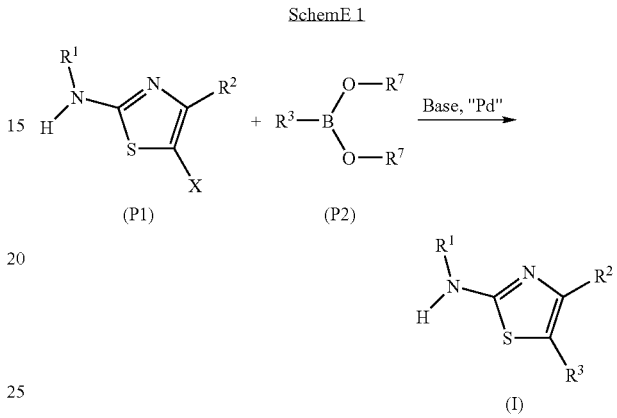

Stille coupling may be used for the preparation of compounds of Formula (I), involving the reaction between an aryl halide (P1), where X may be Br or I, and a tin reagent (P3), where $R^8$ is methyl or n-butyl (Scheme 2, below). This reaction may be catalysed by different palladium complexes, such as Pd(PPh$_3$)$_4$, [1,1'-bis(diphenylphosphino)ferrocene]palladium(II) chloride (Pd(dppf) Cl$_2$), PdCl$_2$(PPh$_3$)$_2$, Pd(OAc)$_2$, with the possible addition of phosphine ligands, such as PPh$_3$, and chlorine salts, such as LiCl or ZnCl$_2$.

Scheme 2

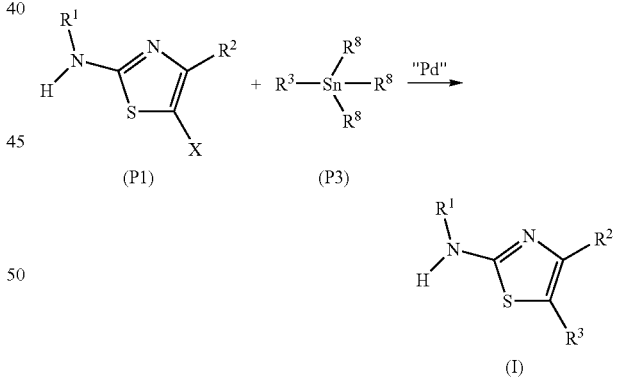

If the above set of metal catalysed cross-coupling reaction conditions is not applicable to obtain compounds according to Formula (I), suitable methods of preparation known by a person skilled in the art should be used.

Compounds of Formula (I) can be converted to alternative compounds of Formula (I), employing suitable interconversion techniques well known by a person skilled in the art. When $R^4$ is H, compounds of Formula (Ia), where $R^3$ may be T1 or T2, may be further functionalised through electrophilic substitutions (Scheme 3 below). For example, chlorosulfonation with chlorosulfonic acid, followed by reaction with PCl$_5$/POCl$_3$ may afford the corresponding sulfonyl chloride (P4).

Intermediate (P4) may further react with an amine, HNR⁹R¹⁰, wherein R⁹ and R¹⁰ are selected from H, optionally substituted C₁-C₆-alkyl (e.g. allyl, 2-hydroxyethyl), optionally —NR⁹R¹⁰ may form a ring, and may be selected from substituted heterocycloalkyl, such as optionally substituted piperidine (e.g. 3-hydroxypiperidin-1-yl, 4-hydroxypiperidin-1-yl), optionally substituted morpholine (e.g. morpholin-4-yl) and optionally substituted 8-(1,4-Dioxa-8-azaspiro[4.5]decane), in the presence of a base, e.g. TEA, DIEA, pyridine, etc, yielding compounds of Formula (Ib) (Compounds of Formula (I) wherein R⁴=SO₂NR⁹R¹⁰), an amino sulfonyl as defined above and where R³ may be T1 or T2. Other electrophilic substitutions may be performed on compound of formula (Ia), such as bromination, nitration, formylation, acylation, etc. using conditions known by a person skilled in the art (for example, see Beaton et al., 1976, *J. Chem. Soc., Perkin I*, 2355-2363).

Compound of Formula (Ia) may be obtained directly from a metal catalysed cross-coupling reaction, performing the reaction between (P1) and the suitable substituted thiophene (P2) or (P3).

Boronic acid or ester (P2) may be commercially available from various sources or synthesized, as it will be detailed below in the examples, using conditions known by a person skilled in the art. A boronic acid (P2a) may be transformed into the corresponding boronic ester (P2b), by heating (P2a) in the presence of an alcohol or a diol (Scheme 4 below). Boronic ester (P2b) may be transformed into alternative boronic ester, using conditions known by a person skilled in the art.

Scheme 3

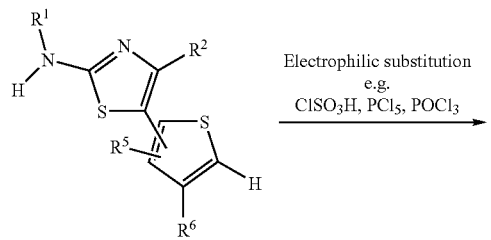

(Ia)

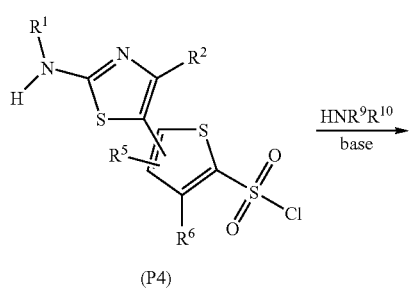

(P4)

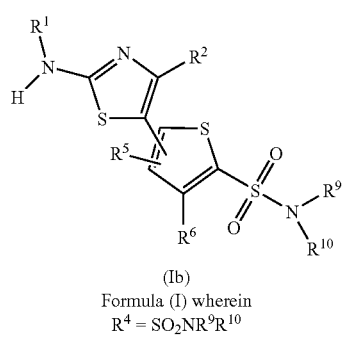

(Ib)
Formula (I) wherein
R⁴ = SO₂NR⁹R¹⁰

Scheme 4

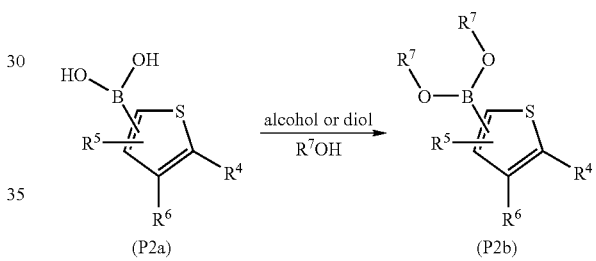

(P2a)     (P2b)

Pinacol boronic ester (P2c) may be prepared by a metal coupling reaction between the corresponding thiophene halide, (P4), where X=50 Br, I, etc, and bis(pinacolato)diboron (P5) or pinacol borane (P6) (Scheme 5 below). This reaction may be catalyzed by different palladium complexes may be used, such as Pd(PPh₃)₄, [1,1'-bis(diphenylphosphino)ferrocene]palladium(II) chloride (Pd(dppf)Cl₂), PdCl₂(PPh₃)₂, Pd(OAc)₂, with the possible addition of phosphine ligands such as PPh₃.

Different organic or inorganic bases may be used, such as TEA, DIEA, KF, KOH, or any carbonate salts, such as K₂CO₃, Na₂CO₃, Cs₂CO₃. The solvent or solvents mixture may be selected between THF, Toluene, Dioxane, MeOH, MeCN, DMF, water, etc. The resulting reaction mixture may be heated, under inert atmosphere, at different temperatures, with the possible use of microwave action. All the different combinations described above may be used.

Scheme 5

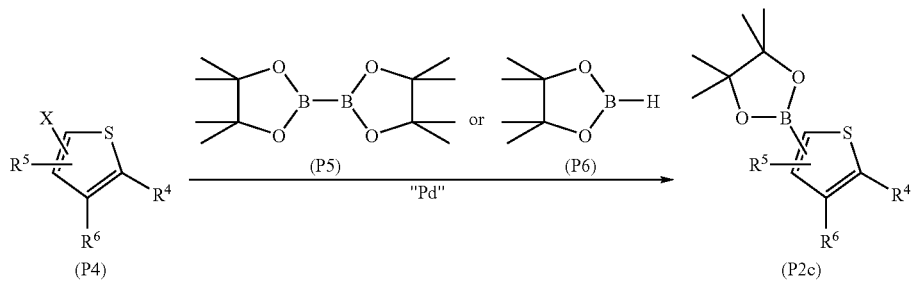

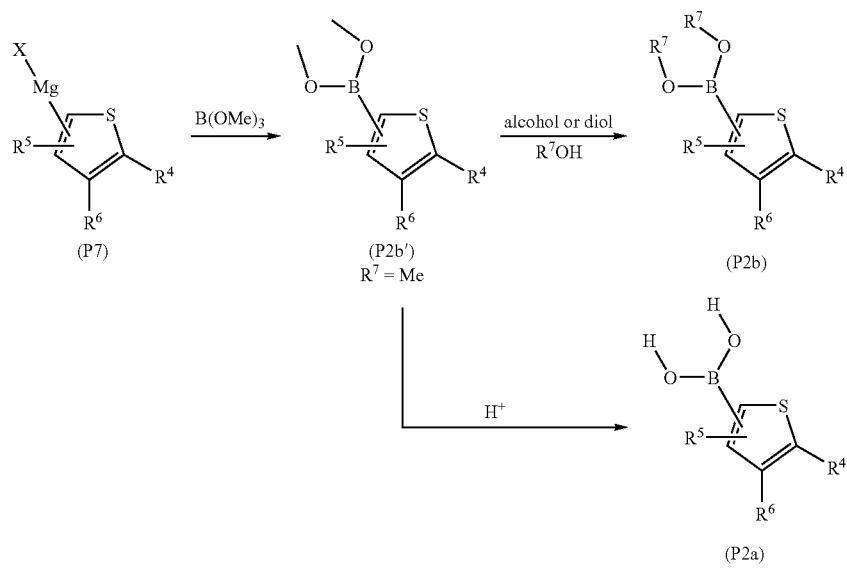

Thiophene halide (P4) may be first transformed into the corresponding thiophene Grignard reagent (P7), which may react with trialkylborate, e.g. B(OMe)$_3$, followed either by an acidic work-up to afford the corresponding boronic acid (P2a) or by a treatment with a suitable alcohol or diol R$^7$OH to afford the corresponding boronic ester (P2b).

Direct 2-borylation may be obtained by iridium catalyzed reaction from 2-unsubstituted thiophene derivatives (P8) (Scheme 6 below). The iridium(I) complex generated from ½[Ir(OMe)(COD)]$_2$ and 4,4'-di-tert-butyl-2,2'-bipyridine catalyzed the direct borylation of thiophenes derivatives in stoichiometric amounts relative to bis(pinacolato)diboron, affording thiophene-2-boronic ester (P2c').

Scheme 6

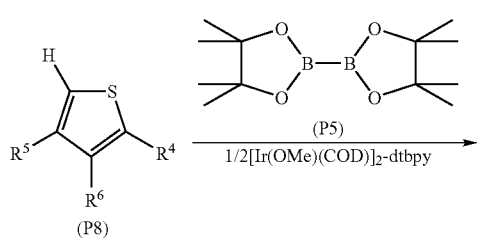

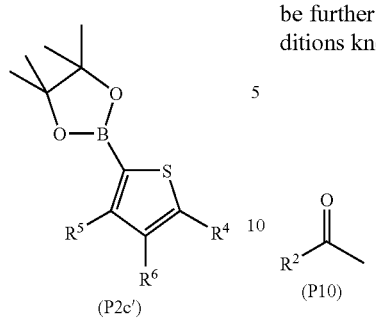

(P2c′)

If the above set of conditions combination is not applicable to obtain boronic ester or acid (P2), suitable methods of preparation known by a person skilled in the art should be used. Organotin reagents (P3) may be commercially available from various sources or synthesized, using conditions known by a person skilled in the art.

Compounds of formula (P1) with X=Br or I may be prepared by halogenation of the corresponding thiazole (P9) with reagents such as Br$_2$, I$_2$ or NBS, NIS (Scheme 7, below). Depending on the nature of R$^1$, protection of the secondary amine may be needed before the halogenation, with for example PG=acetyl or any other group which is easily removable.

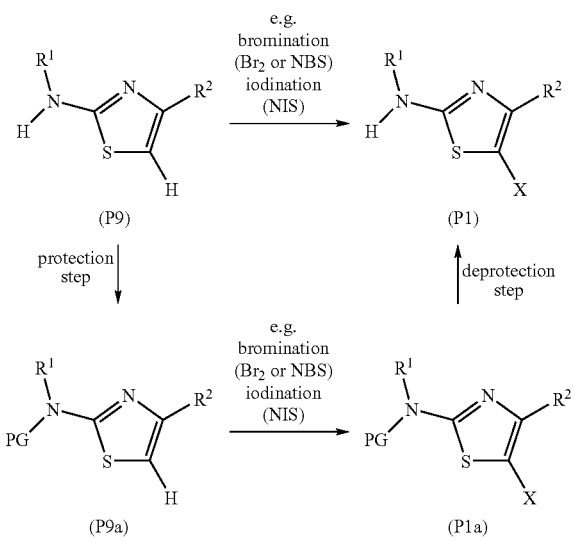

Thiazole (P9) may be commercially available from various sources or synthesized, using conditions known by a person skilled in the art, using both solution-phase and solid-phase chemistry protocols (Kodomari et al., 2002, above). For example, it may be obtained in two steps (Scheme 8 below), starting with α-halogenation of a ketone (P10), using for example Br$_2$ for a bromination or thionyl chloride for a chlorination, affording an intermediate (P11). "Hal" in intermediate (P11) can be also a tosyloxy group, which may be introduced with suitable reagents such as hydroxy(tosyloxy)iodobenzene. Intermediate (P11) may be then added to a solution of a substituted thiourea R$^1$NHC(S)NH$_2$ (P12) in a suitable solvent, preferably a polar solvent, e.g. EtOH, leading to intermediate (P9). The resulting intermediate (P11) may react with thiourea, affording thiazole (P13) which may be further substituted with R$^1$, as defined above, using conditions known by a person skilled in the art.

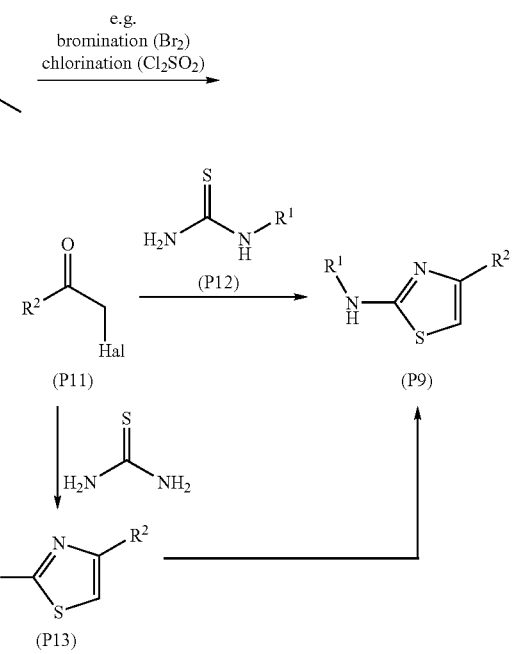

Thioureas (P12) used in synthetic Scheme 8 above are either commercially available from various sources or synthesized using conditions known by the person skilled in the art. For example, thioureas (P12) can be obtained by coupling a salt of an amine R$^1$NH$_2$, preferably HCl salt, with potassium thiocyanate used in equimolarity in TBF under reflux as shown on Scheme 9 below, Pathway A.

Scheme 9

Pathway A

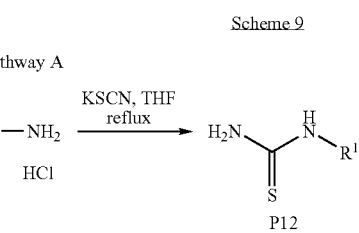

Pathway B

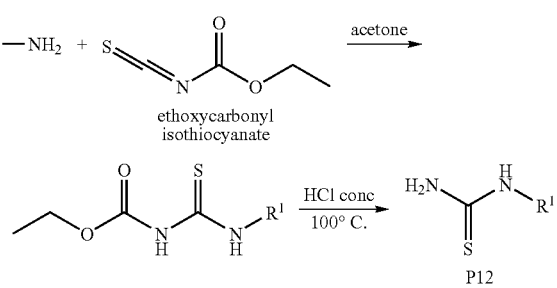

Pathway C

-continued

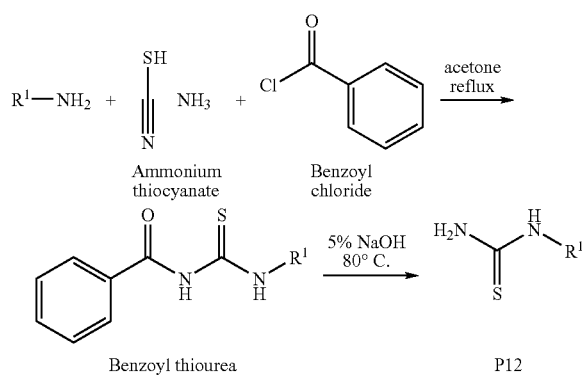

Pathway D

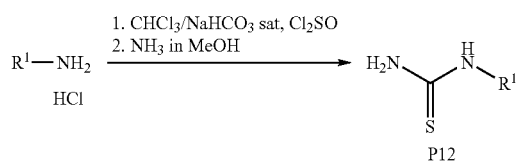

Pathway E

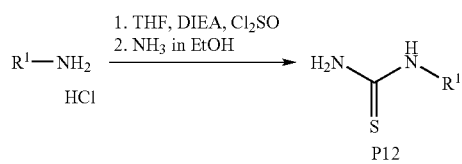

The amine $R^1NH_2$ can be first activated with ethoxycarbonyl isothiocyanate affording an ethoxycarbonyl thiourea intermediate, as presented above on Scheme 9, Pathway B. Upon deprotection under acidic conditions, e.g. concentrated HCl, the desired thiourea (P12) is released. The amine $R^1NH_2$ can be also activated with benzoyl isothiocyanate, which is obtained by addition of benzoyl chloride to ammonium thiocyanate, giving a benzoyl thiourea intermediate, as shown above on Scheme 9, Pathway C. Upon deprotection under basic conditions, e.g. NaOH, the desired thiourea (P12) is released. Alternatively, the amine $R^1NH_2$ can react with thiophosgene, followed by the addition of ammonia, as presented above on Scheme 9, Pathway D. If the above set of synthetic methods are not applicable to obtain N-substituted thiourea (P12), suitable methods of preparation known by a person skilled in the art should be used.

Methods of Preparing Intermediates of Compounds of Formula (I).

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

EXAMPLES

The Following Starting Materials Commercially Available Were Used

PyBOP (Novabiochem), 2-(tributylstannyl)thiophene (Aldrich), 5-(dihydroxyboryl)-2-thiophenecarboxylic acid (Acros), 3-(4,4,5,5-tetramethyl-1,3,2-dioxaborolan-2-yl)thiophene (Boron-Mol), 5-formyl-2-thiopheneboronic acid (Aldrich), 2-acetamido-4-methylthiazole (Aldrich), pinacol (Aldrich), (trimethylsilyl)diazomethane 2N solution (Aldrich), Pd(dppf)Cl$_2$ (Avocado), cesium carbonate (Fluka), potassium fluoride (Fluka), copper acetate (Fluka), allylamine (Fluka), morpholine (Fluka), ethanolamine (Fluka), 4-hydroxypiperidine (Aldrich), 3-hydroxypiperidine (Aldrich), ammonia in MeOH 2N solution (Aldrich), 1,4-Dioxa-8-azaspiro[4.5]decane (Aldrich), chlorosulfonic acid (Fluka), phosphorus pentachloride (Aldrich), phosphorus oxide chloride (Aldrich), hydroxylamine hydrochloride (Fluka).

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak® HR C186 µm 60 Å, 40×30 mm (up to 100 mg) or with XTerra® Prep MS C8, 10 µm, 50×300 mm (up to 1 g). All the purifications are performed with a gradient of MeCN/H$_2$O 0.09% TFA. The semi-preparative reverse-phase HPLC are performed with the Biotage Parallex Flex System equipped with columns Supelcosil™ ABZ+Plus (25 cm×21.2 mm, 12 µm); UV detection at 254 nm and 220 nm; flow 20 ml/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

The microwave chemistry is performed on a single mode microwave reactor Emrys™ Optimiser from Personal Chemistry.

Intermediate 1: Preparation of N-(5-iodo-4-methyl-1,3-thiazol-2-yl)acetamide (Intermediate (P1) wherein $R^1$ is $C(O)CH_3$, $R^2$ is $CH_3$ and X is I).

Intermediate 1

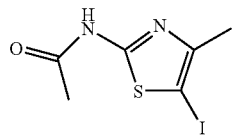

To a solution of 2-Acetamido-4-methylthiazole (5 g; 32.01 mmol; 1 eq.) in MeCN (100 ml) is added N-iodosuccinimide (8.642 g; 38.41 mmol; 1.2 eq.). The resulting homogeneous solution is stirred at rt. After 5 min, a precipitate is formed. It is filtrated and washed with cold MeCN. A first batch of Intermediate 1 is isolated as white-off solid (5.072 g; 57%). The mother liquors are evaporated and dissolved in EtOAc. They are washed with two fraction of $Na_2S_2O_3$ 1N solution and dried over $MgSO_4$. After filtration and evaporation of the solvents, the resulting solid is suspended in MeCN, filtrated and dried under vacuo, affording a second batch of Intermediate 1 as white-off solid (1.813 g; 20%). The overall yield of this reaction is 77%. $^1$H NMR (DMSO-$d_6$, 300 MHz) δ 1.88 (s, 3H), 2.02 (s, 3H), 12.02 (s, 1H). M$^-$ (ESI): 281.02; M$^+$ (ESI): 283.09. HPLC, Rt: 2.55 min (purity: 100%).

Example 1

N-(4-methyl-5-{5-[(prop-2-yn-1-ylamino)sulfonyl]-2-thienyl}-1,3-thiazol-2-yl)acetamide (1)

(1)

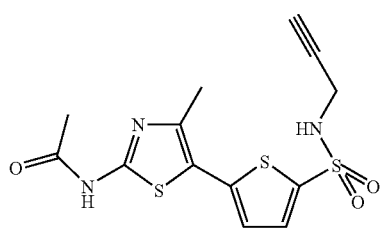

Step I: N-[4-methyl-5-(2-thienyl)-1,3-thiazol-2-yl]acetamide

N-(5-iodo-4-methyl-1,3-thiazol-2-yl)acetamide, Intermediate 1 (2 g; 7.09 mmol; 1 eq.) and Pd(dppf)Cl$_2$ (0.52 g; 0.71 mmol; 0.10 eq.) are dissolved in DMF (35 ml). 2-(Tributylstannyl)thiophene (2.68 ml; 8.44 mmol; 1.19 eq.) is added. The reaction mixture is flushed with argon and heated at 100° C. for 1 h30. Solvents are evaporated and the crude mixture is dissolved in EtOAc (100 ml), washed with water (3×100 ml). The aqueous phase are combined and extracted with EtOAc (2×50 ml). Combined organic phases is washed with brine and dried over MgSO$_4$. After evaporation of the solvents, the crude product is purified by preparative HPLC, affording N-[4-methyl-5-(2-thienyl)-1,3-thiazol-2-yl]acetamide as white-off powder (1.24 g; 73.5%). $^1$H NMR (DMSO-$d^6$) δ 2.16 (s, 3H), 2.42 (s, 3H), 7.15 (dd, J=3.8, 5.3 Hz, 1H), 7.20 (dd, J=1.1, 3.8 Hz, 1H), 7.60 (dd, J=1.1, 5.3 Hz, 1H), 12.19 (s, 1H). M$^-$ (ESI): 237.01; M$^+$ (ES): 239.01. HPLC, Rt: 3.01 min (purity: 98.7%).

Step II: 5-[2-(acetylamino)-4-methyl-1,3-thiazol-5-yl]thiophene-2-sulfonyl chloride N-[4-methyl-5-(2-thienyl)-1,3-thiazol-2-yl]acetamide, prepared in Step I (500 mg; 2.10 mmol; 1 eq.) is dissolved in DCM (30 ml). The reaction mixture is cooled down to 0° C. and chlorosulfonic acid (0.70 ml; 10.49 mmol; 5 eq.) dissolved in DCM (30 ml) is added dropwise over 15 min. The solution becomes pink. It is stirred 15 minutes at 0° C. Phosphorus pentachloride (873.7 mg; 4.20 mmol; 2 eq.) and phosphorus oxide chloride (0.78 ml; 8.39 mmol; 4 eq.) are added successively. The reaction mixture is stirred for 2 additional hours at room temperature. It is poured on ice and the desired product is extracted with 2 portions of EtOAc, dried over MgSO$_4$, and evaporated, affording 5-[2-(acetylamino)-4-methyl-1,3-thiazol-5-yl]thiophene-2-sulfonyl chloride as yellow solid (650 mg; 92%). M$^-$(ESI): 335.08; M$^+$ (ESI): 337.08.

Step III: N-(4-methyl-5-{5-[(prop-2-yn-1-ylamino)sutronyl]-2-thienyl}-1,3-thiazol-2-yl)acetamide (1)

5-[2-(acetylamino)-4-methyl-1,3-thiazol-5-yl]thiophene-2-sulfonyl chloride, prepared in Step II (200 mg; 0.59 mmol; 1 eq) is dissolved in anhydrous DCM (10 ml). The reaction is put under nitrogen. Prop-2-ynylamine (0.08 ml; 1.19 mmol; 2 eq), diisopropylethylamine (0.61 ml; 3.56 mmol; 6 eq) are added successively and the reaction mixture is stirred for 3 hours at room temperature. Solvents are evaporated and the resulting crude product is purified by preparative HPLC. Compound (1) is isolated as a beige powder (25 mg; 12%). $^1$H NMR (DMSO-$d_6$, 300 MHz) δ 2.15 (s, 3H), 2.43 (s, 3H), 3.13 (t, J=3 Hz, 1H), 3.77 (q, J=6 Hz, 2H), 7.20 (d, J=3 Hz, 1H), 7.58 (d, J=6 Hz, 1H), 8.4 (t, J=6 Hz, 1H), 12.31 (s, 1H). M$^-$ (ES): 354.2; M$^+$ (ESI): 356.1. HPLC (method A), Rt: 2.88 min (purity: 100%).

Example 2

N-(5-{5-[(4-acetylpiperazin-1-yl)sulfonyl]-2-thienyl}-4-methyl-1,3-thiazol-2-yl)acetamide (2)

(2)

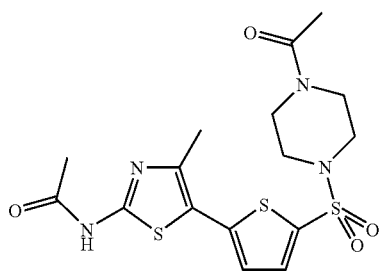

5-[2-(acetylamino)-4-methyl-1,3-thiazol-5-yl]thiophene-2-sulfonyl chloride, prepared as in Step II of Example 1 (100 mg; 0.3 mmol; 1 eq) is dissolved in anhydrous DCM (5 ml). The reaction is put under nitrogen. 1-Piperazin-1-yl-ethanone (76.1 mg; 0.59 mmol; 2 eq), diisopropylethylamine (0.3 ml; 1.78 mmol; 6 eq) are added successively and the reaction mixture is stirred for 3 hours at room temperature. The solvents are evaporated and the crude product is purified by preparative HPLC. Compound (2) is isolated as a pale yellow powder (35 mg; 27%).

$^1$H NMR (DMSO-$d_6$, 300 MHz) δ 1.80 (s, 3H), 2 (s, 3H), 2.30 (s, 3H), 2.82 (m, J=21 Hz, 4H), 3.38 (d, J=3 Hz, 4H), 7.15 (d, J=6 Hz, 1H), 7.45 (d, J=3 Hz, 1H), 12.18 (s, 1H). M⁻ (ESI): 427.1; M⁺ (ESI): 429.0. HPLC (method A), Rt: 2.86 min (purity: 99.8%).

Example 3

N-{5-[5-({[2-(dimethylamino)ethyl]amino}sulfonyl)-2-thienyl]-4-methyl-1,3-thiazol-2-yl}acetamide (3)

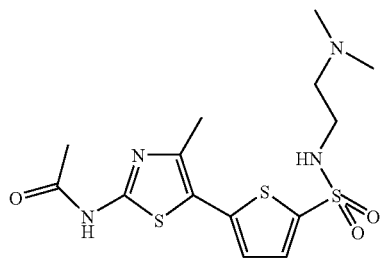

(3)

5-[2-(acetylamino)-4-methyl-1,3-thiazol-5-yl]thiophene-2-sulfonyl chloride, prepared as in Step II of Example 1 (1000 mg; 2.97 mmol; 1 eq) is dissolved in anhydrous DCM (100 ml). The reaction is put under nitrogen. 2-Dimethylaminoethylamine (0.97 ml; 8.91 mmol; 3 eq), triethylamine (1.66 ml; 11.9 mmol; 4 eq) are added successively and the reaction mixture is stirred overnight at room temperature. After 15 hours, to complete the reaction, triethylamine (4 eq) and 2-dimethylaminoethylamine (3 eq) are added. After one hour the reaction is complete. The reaction mixture is then wash with NH₄Cl sat. (twice) and brine. The organic layer is dried over MgSO₄ and the solvents are evaporated. The resulting crude product is dissolved in DCM and extracted with HCl 1N. The aqueous phase is washed with DCM (3 times) and basified with NaOH 5N until pH 10. The desired product is extracted with EtOAc (3 times). Combined organic phases are dried over MgSO₄, filtrated and evaporated, affording Compound (3) as a beige solid (480 mg; 40%).

¹H NMR (DMSO-d₆, 300 MHz) δ 2.08 (s, 6H), 2.14 (s, 3H), 2.25 (t, J=6 Hz, 2H), 2.43 (s, 3H), 2.94 (t, J=9 Hz, 2H), 7.20 (d, J=3 Hz, 1H), 7.55 (d, J=6 Hz, 1H), 7.81 (s, 1H), 12.30 (s, 1H). M⁻ (ESI): 387.2; M⁺ (ESI): 389.2. HPLC (method A), Rt: 1.96 min (purity: 98.0%).

Example 4

N-[4-methyl-5-(5-{[(1-methylpiperidin-4-yl)amino]sulfonyl}-2-thienyl)-1,3-thiazol-2-yl]acetamide (4)

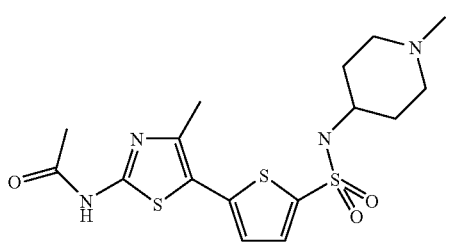

(4)

5-[2-(acetylamino)-4-methyl-1,3-thiazol-5-yl]thiophene-2-sulfonyl chloride, prepared as in Step 1 of Example 9 (110 mg; 0.33 mmol; 1 eq.), is dissolved in a mixture of DCM/DMF(1/1, 10 ml). 4-Amino-1-methylpiperidine (188 mg; 1.65 mmol; 5 eq.) and DIEA (0.17 ml; 0.98 mmol; 3 eq.) are added. After 3 hours, the solvents are evaporated. The crude product is dissolved in DCM and washed with NH₄Cl saturated solution, water and dried over MgSO₄. After evaporation of the solvents, crude material is dissolved in DCM (3 ml) and title compound precipitated with Et2O affording after filtration, compound (4) as a white powder (120 mg; 90%). ¹H NMR (DMSO-d⁶) δ 1.25 (m, 2H), 1.55 (m, 2H), 1.80 (m, 2H), 2.05 (m, 2H), 2.25 (s, 6H), 2.40 (s, 3H), 3.05 (m, 1H), 6.95 (d, J=3 Hz, 1H), 7.52 (d, J=3 Hz, 1H), 12.23 (m, 1H). M⁻ (ESI): 413.30; M⁺ (ESI): 415.30. HPLC, Rt: 2.08 min (purity: 99.33%).

Example 5

N-(5-{5-[(2-Dimethylamino-ethyl)-methyl-sulfamoyl]-thiophen-2-yl}-4-methyl-thiazol-2-yl)-acetamide (5)

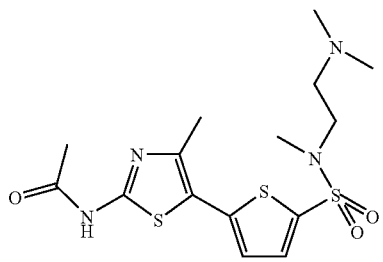

(5)

5-[2-(acetylamino)-4-methyl-1,3-thiazol-5-yl]thiophene-2-sulfonyl chloride, prepared as in Step II of Example 1 (500 mg; 1.48 mmol; 1 eq), is dissolved in anhydrous DCM (50 ml). The reaction is put under nitrogen. N,N,N'-Trimethyl-ethane-1,2-diamine (0.58 ml; 5.94 mmol; 3 eq) and triethylamine (0.83 ml; 5.94 mmol; 4 eq) are added successively and the reaction mixture is stirred overnight at room temperature. The reaction mixture is washed with NH₄Cl sat. (2 times), water (3 times), brine, and dried over MgSO₄. After evaporation of the solvents, the crude product is suspended in ACN, filtered and dried under vacuum, affording Compound (5) as a beige solid (309 mg; 41%).

¹H NMR (DMSO-d₆, 300 MHz) δ 2.14 (s, 6H), 2.15 (s, 3H), 2.40 (t, J=6 Hz, 2H), 2.44 (s, 3H), 2.77 (s, 3H), 3.10 (t, J=6 Hz, 2H), 7.28 (s, 1H), 7.63 (s, 1H), 12.33 (s, 1H). M⁻ (ESI): 401.2; M⁺ (ESI): 403.3. HPLC (method A), Rt: 2.10 min (purity: 94.4%).

Example 6

5-(2-amino-4-methyl-1,3-thiazol-5-yl)-N-(2-morpholin-4-ylethyl)thiophene-2-sulfonamide (6)

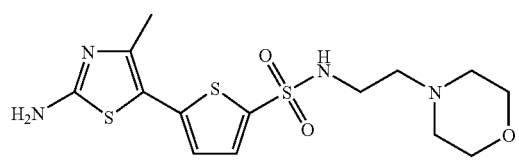

(6)

To N-[4-methyl-5-(5-{[(2-morpholin-4-ylethyl)amino]sulfonyl}-2-thienyl)-1,3-thiazol-2-yl]acetamide (9) (240 mg;

0.56 mmol; 1 eq) is added hydrochloric acid 1.25 M in EtOH (8.9 ml; 1.25 M; 11.2 mmol; 20 eq). The mixture is stirred overnight at 90° C. The mixture is cooled down to room temperature. The resulting precipitate is filtrated and rinsed with cold EtOH, affording Compound (6) as a yellowish solid (241.5 mg; 94%).

$^1$H NMR (DMSO-$d_6$, 300 MHz) δ 2.33 (s, 3H), 3.11 (m, 2H), 3.22 (m, 2H), 3.29 (m, 2H), 3.41 (m, 2H), 3.76 (m, 2H), 3.93 (m, 2H), 7.17 (d, J=4 Hz, 1H), 7.63 (d, J=4 Hz, 1H), 8.40 (t, J=6 Hz, 1H), 8.72 (br s, 2H), 11.06 (br s, 1H). HPLC (method A), Rt: 1.02 min (purity: 99.8%). M$^-$ (ESI): 387.20; M$^+$ (ESI): 389.20.

Example 7

Methyl 5-{[4-methyl-5-(5-{[(2-morpholin-4-ylethyl)amino]sulfonyl}-2-thienyl)-1,3-thiazol-2-yl]amino}-5-oxopentanoate (7)

(7)

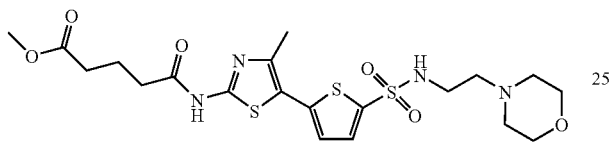

To a degassed solution of 5-(2-amino-4-methyl-1,3-thiazol-5-yl)-N-(2-morpholin-4-ylethyl)thiophene-2-sulfonamide (6) (100 mg; 0.22 mmol; 1 eq) in anhydrous THF (10 ml), N-[(1H-1,2,3-benzotriazol-1-yloxy)(dimethylamino)methylene]-N-methylmethanaminium tetrafluoroborate (104.4 mg; 0.33 mmol; 1.50 eq), mono-methyl glutarate (68 µl; 0.54 mmol; 2.50 eq) and N,N-diisopropylethylamine (148 µl; 0.87 mmol; 4 eq) are added successively. The reaction mixture is stirred at room temperature for three days. Solvents are evaporated under vacuum. The resulting crude product is dissolved in EtOAc and washed with NH$_4$Cl sat. solution, water, brine and dried over MgSO4. After evaporation of the solvents, the crude product is purified by flash chromatography (CH$_3$Cl/MeOH gradient from 1/0 to 1/1 over 40 min), affording Compound (7) as a yellow solid (68.5 mg; 61.18%).

$^1$H NMR (DMSO-$d_6$, 300 MHz) δ 2.05 (quint., J=6 Hz, 2H), 2.34 (m, 4H), 2.46 (m, 9H), 3.13 (m, 2H), 3.63 (m, 4H), 3.68 (s, 3H), 5.38 (br s, 1H), 7.01 (d, J=4 Hz, 1H), 7.53 (d, J=4 Hz, 1H), 9.17 (br s, 1H). HPLC (method A), Rt: 2.28 min (purity: 95.7%). M$^-$ (ESI): 515.21; M$^+$ (ESI): 517.40.

Example 8

N-(4-methyl-5-{5-[(4-methylpiperazin-1-yl)sulfonyl]-2-thienyl}-1,3-thiazol-2-yl)acetamide (8)

(8)

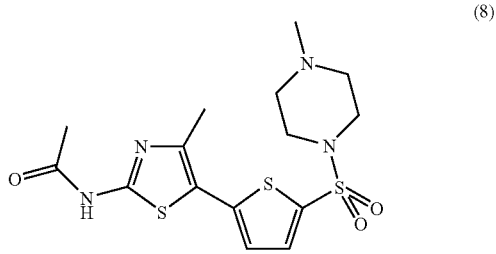

5-[2-(acetylamino)-4-methyl-1,3-thiazol-5-yl]thiophene-2-sulfonyl chloride, prepared as in Step II of Example 1 (280 mg; 0.84 mmol; 1 eq), is dissolved in DCM (10 ml). N-Methyl piperazine (8.4 ml; 8.4 mmol; 10 eq) and DIEA (0.17 ml; 0.98 mmol; 3 eq) are added. After four hours, water (1 ml) is added and the solvents are evaporated to dryness. The crude product is re-dissolved in DCM and washed with NH$_4$Cl saturated solution, water and dried over MgSO$_4$. After evaporation of the solvents, crude material is precipitated in a mixture of DCM and diethyl ether, affording after filtration, Compound (8) as a white solid (173 mg; 51%).

$^1$H NMR (DMSO-$d_6$, 300 MHz) δ1.95 (s, 3H), 2.05 (s, 3H), 2.28 (m, 7H), 2.80 (m, 4H), 7.10 (d, J=6 Hz, 1H), 7.40 (d, J=6 Hz, 1H), 12.14 (m, 1H). M$^-$ (ESI): 399.3; M$^+$ (ESI): 401.3. HPLC (method A), Rt: 2.13 min (purity: 100%).

Example 9

N-(4-methyl-5-{5-[(2-morpholin-4-ylethyl)amino]sulfonyl}-2-thienyl)-1,3-thiazol-2-yl)acetamide (9)

(9)

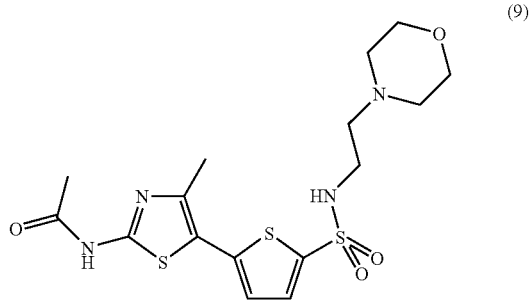

5-[2-(acetylamino)-4-methyl-1,3-thiazol-5-yl]thiophene-2-sulfonyl chloride, prepared as in Step I of Example 9 (4000 mg; 11.9 mmol; 1 eq), is dissolved in anhydrous DCM (400 ml). The reaction is put under nitrogen. 2-Morpholin-4-yl-ethylamine (4638 mg; 35.6 mmol; 3 eq), triethylamine (6.6 ml; 47.5 mmol; 4 eq) are added successively and the reaction mixture is stirred overnight at room temperature. HCl 1N is added to the reaction mixture. The aqueous phase is washed with DCM (3 times) and basified with NaOH 5N until pH 10. The desired product is extracted with EtOAc (3 times), affording Compound (22) as white solid (3134 mg; 60%).

$^1$H NMR (DMSO-$d_6$, 300 MHz) δ 2.14 (s, 3H), 2.30 (m, 4H), 2.34 (t, J=6 Hz, 2H), 2.43 (s, 3H), 2.98 (t, J=9 Hz, 2H), 3.50 (t, J=6 Hz, 4H), 7.20 (s, 1H), 7.56 (s, 1H), 7.83 (s, 1H), 12.31 (s, 1H) M$^-$ (ESI): 429.3; M$^+$ (ESI): 431.3. HPLC (method A), Rt: 1.95 min (purity: 99.3%).

Example 10

N-{5-[5-({[3-(dimethylamino)propyl]amino}sulfonyl)-2-thienyl]-4-methyl-1,3-thiazol-2-yl}acetamide (10)

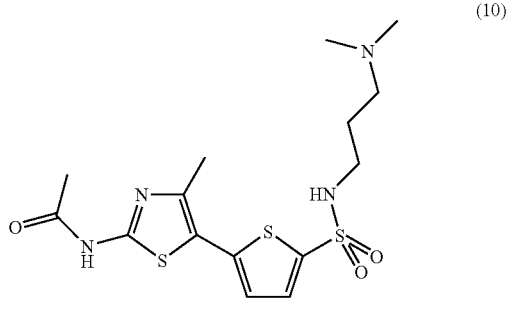

(10)

5-[2-(acetylamino)-4-methyl-1,3-thiazol-5-yl]thiophene-2-sulfonyl chloride, prepared as in Step II of Example 1 (280 mg; 0.84 mmol; 1 eq), is dissolved in DCM (10 ml). N,N-dimethylpropane-1,3-diamine (0.89 ml; 8.4 mmol; 10 eq) and DIEA (0.17 ml; 0.98 mmol; 3 eq) are added. After one night reaction, water (1 ml) is added and the solvents are evaporated to dryness. The crude product is re-dissolved in DCM and washed with NH$_4$Cl saturated solution, water and dried over MgSO$_4$. After evaporation of the solvents, crude material is precipitated in a mixture of DCM and diethyl ether, affording after filtration, Compound (10) as a white solid (105 mg; 28%).

$^1$H NMR (DMSO-d$_6$, 300 MHz) δ 1.80 (m, 2H), 2.16 (s, 3H), 2.45 (s, 3H), 2.71 (s, 6H), 2.94 (q, J=6 Hz, 2H), 3.05 (m, 2H), 7.23 (d, J=6 Hz, 1H), 7.59 (d, J=6 Hz, 1H), 8.08 (m, 1H), 10.22 (m, 1H). M$^-$ (ESI): 401.4; M$^+$ (ESI): 403.4. HPLC (method A), Rt: 2.07 min (purity: 99.7%).

Example 11

N-(4-methyl-5-{5-[(piperazin-1-yl)sulfonyl]-2-thienyl}-1,3-thiazol-2-yl) acetamide (11)

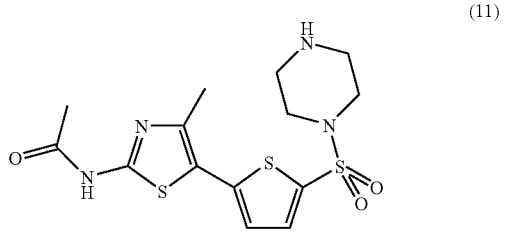

(11)

5-[2-(acetylamino)-4-methyl-1,3-thiazol-5-yl]thiophene-2-sulfonyl chloride, prepared as in Step II of Example 1 (280 mg; 0.84 mmol; 1 eq), is dissolved in DCM (10 ml). N-Methyl piperazine (1.4 g; 16.8 mmol; 20 eq) and DIEA (0.17 ml; 0.98 mmol; 3 eq) are added. After one night reaction, water (1 ml) is added and the solvents evaporated to dryness. The crude product is re-dissolved in DCM and washed with NH$_4$Cl saturated solution, water and dried over MgSO$_4$. After evaporation of the solvents, crude material is precipitated in a mixture of DCM and diethyl ether, affording after filtration, Compound (11) as a white solid (125 mg; 40%).

$^1$H NMR (DMSO-d$_6$, 300 MHz) δ 2.17 (s, 3H), 2.47 (s, 3H), 3.24 (s, 8H), 7.38 (d, J=6 Hz, 1H), 7.70 (d, J=6 Hz, 1H), 9.12 (m, 1H), 12.39 (m, 1H). M$^-$ (ESI): 385.3; M$^+$ (ESI): 387.3. HPLC (method A), Rt: 2.09 min (purity: 100%).

Example 12

N-2-({5-[2-(acetylamino)-4-methyl-1,3-thiazol-5-yl]-2-thienyl}sulfonyl)-N-methylglycinamide (12)

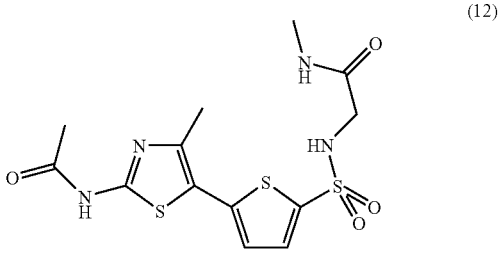

(12)

5-[2-(acetylamino)-4-methyl-1,3-thiazol-5-yl]thiophene-2-sulfonyl chloride, prepared in Step II of Example 1 (110 mg; 0.33 mmol; 1 eq), is dissolved in a mixture of DCM/DMF (1/1, 10 ml). 2-Amino-N-methyl-acetamide (145 mg; 1.65 mmol; 5 eq) and DIEA (0.17 ml; 0.98 mmol; 3 eq) are added under a nitrogen atmosphere. After 3 hours, the solvents are evaporated. The crude product is dissolved in DCM and washed with NH$_4$Cl saturated solution, water and dried over MgSO$_4$. After evaporation of the solvents, crude material is purified by preparative HPLC, affording Compound (12) as an oil (4 mg; 3%).

$^1$H NMR (DMSO-d$_6$, 300 MHz) δ 1.99 (s, 3H), 2.30 (s, 3H), 2.55 (d, J=3 Hz, 3H), 3.50 (d, J=6 Hz, 2H), 7.21 (d, J=3 Hz, 1H), 7.55 (d, J=3 Hz, 1H), 7.85 (d, J=3 Hz, 1H), 8.24 (t, J=6 Hz, 1H), 12.32 (m, 1H). M$^-$ (ESI): 387.10; M$^+$ (ESI): 389.10. HPLC (method A), Rt: 2.37 min (purity: 100%).

Example 13

N-(5-{5-[(2-(acetylamino)ethyl)amino]sulfonyl-2-thienyl}-4-methyl-1,3-thiazol-2-yl)acetamide (13)

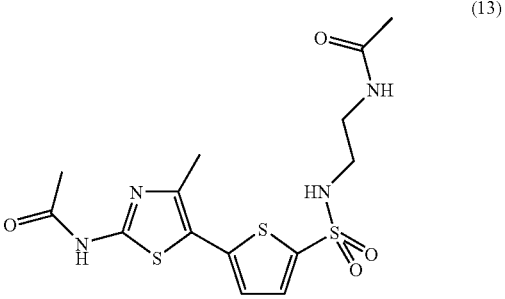

(13)

5-[2-(acetylamino)-4-methyl-1,3-thiazol-5-yl]thiophene-2-sulfonyl chloride, prepared as in Step II of Example 1 (110 mg; 0.33 mmol; 1 eq), is dissolved in a mixture of DCM/DMF (1/1, 10 ml). N-acetylethylene diamine (168 mg; 1.65 mmol; 5 eq) and DIEA (0.17 ml; 0.98 mmol; 3 eq) are added. After 3 hours, the solvents are evaporated. The crude product is dissolved in DCM and washed with NH$_4$Cl saturated solution, water and dried over MgSO₄. After evaporation of the solvents, crude material is dissolved in DCM (3 ml) and title compound precipitates with diethyl ether, affording after filtration, Compound (13) as a yellow powder (14 mg; 11%).

¹H NMR (DMSO-d₆, 300 MHz) δ 1.75 (s, 3H), 2.15 (s, 3H), 2.35 (s, 3H), 2.90 (q, J=6 Hz, 2H), 3.10 (q, J=6 Hz, 2H), 7.21 (d, J=3 Hz, 1H), 7.53 (d, J=3 Hz, 1H), 7.90 (m, 2H), 12.31 (m, 1H). M⁻ (ESI): 401.20; M⁺ (ESI): 403.20. HPLC (method A), Rt: 2.41 min (purity: 92.1%).

Example 14

N-[5-(5-{[(2,2-dimethyl-1,3-dioxolan-4-yl)methyl]aminosulfonyl}-2-thienyl)-4-methyl-1,3-thiazol-2-yl]acetamide (14)

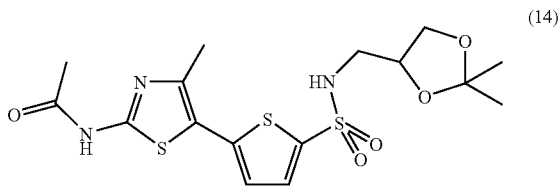

5-[2-(acetylamino)-4-methyl-1,3-thiazol-5-yl]thiophene-2-sulfonyl chloride, prepared as in Step II of Example 1 (110 mg; 0.33 mmol; 1 eq), is dissolved in DCM (10 ml). 2,2-Dimethyl-1,3-dioxolane-4-methanamine (216 mg; 1.65 mmol; 5 eq) and DIEA (0.17 ml; 0.98 mmol; 3 eq) are added. After one hour, the solvents are evaporated. The crude product is dissolved in DCM and washed with NH₄Cl saturated solution, water and dried over MgSO₄. After evaporation of the solvents, crude material is dissolved in DCM (3 ml). Title compound precipitates with addition diethyl ether, affording after filtration, Compound (14) as a white powder (65 mg; 46%).

¹H NMR (DMSO-d₆, 300 MHz) δ1.30 (s, 3H), 1.35 (s, 3H), 2.30 (s, 3H), 2.50 (s, 3H), 3.10 (m, J=6 Hz, 1H), 3.30 (m, J=6 Hz, 1H), 3.70 (m, J=6 Hz, 1H), 4.05 (m, J=6 Hz, 1H), 4.25 (m, J=6 Hz, 1H), 4.93 (t, J=6 Hz, 1H), 7.05 (d, J=3 Hz, 1H), 7.55 (d, J=3 Hz, 1H). M⁻ (ESI): 430.2; M⁺ (ESI): 432.3. HPLC (method A), Rt: 3.06 min (purity: 95.44%).

Example 15

Methyl N-({5-[2-(acetylamino)4-methyl-1,3-thiazol-5-yl]-2-thienyl}sulfonyl)serinate (15)

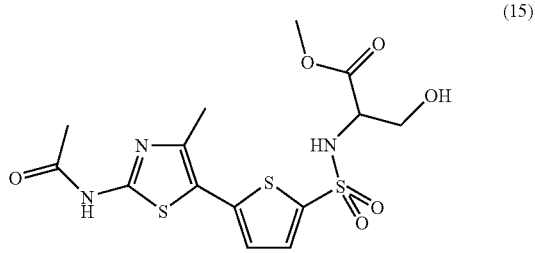

5-[2-(acetylamino)-4-methyl-1,3-thiazol-5-yl]thiophene-2-sulfonyl chloride, prepared as in Step II of Example 1 (110 mg; 0.33 mmol; 1 eq), is dissolved in a mixture of DCM/DMF (1/1, 10 ml). 2-Amino-3-hydroxy-propionic acid methyl ester (0.2 ml; 1.65 mmol; 5 eq) and DIEA (0.17 ml; 0.98 mmol; 3 eq) are added. After one hour, the solvents are evaporated to dryness. The crude product is re-dissolved in DCM and washed with NH₄Cl saturated solution, water and dried over MgSO₄. After evaporation of the solvents, crude material is precipitated in ACN, affording after filtration, Compound (15) as a white powder (54 mg; 39%).

¹H NMR (DMSO-d₆, 300 MHz) δ 1.26 (s, 3H), 2.59 (s, 3H), 3.72 (s, 3H), 4 (m, 2H), 4.15 (m, 1H), 5.75 (d, J=3 Hz, 1H), 7.14 (d, J=3 Hz, 1H), 7.61 (d, J=3 Hz, 1H), 12.35 (m, 1H). M⁻ (ESI): 418.2; M⁺ (ESI): 420.2. HPLC (method A), Rt: 2.50 min (purity: 99.41%).

Example 16

N-({5-[2-acetylamino)-4-methyl-1,3-thiazol-5-yl]-2-thienyl}sulfonyl)serine (16)

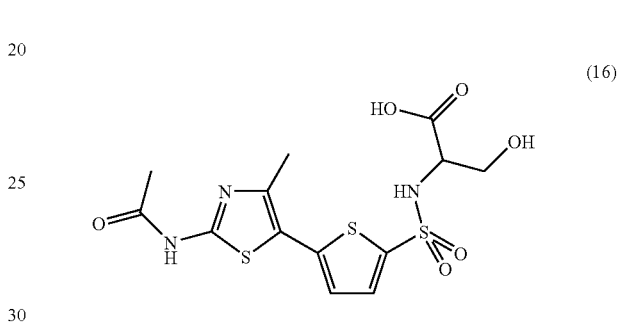

Methyl N-({5-[2-(acetylamino)-4-methyl-1,3-thiazol-5-yl]-2-thienyl}sulfonyl)serinate (15) (48 mg; 0.11 mmol; 1 eq), is dissolved in TBF (2 ml). The resulting solution is cooled down to 0° C. and sodium hydroxide (5M) (0.3 ml; 14 mmol; 12.5 eq) is added slowly. The reaction mixture is stirred at room temperature for 30 minutes, then neutralized with HCl (1M). The solvents are evaporated to dryness and the expected compound is extracted with EtOAc (3 times) and dried over MgSO₄. After evaporation of the solvents, crude material is precipitated in ACN, affording after filtration, Compound (16) as a white solid (5 mg; 10%).

¹H NMR (DMSO-d₆, 300 MHz) δ 1.75 (m, 2H), 2.16 (s, 3H), 2.43 (s, 3H), 3.83 (m, 1H), 7.17 (d, J=3 Hz, 1H), 7.53 (d, J=3 Hz, 1H), 8.39 (d, J=9 Hz, 1H), 12.37 (m, 1H). M⁻ (ESI): 404.2; M⁺ (ESI): 406.2. HPLC (method A), Rt: 2.23 min (purity: 93.44%).

Example 17

N-(5-{5-[(2,3-dihydroxypropylamino)sulfonyl]-2-thienyl}-4-methyl-1,3-thiazol-2-yl)acetamide (17)

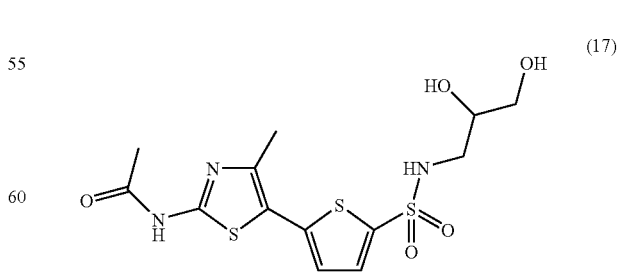

N-[5-(5-{[(2,2-dimethyl-1,3-dioxolan-4-yl)methyl]aminosulfonyl}-2-thienyl)-4-methyl-1,3-thiazol-2-yl]acetamide (14) (48 mg; 0.11 mmol; 1 eq), is dissolved in DCM (5 ml).

Trifluoroacetic acid (0.2 ml) is added and reaction mixture stirred at room temperature for 30 minutes. The solvents are evaporated and the crude product purified directly by preparative HPLC, affording Compound (17) as a white-off solid (7 mg; 16%). M⁻ (ESI): 390.2; M⁺ (ESI): 392.2. HPLC (method A), Rt: 2.13 min (purity: 83.5%).

Example 18

N-(5-{5-[(dimethylamino)sulfonyl]-2-thienyl}-4-methyl-1,3-thiazol-2-yl) acetamide (18)

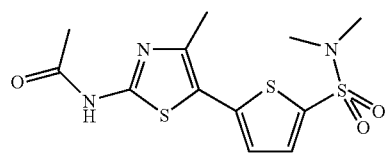

(18)

5-[2-(acetylamino)-4-methyl-1,3-thiazol-5-yl]thiophene-2-sulfonyl chloride, prepared as in Step II of Example 1 (110 mg; 0.33 mmol; 1 eq), is dissolved in DMF (10 ml). Dimethylamine (0.1 ml; 1.65 mmol; 5 eq) and DIEA (0.17 ml; 0.98 mmol; 3 eq) are added. After one hour, the solvents are evaporated to dryness. The crude product is re-dissolved in DCM and washed with NH₄Cl saturated solution, water and dried over MgSO₄. After evaporation of the solvents, crude material is precipitated in a mixture of DCM and diethyl ether, affording after filtration, Compound (18) as a yellow powder (52 mg; 46%).

¹H NMR (DMSO-d₆, 300 MHz) δ2.30 (s, 3H), 2.50 (s, 3H), 2.70 (s, 6H), 7.11 (d, J=3 Hz, 1H), 7.48 (d, J=3 Hz, 1H). M⁻ (ESI): 344.1; M⁺ (ESI): 346.1. HPLC (method A), Rt: 3.26 min (purity: 99.4%).

Example 19

N-{4-methyl-5-[5-({methyl[2-(methylamino)ethyl]amino}sulfonyl)-2-thienyl]-1,3-thiazol-2-yl}acetamide (19)

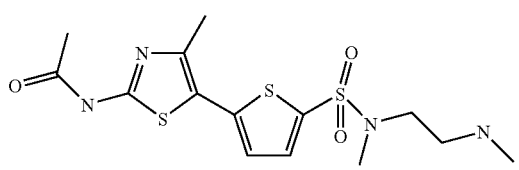

(19)

5-[2-(acetylamino)-4-methyl-1,3-thiazol-5-yl]thiophene-2-sulfonyl chloride, prepared as in Step II of Example 1 (500 mg; 1.48 mmol; 1.00 eq), is dissolved in DCM (30 ml). The solution is degassed with N₂ and cooled down to 0° C. Triethylamine (1 ml; 7.42 mmol; 5.00 eq) followed by N,N'-dimethylethylenediamine (0.79 ml; 7.42 mmol; 5.00 eq) are added. After 30 minutes at 0° C., the reaction is complete. The reaction mixture is washed with NaHCO₃ sat. (twice) and water (twice). The organic phase is dried over MgSO₄, filtered and concentrated under vacuum, affording Compound (19) as a beige solid (457 mg; 79%).

¹H NMR (DMSO-d₆, 300 MHz) δ 2.20 (s, 3H), 2.31 (s, 3H), 2.49 (s, 3H), 2.68 (t, 2H), 2.81 (s, 3H), 3.08 (t, 2H), 7.33 (d, 1H), 7.67 (d, 1H). M⁻ (ESI): 387.2; M⁺ (ESI): 389.3. HPLC (method A), Rt: 2.06 min (purity: 99.2%).

Example 20

N-[5-(5-{[[2-diethylamino)ethyl](methyl)amino]sulfonyl}-2-thienyl)-4-methyl-1,3-thiazol-2-yl]acetamide (20)

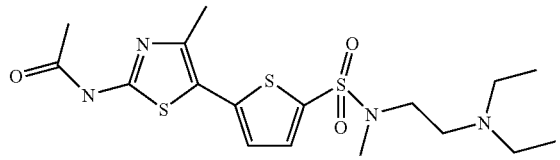

(20)

5-[2-(acetylamino)-4-methyl-1,3-thiazol-5-yl]thiophene-2-sulfonyl chloride, prepared as in Step II of Example 1 (500 mg; 1.48 mmol; 1.00 eq) is dissolved in DCM (30 ml). The solution is degassed with N₂ and cooled down to 0° C. Triethylamine (1.0 ml; 7.42 mmol; 5.00 eq) followed by N,N-diethyl-N'-methylethylenediamine (1.2 ml; 7.42 mmol; 5.00 eq) are added. After 1 hour at 0° C., the reaction is complete. The reaction mixture is washed with NaHCO₃ sat. (twice) and water (twice). The organic phase is dried over MgSO₄, filtered and concentrated under vacuum, affording Compound (20) as a beige solid (570 mg; 89%).

¹H NMR (DMSO-d₆, 300 MHz) δ 0.97 (t, 6H), 2.19 (s, 3H), 2.49 (m, 7H), 2.59 (t, 2H), 2.84 (s, 3H), 3.11 (t, 2H), 7.33 (d, 1H), 7.66 (d, 1H), 12.36 (s, 1H). M⁻ (ESI): 429.2; M⁺ (ESI): 431.3. HPLC (method A), Rt: 2.35 min (purity: 98.9%).

Example 21

N-[5-(5-{[(2-methoxyethyl)(methyl)amino]sulfonyl}-2-thienyl)-4-methyl-1,3-thiazol-2-yl]acetamide (21)

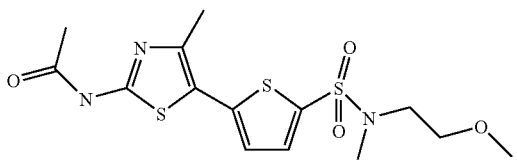

(21)

5-[2-(acetylamino)-4-methyl-1,3-thiazol-5-yl]thiophene-2-sulfonyl chloride, prepared as in Step II of Example 1 (500 mg; 1.48 mmol; 1.00 eq) in DCM (30 ml). The solution is degassed with N₂ and cooled down to 0° C. Triethylamine (1.0 ml; 7.42 mmol; 5.00 eq) followed by N-(2-methoxyethyl)methylamine (0.80 ml; 7.42 mmol; 5.00 eq) are added. After 45 minutes at 0° C., the reaction is complete. The reaction mixture is washed with NaHCO₃ sat. (twice) and water (twice). The organic phase is dried over MgSO₄, filtered and concentrated under vacuum, affording Compound (21) as a beige solid (478 mg; 83%).

¹H NMR (DMSO-d₆, 300 MHz) δ 2.19 (s, 3H), 2.49 (s, 3H), 2.83 (s, 3H), 3.23 (t, 2H), 3.28 (s, 3H), 3.53 (t, 2H), 7.33

(d, 1H), 7.66 (d, 1H), 12.38 (s, 1H). M⁻ (ESI): 388.2; M⁺ (ESI): 390.2. HPLC (method A), Rt: 3.27 min (purity: 99.9%).

Example 22

N-[5-(5-{[[2-dimethylamino)ethyl](ethyl)amino]sulfonyl}-2-thienyl)-4-methyl-1,3-thiazol-2-yl]acetamide (22)

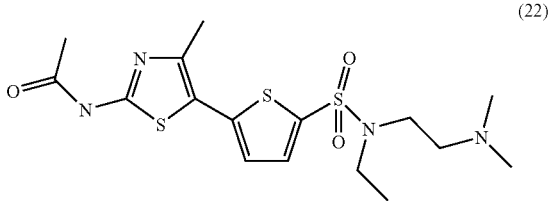

(22)

5-[2-(acetylamino)-4-methyl-1,3-thiazol-5-yl]thiophene-2-sulfonyl chloride, prepared as in Step II of Example 1 (500 mg; 1.48 mmol; 1.00 eq) in DCM (30 ml). The solution is degassed with $N_2$ and cooled down to 0° C. Triethylamine (1.0 ml; 7.42 mmol; 5.00 eq) followed by N,N-dimethyl-N'-ethylethylenediamine (1.2 ml; 7.42 mmol; 5.00 eq) are added. After 30 minutes at 0° C., the reaction is complete. The reaction mixture is washed with $NaHCO_3$ sat. (twice) and water (twice). The organic phase is dried over $MgSO_4$, filtered and concentrated under vacuum, affording Compound (22) as a beige solid (544 mg; 88%).

¹H NMR (DMSO-$d_6$, 300 MHz) δ 1.14 (t, 3H), 2.19 (m, 9H), 2.45 (t, 2H), 2.49 (s, 3H), 3.25 (m, 4H), 7.29 (d, 1H), 7.67 (d, 1H), 12.37 (s, 1H). M⁻ (ESI): 415.2; M⁺ (ESI): 417.3. HPLC (method A), Rt: 2.35 min (purity: 98.6%).

Example 23

N-{5-[5-{[2-(dimethylamino)ethyl]amino}sulfonyl)-3-thienyl]-4-methyl-1,3-thiazol-2-yl}acetamide, Trifluoroacetic Salt (23)

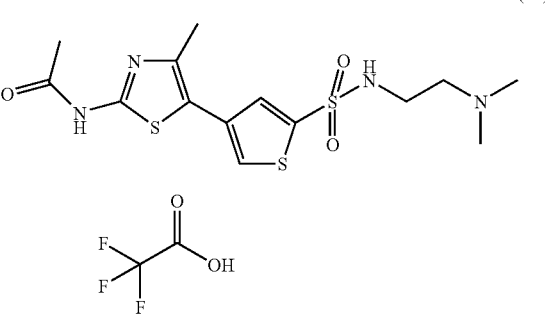

(23)

Step I: N-[4-methyl-5-(3-thienyl)-1,3-thiazol-2-yl]acetamide

In a microwave tube, N-(5-iodo-4-methyl-1,3-thiazol-2-yl)acetamide, Intermediate 1 (564.2 mg; 2 mmol; 1 eq) and Pd(dppf)Cl₂ (73.2 mg; 0.10 mmol; 0.05 eq) are suspended in Toluene (7 ml). A solution of potassium fluoride (464.8 mg; 8 mmol; 4 eq) in MeOH (7 ml) is added. 3-(4,4,5,5-Tetramethyl-1,3,2-dioxaborolan-2-yl)thiophene (630.3 mg; 3 mmol; 1.50 eq) is finally added as a solid. The resulting solution is flushed with argon, the tube is closed and heated under microwave action at 120° C. for 15 minutes. The reaction mixture is filtered over Celite and the solvents are evaporated. The resulting crude product is dissolved in EtOAc, washed with water and brine and dried over $MgSO_4$. It is then purified by preparative HPLC, affording the title compound as white-off solid (316.7 mg; 66% yield).

¹H NMR (DMSO-$d_6$, 300 MHz) δ 2.12 (s, 3H), 2.35 (s, 3H), 7.28 (dd, J=1.5, 4.9 Hz, 1H), 7.58 (dd, J=1.5, 3.0 Hz, 1H), 7.67 (dd, J=3.0, 4.9 Hz, 1H), 12.09 (s, 1H). M¹(ESI) 237.03; M⁺ (ESI): 239.03. HPLC (method A), Rt: 2.92 min (purity: 99.6%).

Step II: N-[5-(2-Bromo-thiophen-3-yl)-4-methyl-thiazol-2-yl]-acetamide

N-[4-methyl-5-(3-thienyl)-1,3-thiazol-2-yl]acetamide obtained in Step I as described above (3880 mg; 16.3 mmol; 1 eq) is dissolved in ACN (375 ml). N-bromosuccinimide (2898 mg; 16.3 mmol; 1 eq) is added and the resulting solution is stirred at room temperature for 30 minutes. Solvents are concentrated. Water is added and the desired product is extracted with EtOAc (3 times). Organic phases are washed with water (3 times) and dried over $MgSO_4$, affording the title compound (5000 mg; 97%).

¹H NMR (DMSO-$d_6$, 300 MHz) δ 2.06 (s, 3H), 2.13 (s, 3H), 7.11 (s, 1H), 7.70 (s, 1H), 12.13 (s, 1H). M⁻ (ESI): 317.2; M⁺ (ESI): 319.1. HPLC (method A), Rt: 1.27 min (purity: 80.7%).

Step III: 4-[2-(acetylamino)-4-methyl-1,3-thiazol-5-yl]-5-bromothiophene-2-sulfonyl chloride A mixture of N-[5-(2-bromo-thiophen-3-yl)-4-methyl-thiazol-2-yl]-acetamide obtained in Step II, as describe above (1100 mg; 3.47 mmol; 1 eq), in DCM (60 ml) is cooled to 0° C. with an ice bath. The reaction is degassed with nitrogen and chlorosulfonic acid (1.16 ml; 17.3 mmol; 5 eq) dissolved in DCM (30 ml) is added dropwise. The reaction mixture is stirred at 0° C. for 15 minutes. Phosphorus pentachloride (1444 mg; 6.94 mmol; 2 eq) is added followed directly by phosphorus oxide chloride (1.3 ml; 13.9 mmol; 4 eq). The reaction is stirred for an additional 2 hours at room temperature. Then the reaction mixture is poured into a beaker with crushed ice and directly transferred in a separated funnel. It is extracted with 2 portions EtOAc. The organic layer is dried over $MgSO_4$, affording the title compound (1440 mg; quantitative yield).

M⁻ (ESI): 415.1; M⁺ (ESI): 417.1. HPLC (method A), Rt: 3.94 min (purity: 95.5%).

Step IV: N-{5-[2-Bromo-5-(2-dimethylamino-ethyl-sutramoyl)-thiophen-3-yl]4-methyl-thiazol-2-yl}-acetamide 4-[2-(acetylamino)-4-methyl-1,3-thiazol-5-yl]-5-bromothiophene-2-sulfonyl chloride obtained in Step III as describe above (586 mg; 1.41 mmol; 1 eq), is dissolved in anhydrous DCM (15 ml). The reaction is put under nitrogen. Triethylamine (1.9 ml; 14.1 mmol; 10 eq) and N,N-dimethylethane-1,2-diamine (0.17 ml; 2.82 mmol; 2 eq) are added successively and the reaction mixture is stirred at room temperature for 30 minutes. The solvents are evaporated and the crude mixture is purified by preparative HPLC, affording the title compound (68 mg; 10%).

¹H NMR (DMSO-d₆, 300 MHz) δ 1.80 (s, 3H), 2 (s, 3H), 2.30 (s, 3H), 2.82 (m, J=21 Hz, 4H), 3.38 (d, J=3 Hz, 4H), 7.15 (d, J=6 Hz, 1H), 7.45 (d, J=3 Hz, 1H), 12.18 (s, 1H) M⁻ (ESI): 467.2; M⁺ (ESI): 469.2. HPLC (method A), Rt: 2.22 min (purity: 100%).

Step V: N-{5-[5-({[2-(dimethylamino)ethyl]amino}sulfonyl)-3-thienyl]4-methyl-1,3-thiazol-2-yl}acetamide, Trifluoroacetic Salt (23)

N-{5-[2-bromo-5-(2-dimethylamino-ethylsulfamoyl)-thiophen-3-yl]-4-methyl-thiazol-2-yl}-acetamide, (68 mg; 0.15 mmol; 1 eq) is dissolved in anhydrous THF (10 ml). The reaction mixture is cooled down to −70° C. and put under nitrogen. n-Butyllithium (0.73 ml; 1.6 M; 1.16 mmol; 8 eq) is added dropwise. After 15 minutes at −78° C., the reaction is complete. It is quenched with water. Solvents are evaporated and the crude product is purified by preparative HPLC, affording the trifluoroacetic salt of Compound (23) as white-off powder (34 mg; 46%).

¹H NMR (DMSO-d₆, 300 MHz) δ 2.14 (s, 3H), 2.37 (s, 3H), 2.79 (s, 6H), 3.20 (s, 4H), 7.74 (s, 1H), 7.99 (s, 1H), 8.24 (s, 1H), 9.42 (s, 1H), 12.17 (s, 1H). M⁻ (ESI): 387.3; M⁺ (ESI): 389.3. HPLC (method A), Rt: 1.80 min (purity: 100%).

Example 24

N-[4-methyl-5-(5-{[(2-morpholin-4-ylethyl)amino]sulfonyl}-3-thienyl)-1,3-thiazol-2-yl]acetamide, Trifluoroacetic Salt (24)

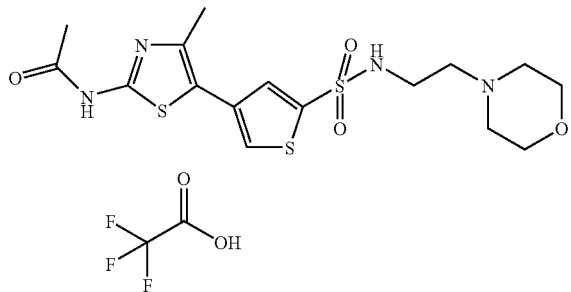

(24)

Step I: N-{5-[2-Bromo-5-(2-morpholin-4-yl-ethyl-sutramoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23, (586 mg; 1.41 mmol; 1 eq) is dissolved in anhydrous DCM (15 ml). The reaction is put under nitrogen. Then triethylamine (1.96 ml; 14.1 mmol; 10 eq) and 2-morpholin-4-yl-ethylamine (367 mg; 2.82 mmol; 2 eq) are added successively and the reaction mixture is stirred at room temperature for 30 minutes. Solvents are evaporated and the resulting crude product is purified by preparative HPLC, affording the title compound (100 mg; 14%).

M⁻ (ESI): 509.4; M⁺ (ESI): 511.3. HPLC (method A), Rt: 2.25 min (purity: 99.3%).

Step II: N-[4-methyl-5-(5-{[(2-morpholin-4-ylethyl)amino]sulfonyl}-3-thienyl)-1,3-thiazol-2-yl]acetamide, Trifluoroacetic Salt (24)

N-{5-[2-Bromo-5-(2-morpholin-4-yl-ethylsulfamoyl)-thiophen-2-yl]-4-methyl-thiazol-2-yl}-acetamide obtained in Step I as described above (100 mg; 0.2 mmol; 1 eq), is dissolved in anhydrous TBF (12 ml). The reaction mixture is cooled down to −70° C. and put under nitrogen. n-Butyllithium (0.98 ml; 1.6 M; 1.57 mmol; 8 eq) is added dropwise. After 15 minutes the reaction is complete and quenched with water. Solvents are evaporated and the crude product is purified by preparative HPLC, affording the trifluoroacetic salt of Compound (24) as a white-off solid (44 mg; 40%).

¹H NMR (DMSO-d₆, 300 MHz) δ 2.14 (s, 1H), 2.37 (s, 3H), 3.94-3.12 (m, 12H), 7.74 (s, 1H), 7.99 (s, 1H), 8.26 (s, 1H), 9.72 (s, 1H), 12.17 (s, 1H) M⁻ (ESI): 429.3; M⁺ (ESI): 431.3. HPLC (method A), Rt: 1.86 min (purity: 98.47%).

Example 25

N-[4-methyl-5-(5-{[(2-piperidin-1-ylethyl)amino]sulfonyl}-3-thienyl)-1,3-thiazol-2-yl]acetamide, Trifluoroacetic Salt (25)

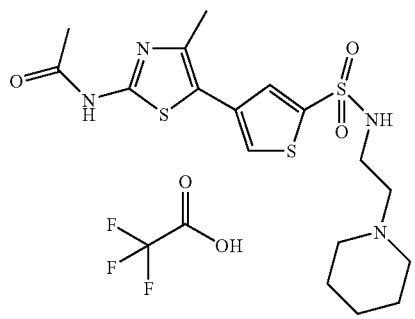

(25)

Step I: N-{5-[2-Bromo-5-(2-piperidin-1-yl-ethylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (200 mg; 0.48 mmol; 1 eq), is dissolved in anhydrous DCM (10 ml). The reaction mixture is cooled down to 0° C. and put under nitrogen. Triethylamine (0.4 ml; 2.88 mmol; 6 eq) and 2-piperidin-1-yl-ethylamine (0.16 ml; 1.16 mmol; 2.4 eq) are added successively and the reaction mixture is stirred at 0° C. for 2 hours. The mixture is washed with water, NaHCO₃ and dried over MgSO₄, affording the title compound (170 mg; 68%).

¹H NMR (DMSO-d₆, 300 MHz) δ 1.80 (s, 3H), 2 (s, 3H), 2.30 (s, 3H), 2.82 (m, J=21 Hz, 4H), 3.38 (d, J=3 Hz, 4H), 7.15 (d, J=6 Hz, 1H), 7.45 (d, J=3 Hz, 1H), 12.18 (s, 1H) M⁻ (ESI): 401.2; M⁺ (ESI): 403.3. HPLC (method A), Rt: 2.10 min (purity: 94.4%).

Step II: N-[4-methyl-5-(5-{[(2-piperidin-1-ylethyl)amino]sulfonyl}-3-thienyl)-1,3-thiazol-2-yl]acetamide, Trifluoroacetic Salt (25)

N-{5-[2-Bromo-5-(2-piperidin-1-yl-ethylsulfamoyl)-thiophen-3-yl]-4-methyl-thiazol-2-yl}-acetamide obtained in Step I as described above (170 mg; 0.33 mmol; 1 eq), is dissolved in anhydrous THF (50 ml). The reaction mixture is cooled down to −70° C. and put under nitrogen. n-Butyllithium (1.67 ml; 1.6 M; 2.68 mmol; 8 eq) is added dropwise. After 30 minutes the reaction is complete and quenched with water. Solvents are evaporated and the resulting crude mixture is purified by preparative HPLC, affording the trifluoroacetic salt of Compound (25) as white-off solid (10 mg; 5%).

$^1$H NMR (DMSO-$d_6$, 300 MHz) δ 1.64-1.77 (m, 6H), 2.14 (s, 3H), 2.38 (s, 3H), 2.88-2.92 (q, 2H), 3.17-3.25 (m, 4H), 3.42-3.46 (d, J=6 Hz, 2H), 7.73 (s, 1H), 7.99 (s, 1H), 8.24 (s, 1H), 9.08 (s, 1H), 12.17 (s, 1H) M$^-$ (ESI): 427.4; M$^+$ (ESI): 429.5. HPLC (method A), Rt: 2.11 min (purity: 93.5%).

Example 26

N-{4-methyl-5-[5-(piperazin-1-ylsulfonyl)-3-thienyl]-1,3-thiazol-2-yl}acetamide, Trifluoroacetic Salt (26)

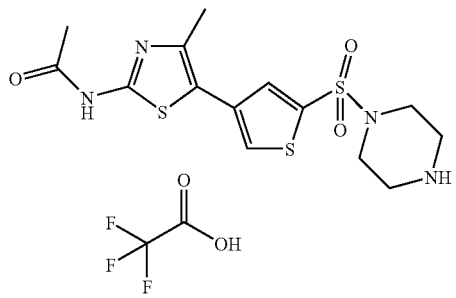

(26)

Step I: 4-[4-(2-Acetylamino-4-methyl-thiazol-5-yl)-5-bromo-thiophene-2-sulfonyl]-piperazine-1-carboxylic Acid Tert-Butyl Ester 4-[2-(acetylamino)-4-methyl-1,3-thiazol-5-yl]-5-bromothiophene-2-sulfonyl chloride, prepared as in Step III of Example 23 (400 mg; 0.96 mmol; 1 eq), is dissolved in anhydrous DCM (20 ml). The solution is cooled down to 0° C. and put under nitrogen. Triethylamine (0.54 ml; 1.92 mmol; 4 eq) and 1-Boc-piperazine (358.4 mg; 1.92 mmol; 2 eq) are added successively and the reaction mixture is stirred at 0° C. for 1 hour. The reaction mixture is washed with water, NaHCO$_3$ and dried over MgSO$_4$, affording the title compound (440 mg; 76%).

M$^-$ (ESI): 565.3; M$^+$ (ESI): 567.2. HPLC (method A), Rt: 4.16 min (purity: 93.91%).

Step II: N-{4-methyl-5-[5-(piperazin-1-ylsulfonyl)-3-thienyl]-1,3-thiazol-2-yl}acetamide, Trifluoroacetic Salt (26)

4-[4-(2-Acetylamino-4-methyl-thiazol-5-yl)-5-bromothiophene-2-sulfonyl]-piperazine-1-caboxylic acid tert-butyl ester obtained in Step I as described above (440 mg; 0.78 mmol; 1 eq), is dissolved in anhydrous TBF (50 ml). The reaction mixture is cooled down to −70° C. and put under nitrogen. n-Butyllithium (3.9 ml; 1.6 M; 6.22 mmol; 8 eq) is added dropwise. After 1 hour the reaction is complete and quenched with water. Solvents are evaporated and the crude product is purified by preparative HPLC. After evaporation of the fractions in the presence of TFA, the cleavage of Boc protecting group is observed. The isolated product is suspended in ether, affording the trifluoroacetic salt of Compound (26) as white-off solid (25 mg; 6%).

$^1$H NMR (DMSO-$d_6$, 300 MHz) δ 2.15 (s, 3H), 2.40 (s, 3H), 3.11 (s, 8H), 7.85 (s, 1H), 8.15 (s, 1H), 8.61 (s, 1H), 12.20 (s, 1H). M$^-$ (ESI): 385.3; M$^+$ (ESI): 387.3. HPLC (method A), Rt: 1.98 min (purity: 100%).

Example 27

N-{5-[5-({[3-(dimethylamino)propyl]amino}sulfonyl)-3-thienyl]-4-methyl-1,3-thiazol-2-yl}acetamide (27)

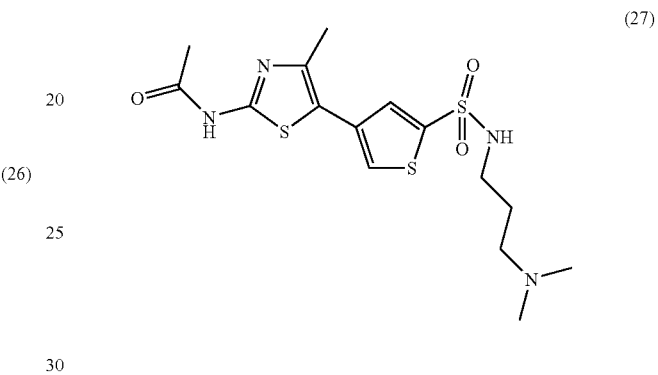

(27)

Step I: N-{5-[2-Bromo-5-(3-dimethylamino-propyl-sulfamoyl)-thiophen-3-yl]4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (200 mg; 0.48 mmol; 1 eq), is dissolved in anhydrous DCM (10 ml). The reaction mixture is cooled down to 0° C. and put under nitrogen. Triethylamine (0.33 ml; 2.41 mmol; 5 eq) and N,N-dimethyl-1,3-propanediamine (0.3 ml; 2.41 mmol; 5 eq) are added successively and the reaction mixture is stirred at 0° C. for 1 hour. It is then washed with water, NaHCO$_3$ and dried over MgSO$_4$, affording the title compound (200 mg; 86%).

M$^-$ (ESI): 481.3; M$^+$ (ESI): 483.3. HPLC (method A), Rt: 2.30 min (purity: 100%).

Step II: N-{5-[5-({[3-(dimethylamino)propyl]amino}sulfonyl)-3-thienyl]4-methyl-1,3-thiazol-2-yl}acetamide (27)

N-{5-[2-Bromo-5-(3-dimethylamino-propylsulfamoyl)-thiophen-3-yl]-4-methyl-thiazol-2-yl}-acetamide obtained in Step I as described above (200 mg; 0.42 mmol; 1 eq), is dissolved in anhydrous TBF (50 ml). The reaction mixture is cooled to down to −70° C. and put under nitrogen. n-Butyllithium (2.1 ml; 1.6 M; 3.32 mmol; 8 eq) is added dropwise. After 2 h30, the reaction is complete and is quenched with water. Solvents are evaporated and the resulting mixture is purified by preparative HPLC affording Compound (27) as a brown oil (120 mg; 68%).

$^1$H NMR (DMSO-$d_6$, 300 MHz) δ 2.13 (s, 3H), 2.37 (s, 3H), 2.72 (d, J=3 Hz, 6H), 3.46-3.58 (m, 6H), 7.68 (s, 1H), 7.95 (s, 1H), 8.05-8.09 (t, J=6 Hz, 1H), 9.90 (s, 1H), 12.16 (s, 1H) M$^-$ (ESI): 401.3; M$^+$ (ESI): 403.3. HPLC (method A), Rt: 1.88 min (purity: 94.3%).

Example 28

N-[4-methyl-5-(5-{[(1-methylpiperidin-4-yl)amino]sulfonyl}-3-thienyl]-1,3-thiazol-2-yl]acetamide, Hydrochloride Salt (28)

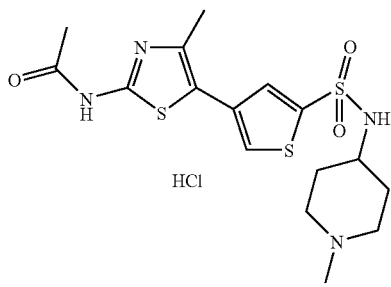

Step I: N-{5-[2-Bromo-5-(1-methyl-piperidin-4-ylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (200 mg; 0.48 mmol; 1 eq), is dissolved in anhydrous DCM (10 ml). The reaction mixture is cooled down to 0° C. and put under nitrogen. Triethylamine (0.27 ml; 1.92 mmol; 4 eq) and 1-methyl-piperidin-4-ylamine (0.11 ml; 0.96 mmol; 2 eq) are added successively and the reaction mixture is stirred at 0° C. for 40 minutes. It is then washed with water, NaHCO$_3$ and dried over MgSO$_4$, affording the title compound (185 mg; 74%).

M$^-$ (ESI): 493.2; M$^+$ (ESI): 495.3. HPLC (method A), Rt: 2.32 min (purity: 95.5%).

Step II: N-[4-methyl-5-(5-{[(1-methylpiperidin-4-yl)amino]sulfonyl}-3-thienyl]-1,3-thiazol-2-yl]acetamide, Hydrochloride Salt (28)

N-{5-[2-Bromo-5-(1-methyl-piperidin-4-ylsulfamoyl)-thiophen-3-yl]-4-methyl-thiazol-2-yl}-acetamide obtained in Step I as described above (185 mg; 0.37 mmol; 1 eq), is dissolved in anhydrous TBF (50 ml). The reaction mixture is cooled down to −70° C. and put under nitrogen. n-Butyl-lithium (1.87 ml; 1.6 M; 3 mmol; 8 eq) is added dropwise. After 2 h30 the reaction is complete and quenched with water. Solvents are evaporated and the resulting crude product is purified by preparative HPLC. The fractions containing the pure desired product are concentrated, neutralized with NaHCO$_3$ and extracted with EtOAc. Organic phase is dried over MgSO$_4$ and evaporated. The resulting product (59.7 mg) is dissolved in MeOH and HCl 1.25M solution in MeOH is added (115 µl). After evaporation of the solvents, the hydrochloride salt of Compound (28) is isolated as beige solid (65 mg; 37%).

$^1$H NMR (DMSO-d$_6$, 300 MHz) δ 1.75-1.80 (m, 5H), 2.15 (s, 3H), 2.38 (s, 3H), 2.61 (d, 3H), 2.90-3.40 (m, 4H), 7.70 (s, 1H), 7.95 (s, 1H), 8.35 (d, 1H), 12.25 (s, 1H). M$^-$ (ESI): 413.3; M$^+$ (ESI): 415.4. HPLC (method A), Rt: 1.89 min (purity: 95.5%).

Example 29

N-(4-methyl-5-{5-[(4-methylpiperazin-1-yl)sulfonyl]-3-thienyl}-1,3-thiazol-2-yl)acetamide (29)

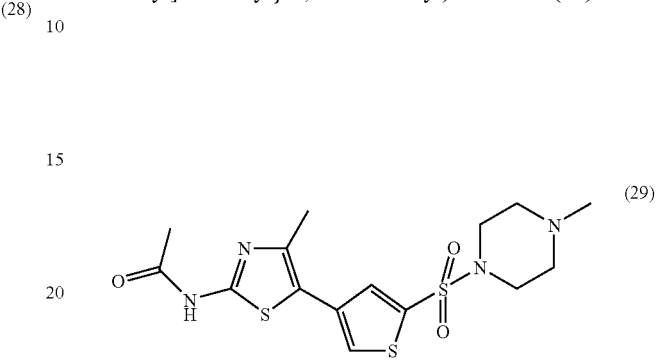

Step I: N-{5-[2-Bromo-5-(4-methyl-piperazine-1-sulfonyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (4200 mg; 10.1 mmol; 1 eq), is dissolved in anhydrous DCM (200 ml). The reaction is put under nitrogen. Triethylamine (7.0 ml; 50.5 mmol; 5 eq) and 1-methylpiperazine (5.61 ml; 50.5 mmol; 5 eq) are added successively and the reaction mixture is stirred for 3 hours at room temperature. It is washed with water, NH$_4$Cl sat, brine and dried over MgSO$_4$, affording the title compound (4200 mg; 87%).

M$^-$ (ESI): 479.3; M$^+$ (ESI): 481.3. HPLC (method A), Rt: 2.38 min (purity: 91.3%).

Step II: N-(4-methyl-5-{5-[(4-methylpiperazin-1-yl)sulfonyl]-3-thienyl}-1,3-thiazol-2-yl)acetamide (29)

N-{5-[2-Bromo-5-(4-methyl-piperazine-1-sulfonyl)-thiophen-3-yl]-4-methyl-thiazol-2-yl}-acetamide obtained in Step I as described above (400 mg; 0.83 mmol; 1 eq), is dissolved in anhydrous TBF (50 ml). The reaction mixture is cooled down to −70° C. and put under nitrogen. n-Butyl-lithium (4.2 ml; 1.6 M; 6.67 mmol; 8 eq) is added dropwise. After 1 hour the reaction is complete and quenched with water. Solvents are evaporated and the crude product is dissolved in EtOAc. The resulting organic phase is washed with water (2 times), brine and dried over MgSO$_4$. After evaporation of the solvents, the resulting product is precipitated in an ether/DCM mixture, affording Compound (29) as a white-off solid (125 mg; 37%).

$^1$H NMR (DMSO-d$_6$, 300 MHz) δ 2.20 (s, 3H), 2.40 (s, 3H), 2.55 (s, 3H), 3.35 (s, 8H), 7.75 (s, 1H), 8.10 (s, 1H), 12.20 (s, 1H). M$^-$ (ESI): 399.3; M$^+$ (ESI): 401.3. HPLC (method A), Rt: 1.99 min (purity: 98.8%).

Example 30 tert-butyl[1-({4-[2-(acetylamino)-4-methyl-1,3-thiazol-5-yl]-2-thienyl}sulfonyl)piperidin-4-yl]methylcarbamate (30)

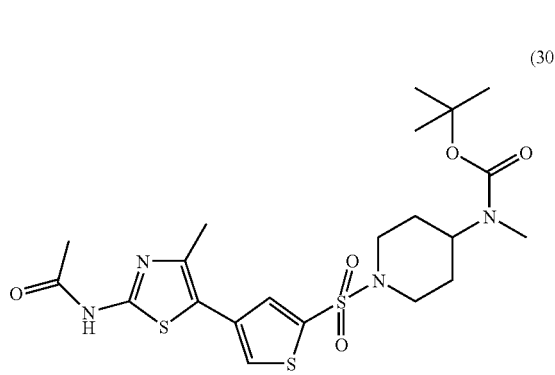

Step I: {1-[4-(2-Acetylamino-4-methyl-thiazol-5-yl)-5-bromo-thiophene-2-sulfonyl]-piperidin-4-yl}-methyl-carbamic Acid Tert-Butyl Ester 4-[2-(acetylamino)-4-methyl-1,3-thiazol-5-yl]-5-bromothiophene-2-sulfonyl chloride, prepared as in Step III of Example 23 (300 mg; 0.72 mmol; 1 eq), is dissolved in anhydrous DCM (20 ml). The reaction mixture is put under nitrogen. Triethylamine (0.5 ml; 3.61 mmol; 5 eq) and methyl-piperidine-4-yl-carbamic acid tert-butyl ester (773.2 mg; 3.61 mmol; 5 eq) are added successively and the reaction mixture is stirred for 30 minutes at room temperature. It is then washed with water, NaHCO$_3$ sat., brine and dried over MgSO$_4$, affording the title compound (470 mg; quantitative).

M$^-$ (ESI): 593.5; M$^+$ (ESI): 595.3. HPLC (method A), Rt: 4.41 min (purity: 91%).

Step II: Tert-butyl[1-({4-[2-(acetylamino)-4-methyl-1,3-thiazol-5-yl]-2-thienyl}sulfonyl)piperidin-4-yl]methylcarbamate (30)

{1-[4-(2-Acetylamino-4-methyl-thiazol-5-yl)-5-bromo-thiophene-2-sulfonyl]-piperidin-4-yl}-methyl-carbamic acid tert-butyl ester obtained in Step I as described above (470 mg; 0.79 mmol; 1 eq), is dissolved in anhydrous THF (20 ml). The reaction mixture is cooled down to −70° C. and put under nitrogen. n-Butyllithium (5 ml; 1.6 M; 7.92 mmol; 8 eq) is added dropwise. After 30 minutes the reaction is complete and quenched with water. Solvents are evaporated and EtOAc is added. The resulting solution is washed with water (2 times), brine and dried over MgSO$_4$. After evaporation of the solvents, the crude product is suspended in ether at 4° C. for 2 hours. It is then filtered, affording Compound (30) as a brown solid (348 mg; 71%).

M$^-$ (ESI): 513.4; M$^+$ (ESI): 515.35. HPLC (method A), Rt: 4 min (purity: 82.7%).

Example 31

N-(5-{5-[(3-hydroxypyrrolidin-1-yl)sulfonyl]-3-thienyl}-4-methyl-1,3-thiazol-2-yl)acetamide, trifluoroacetic salt (31)

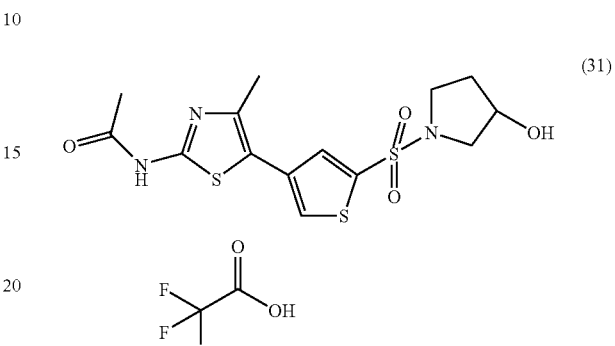

Step I: N-{5-[2-Bromo-5-(3-hydroxy-pyrrolidine-1-sulfonyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (300 mg; 0.72 mmol; 1 eq), is dissolved in anhydrous DCM (20 ml). The solution is put under nitrogen. Triethylamine (0.5 ml; 3.61 mmol; 5 eq) and 3-pyrrolidinol (0.3 ml; 3.61 mmol; 5 eq) are added successively. DMF (0.2 ml) is added and the reaction mixture is stirred for 1 hour at room temperature. It is then washed with water, NaHCO$_3$ sat., brine and dried over MgSO$_4$, affording the title compound (310 mg; 83%).

M$^-$ (ESI): 466.1; M$^+$ (ESI): 468.1. HPLC (method A), Rt: 2.91 min (purity: 91.8%).

Step II: N-(5-{5-[(3-hydroxypyrrolidin-1-yl)sutronyl]-3-thienyl}4-methyl-1,3-thiazol-2-yl)acetamide, Trifluoroacetic Salt (31)

N-{5-[2-Bromo-5-(3-hydroxy-pyrrolidine-1-sulfonyl)-thiophen-3-yl]-4-methyl-thiazol-2-yl}-acetamide obtained in Step I as described above (310 mg; 0.52 mmol; 1 eq), is dissolved in anhydrous THF (20 ml). The reaction mixture is cooled to down to −70° C. and put under nitrogen. n-Butyllithium (2 ml; 1.6 M; 3.13 mmol; 8 eq) is added dropwise. After 5 hours the reaction is complete and quenched with water. Solvents are evaporated and the resulting crude product is purified by preparative HPLC, affording the trifluoroacetic salt of Compound (31) as a brown solid (132 mg; 50%).

$^1$H NMR (DMSO-d$_6$, 300 MHz) δ 1.63-1.85 (m, 2H), 2.13 (s, 3H), 2.36 (s, 3H), 3.07-3.11 (d, J=12 Hz, 1H), 3.28-3.36 (m, 4H), 4.20 (m, 4H), 7.71 (s, 1H), 7.98 (s, 1H), 12.14 (s, 1H). M$^-$ (ESI): 386.2; M$^+$ (ESI): 388.2. HPLC (method A), Rt: 2.50 min (purity: 99.4%).

Example 32

N-[5-(5-{[(3-hydroxypropyl)amino]sulfonyl}-3-thienyl)-4-methyl-1,3-thiazol-2-yl]acetamide (32)

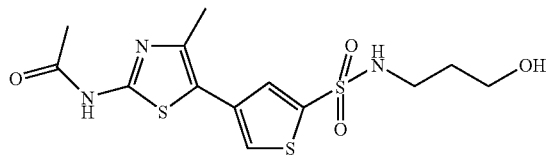

(32)

Step I: N-{5-[2-Bromo-5-(3-hydroxy-propylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (300 mg; 0.72 mmol; 1 eq), is dissolved in anhydrous DCM (20 ml). The reaction is put under nitrogen. Triethylamine (0.5 ml; 3.61 mmol; 5 eq) and 3-amino-1-propanol (0.27 ml; 3.61 mmol; 5 eq) are added successively and the reaction mixture is stirred for 1 hour at room temperature. It is washed with water, NaHCO$_3$ sat., brine and dried over MgSO$_4$, affording the title compound (230 mg; 70%).

M$^-$ (ESI): 454.2; M$^+$ (ESI): 456.2. HPLC (method A), Rt: 2.71 min (purity: 98.7%).

Step II: N-[5-(5-{[(3-hydroxypropyl)amino]sulfonyl}-3-thienyl)-4-methyl-1,3-thiazol-2-yl]acetamide (32)

N-{5-[2-Bromo-5-(3-hydroxy-propylsulfamoyl)-thiophen-3-yl]-4-methyl-thiazol-2-yl}-acetamide obtained in Step I as described above (230 mg; 0.51 mmol; 1 eq), is dissolved in anhydrous TBF (20 ml). The reaction mixture is cooled down to −70° C. and put under nitrogen. n-Butyllithium (1.9 ml; 1.6 M; 3.04 mmol; 8 eq) is added dropwise. After 4 hours the reaction is quenched with water. Solvents are evaporated and the resulting crude product is purified by preparative HPLC, affording Compound (32) as a white-off powder (80.2 mg; 32%).

$^1$H NMR (DMSO-d$_6$, 300 MHz) δ 1.49-1.60 (m, 2H), 2.36 (s, 3H), 2.48 (s, 3H), 2.89-2.95 (q, J=6 Hz, 2H), 3.36-3.40 (t, J=6 Hz, 2H), 7.63 (s, 1H), 7.79-7.83 (t, J=6 Hz, 1H), 7.92 (s, 1H), 12.15 (s, 1H). M$^-$ (ESI): 374.2; M$^+$ (ESI): 376.2. HPLC (method A), Rt: 2.22 min (purity: 99.7%).

Example 33

N-[5-(5-{[(cis-4-hydroxycyclohexyl)amino]sulfonyl}-3-thienyl)-4-methyl-1,3-thiazol-2-yl]acetamide (33)

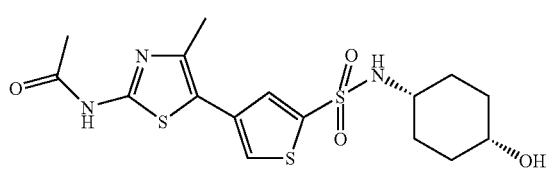

(33)

Step I: N-{5-[2-Bromo-5-(4-hydroxy-cyclohexylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (300 mg; 0.72 mmol; 1 eq), is dissolved in anhydrous DCM (20 ml). The reaction is put under nitrogen. Triethylamine (0.7 ml; 5.05 mmol; 7 eq) and trans-4-aminocyclohexanol hydrochloride (547.1 mg; 3.61 mmol; 5 eq) are added successively. DMF (0.2 ml) is added to dissolve the amine and the reaction mixture is stirred overnight at room temperature. The reaction mixture is then washed with water, NH$_4$Cl sat., brine and dried over MgSO$_4$, affording the title compound (120 mg; 21%).

M$^-$ (ESI): 493.04; M$^+$ (ESI):495.03. HPLC (method A), Rt: 2.98 min (purity: 62.8%).

Step II: N-[5-(5-{[(cis-4-hydroxycyclohexyl)amino]sulfonyl}-3-thienyl)-4-methyl-1,3-thiazol-2-yl]acetamide (33)

N-{5-[2-Bromo-5-(4-hydroxy-cyclohexylsulfamoyl)-thiophen-3-yl]-4-methyl-thiazo-2-yl}-acetamide obtained in Step I as described above (120 mg; 0.24 mmol; 1 eq), is dissolved anhydrous TBF (10 ml). The reaction mixture is cooled down to −70° C. and put under nitrogen. n-Butyllithium (1.5 ml; 1.6 M; 2.43 mmol; 8 eq) is added dropwise. The reaction is stirred overnight and quenched with water. Solvents are evaporated and the resulting crude product is purified by preparative HPLC, affording Compound (33) as white-off powder (28 mg; 21%).

$^1$H NMR (DMSO-d$_6$, 300 MHz) δ 1.05-1.26 (m, 4H), 1.63-1.74 (m, 4H), 2.13 (s, 3H), 2.36 (s, 3H), 3.04 (m, 1H), 3.29 (m, 1H), 7.66 (s, 1H), 7.88-7.90 (t, J=3 Hz, 2H), 12.15 (s, 1H). M$^-$ (ESI): 414.3; M$^+$ (ESI): 416.3. HPLC (method A), Rt: 2.42 min (purity: 95%).

Example 34

N-(5-{5-[(4-methoxypiperidin-1-yl)sulfonyl]-3-thienyl}-4-methyl-1,3-thiazol-2-yl)acetamide (34)

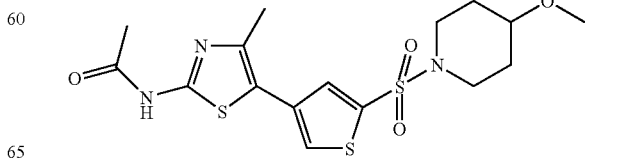

(34)

Step I: N-{5-[2-Bromo-5-(4-methoxy-piperidine-1-sutronyl)-thiophen-3-yl]4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (300 mg; 0.72 mmol; 1 eq), is dissolved in anhydrous DCM (20 ml). The reaction is put under nitrogen. Triethylamine (0.5 ml; 3.61 mmol; 5 eq) and 4-methoxy-piperidine hydrochloride (314.3 mg; 3.61 mmol; 5 eq) are added successively and the reaction mixture is stirred for 30 minutes at room temperature. It is then washed with water, $NH_4Cl$ sat., brine and dried over $MgSO_4$, affording the title compound (250 mg; 60%).

M⁻ (ESI): 494.15; M⁺ (ESI): 495.5. HPLC (method A), Rt: 2.98 min (purity: 62.8%).

Step II: N-(5-{5-[(4-methoxypiperidin-1-yl)sutronyl]-3-thienyl}-4-methyl-1,3-thiazol-2-yl)acetamide (34)

N-{5-[2-Bromo-5-(4-methoxy-piperidine-1-sulfonyl)-thiophen-3-yl]-4-methyl-thiazol-2-yl}-acetamide obtained in Step I as described above (250 mg; 0.51 mmol; 1 eq), is dissolved in anhydrous TBF (20 ml). The reaction mixture is cooled down to −70° C. and put under nitrogen. n-Butyl-lithium (2 ml; 1.6 M; 4.04 mmol; 8 eq) is added dropwise. The reaction is stirred 40 minutes and quenched with water. Solvents are evaporated and the resulting crude product is purified by preparative HPLC, affording Compound (34) as a white-off powder (127 mg; 47%).

¹H NMR (DMSO-$d_6$, 300 MHz) δ 1.52-1.62 (m, 2H), 1.82-1.89 (m, 2H), 2.13 (s, 3H), 2.37 (s, 3H), 2.90-2.94 (m, 2H), 3.13-3.17 (m, 2H), 3.17 (s, 3H), 3.26-3.29 (m, 1H), 7.68 (s, 1H), 8.02 (s, 1H), 12.15 (s, 1H). M⁻ (ESI): 414.3; M⁺ (ESI): 416.3. HPLC (method A), Rt: 3.21 min (purity: 99.17%).

Example 35

N-[4-methyl-5-(5-{[4-(methylamino)piperidin-1-yl]sulfonyl}-3-thienyl)-1,3-thiazol-2-yl]acetamide, trifluoroacetic salt (35)

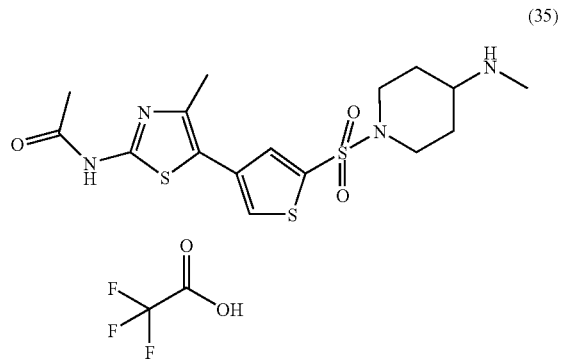

tert-butyl[1-({4-[2-(acetylamino)-4-methyl-1,3-thiazol-5-yl]-2-thienyl}sulfonyl)piperidin-4-yl]methylcarbamate (30), (300 mg; 0.58 mmol; 1 eq), is dissolved in anhydrous DCM (25 ml). Trifluoroacetic acid (2.2 ml) is added and the reaction is stirred overnight. The reaction mixture is then washed with water, brine and dried over $MgSO_4$. After evaporation of the solvents, the crude product is purified by preparative HPLC, affording the trifluoroacetic salt of Compound (35) as a yellow solid (68 mg; 21%).

¹H NMR (DMSO-$d_6$, 300 MHz) δ 1.51-1.62 (m, 2H), 1.92-2.10 (m, 2H), 2.14 (s, 1H), 2.37 (s, 3H), 2.46-2.58 (m, 4H), 3.07-3.11 (m, 1H), 3.71-3.75 (m, 3H), 7.70 (s, 1H), 8.06 (s, 1H), 8.63 (s, 1H), 12.16 (s, 1H). M⁻ (ESI): 413.3; M⁺ (ESI): 415.3. HPLC (method A), Rt: 2.01 min (purity: 95%).

Example 36

N-[5-(5-{[[2-(dimethylamino)ethyl](methyl)amino]sulfonyl}-3-thienyl)-4-methyl-1,3-thiazol-2-yl]acetamide (36)

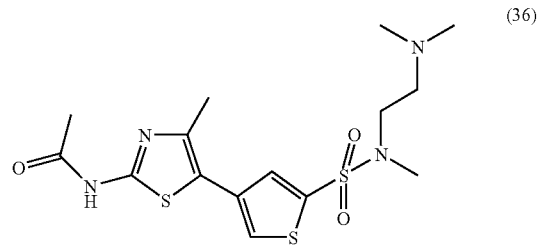

Step I: N-(5-{2-Bromo-5-[(2-dimethylamino-ethyl)-methyl-sulfamoyl]-thiophen-3-yl}-4-methyl-thiazol-2-yl)-acetamide 4-[2-(acetylamino)-4-methyl-1,3-thiazol-5-yl]-5-bromothiophene-2-sulfonyl chloride, prepared as in Step III of Example 23 (800 mg; 1.92 mmol; 1 eq), is dissolved in anhydrous DCM (50 ml). The reaction is put under nitrogen. Triethylamine (0.8 ml; 5.77 mmol; 3 eq) and N,N,N-trimethylenediamine (0.75 ml; 5.77 mmol; 3 eq) are added successively and the reaction mixture is stirred for 30 minutes at room temperature. It is washed with water, $NaHCO_3$ sat., brine and dried over $MgSO_4$, affording the title compound (730 mg; 76%).

M⁻ (ESI): 481.2; M⁺ (ESI): 483.2. HPLC (method A), Rt: 2.40 min (purity: 96.88%).

Step II: N-[5-(5-{[[2-(dimethylamino)ethyl](methyl)amino]sulfonyl}-3-thienyl)-4-methyl-1,3-thiazol-2-yl]acetamide (36)

N-(5-{2-Bromo-5-[(2-dimethylamino-ethyl)-methyl-sulfamoyl]-thiophen-3-yl}-4-methyl-thiazol-2-yl)-acetamide obtained in Step I as described above (750 mg; 1.56 mmol; 1 eq), is dissolved in anhydrous THF (60 ml). The reaction mixture is cooled down to −70° C. and put under nitrogen. n-Butyllithium (6.2 ml; 1.6 M; 12.5 mmol; 8 eq) is added dropwise. The reaction is stirred 1 hour and is quenched with water. Solvents are evaporated and the resulting residue is dissolved in EtOAc, washed with water (2 times), brine and dried over $MgSO_4$. After evaporation of the solvent, the resulting product is suspended in a mixture of ether-DCM and filtered, affording Compound (36) as a brown solid (582 mg; 87%).

¹H NMR (DMSO-$d_6$, 300 MHz) δ 2.14 (s, 3H), 2 (s, 3H), 2.38 (s, 3H), 2.79 (s, 3H), 2.84 (s, 13H), 7.82 (s, 1H), 8.08 (s, 1H), 9.41 (s, 1H), 12.16 (s, 1H). M⁻ (ESI): 401.3; M⁺ (ESI): 403.3. HPLC (method A), Rt: 1.98 min (purity: 93.6%).

Example 37

N-[5-(5-{[(1S,5S,7S)-7-(hydroxymethyl)-6,8-dioxa-3-azabicyclo[3.2.1]oct-3-yl]sulfonyl}-3-thienyl)-4-methyl-1,3-thiazol-2-yl]acetamide (37)

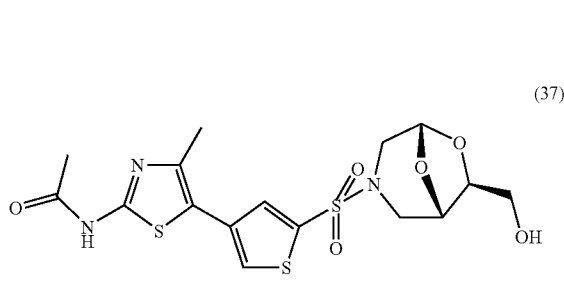

(37)

Step I: N-{5-[2-Bromo-5-(7-hydroxymethyl-6,8-dioxa-3-aza-bicyclo[3.2.1]octane-3-sulfonyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (400 mg; 0.96 mmol; 1 eq), is dissolved in anhydrous DCM (40 ml). The reaction is put under nitrogen. Triethylamine (0.67 ml; 4.81 mmol; 3 eq) and (6,8-Dioxa-3-aza-bicyclo[3.2.1]oct-7-yl)-methanol (349.2 mg; 2.41 mmol; 2.5 eq) are added successively and the reaction mixture is stirred overnight at room temperature. It is then washed with water, $NH_4Cl$ sat., brine and dried over $MgSO_4$, affording the title compound (450 mg; 77%).

M$^-$ (ESI): 524.2; M$^+$ (ESI): 526.2. HPLC (method A), Rt: 2.94 min (purity: 86.8%).

Step II. N-[5-(5-{[(1S,5S,7S)-7-(hydroxymethyl)-6,8-dioxa-3-azabicyclo[3.2.1]oct-3-yl]sulfonyl}-3-thienyl)-4-methyl-1,3-thiazol-2-yl]acetamide (37)

N-{5-[2-Bromo-5-(7-hydroxymethyl-6,8-dioxa-3-aza-bicyclo[3.2.1]octane-3-sulfonyl)-thiophen-3-yl]-4-methyl-thiazol-2-yl}-acetamide obtained in Step I as described above (450 mg; 0.86 mmol; 1 eq), is dissolved in anhydrous THF (45 ml). The reaction mixture is cooled down to −70° C. and put under nitrogen. n-Butyllithium (3.4 ml; 1.6 M; 6.86 mmol; 8 eq) is added dropwise. The reaction is stirred 1 hour and it is quenched with water. Solvents are evaporated and the resulting crude product is purified by preparative HPLC, affording Compound (37) as a white-off solid (74.1 mg; 15%).

$^1$H NMR (DMSO-$d_6$, 300 MHz) δ 2.13 (s, 3H), 2.37 (s, 3H), 2.62 (d, J=9 Hz, 1H), 2.90 (d, J=12 Hz, 1H), 3.17 (dd, J=9 Hz, 1H), 3.31 (t, 1H), 3.35 (d, 1H), 3.46 (d, 1H), 4.06 (t, J=6 Hz, 1H), 4.45 (s, 1H), 5.57 (s, 1H), 7.70 (s, 1H), 8.05 (s, 1H), 12.17 (s, 1H). M$^-$ (ESI): 444.3; M$^+$ (ESI): 446.3. HPLC (method A), Rt: 2.47 min (purity: 97.7%).

Example 38

N-[5-(5-{[(2-hydroxyethyl)amino]sulfonyl}-3-thienyl)-4-methyl-1,3-thiazol-2-yl]acetamide (38)

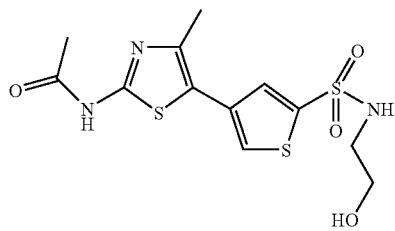

(38)

Step I: N-{5-[2-Bromo-5-(2-hydroxy-ethylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (1900 mg; 4.57 mmol; 1 eq), is dissolved in anhydrous DCM (180 ml). The reaction is put under nitrogen. Triethylamine (3.2 ml; 22.9 mmol; 5 eq) and ethanolamine (1.1 ml; 18.3 mmol; 4 eq) are added successively and the reaction mixture is stirred overnight at room temperature. It is then washed with water, $NH_4Cl$ sat, brine and dried over $MgSO_4$, affording the title compound (1760 mg; 88%).

$^1$H NMR (DMSO-$d_6$, 300 MHz) δ 1.80 (s, 3H), 2 (s, 3H), 2.30 (s, 3H), 2.82 (m, J=21 Hz, 4H), 3.38 (d, J=3 Hz, 4H), 7.15 (d, J=6 Hz, 1H), 7.45 (d, J=3 Hz, 1H), 12.18 (s, 1H). M$^-$ (ESI): 440.1; M$^+$ (ESI): 442.1. HPLC (method A), Rt: 2.61 min (purity: 89.7%).

Step II: N-{5-[5-(2-Hydroxy-ethylsulfamoyl)-thiophen-3-yl]-4-methyl-thiazol-2-yl}-acetamide (38)

N-{5-[2-Bromo-5-(2-hydroxy-ethylsulfamoyl)-thiophen-3-yl]-4-methyl-thiazol-2-yl}-acetamide obtained in Step I as described above (1760 mg; 4 mmol; 1 eq), is dissolved in anhydrous THF (100 ml). The reaction mixture is then cooled down to −70° C. and put under nitrogen. n-Butyllithium (48 ml; 1.6 M; 95.9 mmol; 24 eq) is added dropwise. The reaction is stirred 2 hours at −70° C. and quenched with water. Solvents are evaporated and the resulting residue is purified by preparative HPLC, affording Compound (38) as a white solid (135 mg; 9%).

$^1$H NMR (DMSO-$d_6$, 300 MHz) δ 2.13 (s, 3H), 2.37 (s, 3H), 2.88-2.94 (q, J=6 Hz, 2H), 3.39-3.43 (t, J=6 Hz, 2H), 7.67 (s, 1H), 7.89-7.93 (t, J=3 Hz, 2H), 12.16 (s, 1H). M$^-$ (ESI): 360.1; M$^+$ (ESI): 362.2. HPLC (method A), Rt: 2.06 min (purity: 99.7%).

Example 39

N-(5-{5-[(4-hydroxypiperidin-1-yl)sulfonyl]-3-thienyl}-4-methyl-1,3-thiazol-2-yl)acetamide (39)

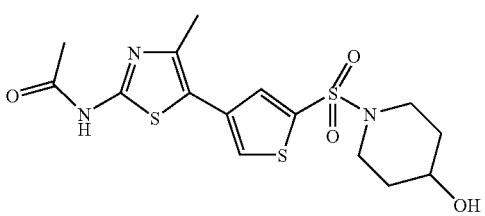

Step I: N-{5-[2-Bromo-5-(4-hydroxy-piperidine-1-sulfonyl)-thiophen-3-yl]4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (3000 mg; 7.22 mmol; 1 eq), is dissolved in anhydrous DCM (400 ml). The reaction is put under nitrogen. Triethylamine (5.0 ml; 36.1 mmol; 5 eq) and 4-hydroxypiperidine (3649.4 mg; 36.1 mmol; 5 eq) are added successively and the reaction mixture is stirred for 6 hours at room temperature. It is washed with water, NaHCO$_3$ sat., brine, and dried over MgSO$_4$, affording the title compound (3500 mg; 88%).

M$^-$ (ESI): 480.2; M$^+$ (ESI): 482.1. HPLC (method A), Rt: 3.09 min (purity: 86.8%).

Step II: N-(5-{5-[(4-hydroxypiperidin-1-yl)sutronyl]-3-thienyl}-methyl-1,3-thiazol-2-yl)acetamide (39)

To N-{5-[2-Bromo-5-(4-hydroxy-piperidine-1-sulfonyl)-thiophen-3-yl]-4-methyl-thiazol-2-yl}-acetamide obtained in Step I as described above (3500 mg; 6.27 mmol; 1 eq), is dissolved in anhydrous TBF (150 ml). The reaction mixture is cooled down to −70° C. and put under nitrogen. n-Butyllithium (18.8 ml; 1.6 M; 37.6 mmol; 6 eq) is added dropwise. The reaction is stirred over weekend and is quenched with water. Solvents are evaporated and the resulting crude product is dissolved in EtOAc, washed with water (2 times), brine and dried over MgSO$_4$. After evaporation of the solvents, the resulting product is suspended in ACN and filtered, affording Compound (39) as a beige solid (830 mg; 32%).

$^1$H NMR (DMSO-d$_6$, 300 MHz) δ 1.46 (m, 2H), 1.75 (m, 2H), 2.13 (s, 3H), 2.37 (s, 3H), 2.85 (m, 2H), 3.20 (m, 2H), 3.59 (m, 1H), 4.72 (d, J=3 Hz, 1H), 7.95 (s, 1H), 8.03 (s, 1H), 12.16 (s, 1H). M$^-$ (ESI): 400.2; M$^+$ (ESI): 402.2. HPLC (method A), Rt: 2.63 min (purity: 97.3%).

Example 40

N-[5-(5-{[(2,3-dihydroxypropyl)amino]sulfonyl}-3-thienyl)-4-methyl-1,3-thiazol-2-yl]acetamide (40)

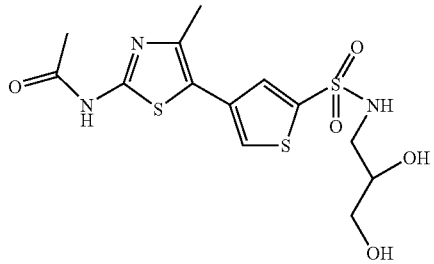

Step I: N-{5-[2-Bromo-5-(2,3-dihydroxy-propylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (500 mg; 1.2 mmol; 1 eq), is dissolved in anhydrous DCM (30 ml). The reaction is put under nitrogen. Triethylamine (0.34 ml; 2.41 mmol; 2 eq) and 2,2-dimethyl-1,3-dioxolane-4-methanamine (0.31 ml; 2.41 mmol; 2 eq) are added successively and the reaction mixture is stirred overnight at room temperature. It is then washed with water, NH$_4$Cl sat., brine and dried over MgSO$_4$, affording the title compound (3650 mg; 94%).

M$^-$ (ESI): 509.57; M$^+$ (ESI):511.2. HPLC (method A), Rt: 3.36 min (purity: 89.2%).

Step II: N-[5-(5-{[(2,3-dihydroxypropyl)amino]sulfonyl}-3-thienyl)-4-methyl-1,3-thiazol-2-yl]acetamide (40)

N-{5-[2-Bromo-5-(2,3-dihydroxy-propylsulfamoyl)-thiophen-3-yl]-4-methyl-thiazol-2-yl}-acetamide obtained in Step I as described above (790 mg; 1.38 mmol; 1 eq), is dissolved in anhydrous THF (50 ml). The reaction mixture is cooled down to −70° C. and put under nitrogen. n-Butyllithium (6.9 ml; 1.6 M; 11.0 mmol; 8 eq) is added dropwise. The reaction is stirred 2 hours and is quenched with water. Solvents are evaporated and the resulting crude product is purified by preparative HPLC, affording Compound (40) as a light pink solid (224 mg; 42%).

$^1$H NMR (DMSO-d$_6$, 300 MHz) δ 2.13 (s, 3H), 2.37 (s, 3H), 2.69-2.77 (m, 1H), 3.24-3.33 (m, 2H), 3.46-3.53 (m, 1H), 7.67 (s, 1H), 7.79-7.83 (t, J=6 Hz, 1H), 7.92 (s, 1H), 12.17 (s, 1H). M$^-$ (ESI): 390.2; M$^+$ (ESI): 392.2. HPLC (method A), Rt: 1.94 min (purity: 100%).

Example 41

N-(4-methyl-5-{5-[(1H-tetrazol-5-ylamino)sulfonyl]-3-thienyl}-1,3-thiazol-2-yl)acetamide (41)

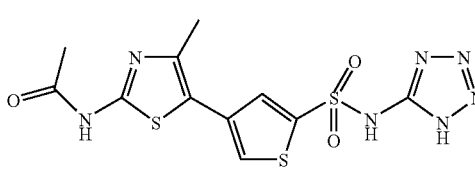

Step I: N-{5-[2-Bromo-5-(1H-tetrazol-5-ylsulfamoyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (500 mg; 1.2 mmol; 1 eq), is dissolved in anhydrous DCM (30 ml). The reaction is put under nitrogen. Triethylamine (0.34 ml; 2.41 mmol; 2 eq) and 5-amino-1H-tetrazole (204.6 mg; 2.41 mmol; 2 eq) are added successively and the reaction mixture is stirred overnight at room temperature. It is then washed with water, NH$_4$Cl sat., brine and dried over MgSO$_4$, affording the title compound (550 mg; 64%).

M$^-$ (ESI): 401.2; M$^+$ (ESI): 403.3. HPLC (method A), Rt: 3.10 min (purity: 65.4%).

Step II: N-(4-methyl-5-{5-[(1H-tetrazol-5-ylamino)sutronyl]-3-thienyl}-1,3-thiazol-2-yl)acetamide (41)

N-{5-[2-Bromo-5-(1H-tetrazol-5-ylsulfamoyl)-thiophen-3-yl]-4-methyl-thiazol-2-yl}-acetamide obtained in Step I as described above (220 mg; 0.37 mmol; 1 eq), is dissolved in anhydrous TBF (20 ml). The reaction mixture is cooled down to −70° C. and put under nitrogen. n-Butyllithium (1.9 ml; 1.6 M; 2.99 mmol; 8 eq) is added dropwise. The reaction is stirred 2 hours and is quenched with water. Solvents are evaporated and the resulting crude product is purified by preparative HPLC, affording Compound (41) as a beige solid (8.5 mg; 6%).

$^1$H NMR (DMSO-d$_6$, 300 MHz) δ 2.13 (s, 1H), 2.35 (s, 3H), 7.39 (s, 1H), 7.70 (s, 1H), 12.13 (s, 1H). HPLC (method A), Rt: 1.87 min (purity: 93.8%).

Example 42

N-{4-methyl-5-[5-(pyrrolidin-1-ylsulfonyl)-3-thienyl]-1,3-thiazol-2-yl}acetamide (42)

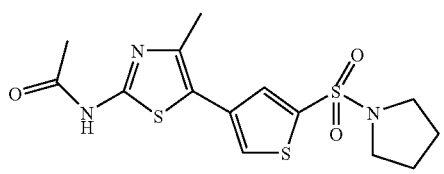

(42)

Step I: N-{5-[2-Bromo-5-(2,5-dihydro-pyrrole-1-sulfonyl)-thiophen-3-yl]-4-methyl-thiazol-2-yl}-acetamide 4-[2-(acetylamino)-4-methyl-1,3-thiazol-5-yl]-5-bromothiophene-2-sulfonyl chloride, prepared as in Step III of Example 23 (500 mg; 1.2 mmol; 1 eq), is dissolved in anhydrous DCM (30 ml). The reaction is put under nitrogen. Triethylamine (0.34 ml; 2.41 mmol; 2 eq) and 3-pyrroline (166.2 mg; 2.41 mmol; 2 eq) are added successively and the reaction mixture is stirred overnight at room temperature. It is then washed with water, NH$_4$Cl sat., brine and dried over MgSO$_4$, affording the title compound (600 mg; 99%).

M$^-$ (ESI): 447.07; M$^+$ (ESI): 449.2. HPLC (method A), Rt: 3.63 min (purity: 88.7%).

Step II: N-{4-methyl-5-[5-(pyrrolidin-1-ylsulfonyl)-3-thienyl]-1,3-thiazol-2-yl}acetamide (42)

N-{5-[2-Bromo-5-(2,5-dihydro-pyrrole-1-sulfonyl)-thiophen-3-yl]-4-methyl-thiazol-2-yl}-acetamide obtained in Step I as described above (612 mg; 1.21 mmol; 1 eq), is dissolved in anhydrous THF (50 ml). The reaction mixture is cooled down to −70° C. and put under nitrogen. n-Butyllithium (15.5 ml; 1.6 M; 9.69 mmol; 8 eq) is added dropwise. The reaction is stirred 2 hours and is quenched with water. The solvents are evaporated and the crude product is purified by preparative HPLC, affording Compound (42) as white-off solid (36 mg; 8%).

$^1$H NMR (DMSO-d$_6$, 300 MHz) δ 1.77-1.82 (m, 4H), 2.23 (s, 3H), 2.46 (s, 3H), 3.30-3.34 (t, J=6 Hz, 4H), 7.84 (s, 1H), 8.11 (s, 1H), 12.26 (s, 1H). M$^-$ (ESI): 370.1; M$^+$ (ESI): 372.1. HPLC (method A), Rt: 3.24 min (purity: 100%).

Example 43

4-methyl-5-{5-[(4-methylpiperazin-1-yl)sulfonyl]-3-thienyl}-1,3-thiazol-2-amine (43)

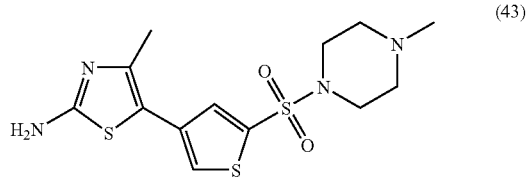

(43)

N-(4-methyl-5-{5-[(4-methylpiperazin-1-yl)sulfonyl]-3-thienyl}-1,3-thiazol-2-yl)acetamide (34) (978.5 mg; 2.44 mmol; 1 eq) is dissolved in hydrochloric acid 1.25 M in EtOH (39.09 ml; 1.25 M; 48.9 mmol; 20 eq). The mixture is stirred overnight at 90° C. It is cooled down to RT, filtrated, affording Compound (43) as a white solid (1084.3 mg; 91%).

$^1$H NMR (DMSO-d$_6$, 300 MHz) δ 2.29 (s, 3H), 2.73 (s, 3H), 2.89 (m, 2H), 3.16 (m, 2H), 3.46 (m, 2H), 3.78 (m, 2H), 7.80 (d, J=1.5 Hz, 1H), 8.18 (d, J=1.5 Hz, 1H), 9.21 (br s, 1H), 11.24 (br s, 1H). HPLC (method A), Rt: 1.11 min (purity: 88.3%). M$^-$ (ESI): 357.17; M$^+$ (ESI): 359.19.

Example 44 methyl 5-[(4-methyl-5-{5-[(4-methylpiperazin-1-yl)sulfonyl]-3-thienyl}-1,3-thiazol-2-yl)amino]-5-oxopentanoate

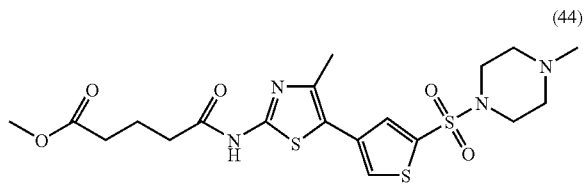

(44)

To a degazed solution of 4-methyl-5-{5-[(4-methylpiperazin-1-yl)sulfonyl]-3-thienyl}-1,3-thiazol-2-amine (43) (53 mg; 0.12 mmol; 1 eq) in anhydrous THF (5 ml), are added N-[(1H-1,2,3-benzotriazol-1-yloxy)(dimethylamino)methylene]-N-methylmethanaminium tetrafluoroborate (59.2 mg;

0.18 mmol; 1.50 eq), mono-methyl glutarate (38.5 μl; 0.31 mmol; 2.50 eq) and N,N-diisopropylethylamine (647 μl; 0.76 M; 0.49 mmol; 4 eq). The reaction mixture is stirred at room temperature for 3 days. The solvents are evaporated and the resulting crude mixture is dissolved in EtOAc. It is washed with NH$_4$Cl sat. solution, water, brine and dried over MgSO$_4$. After evaporation of the solvents, the crude product is purified by flash chromatography (CH$_3$Cl/MeOH gradient from 1/0 to 1/1 over 40 min), affording Compound (44) as white-off solid (21.9 mg; 37%).

$^1$H NMR (DMSO-d$_6$, 300 MHz) δ 2.06 (quint., J=6 Hz, 2H), 2.29 (m, 3H), 2.39 (s, 3H), 2.44 (t, J=6 Hz, 2H), 2.53 (m, 6H), 3.13 (m, 4H), 3.68 (s, 3H), 7.49 (d, J=1.5 Hz, 1H), 7.57 (d, J=1.5 Hz, 1H), 9 (br s, 1H). HPLC (method A), Rt: 2.33 min (purity: 96.0%). M$^-$ (ESI): 485.48; M$^+$ (ESI): 487.38.

Example 45

1-{[4-(2-amino-4-methyl-1,3-thiazol-5-yl)-2-thienyl]sulfonyl}piperidin-4-ol Hydrochloride Salt (45)

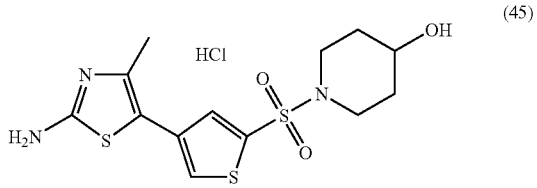

To N-(5-{5-[(4-hydroxypiperidin-1-yl)sulfonyl]-3-thienyl}-4-methyl-1,3-thiazol-2-yl)acetamide (39) (400 mg; 1 mmol; 1 eq) is added hydrochloric acid 1.25 M in EtOH (16 ml; 1.25 M; 19.9 mmol; 20 eq) and the mixture is heated at 90° C. for 8 h30. The reaction mixture is cooled down to RT and a precipitate is formed. It is filtered and washed with cold EtOH, affording the hydrochloride salt of Compound (45) as light yellow powder (328.3 mg; 83%).

$^1$H NMR (DMSO-d$_6$, 300 MHz) δ 1.47 (m, 2H), 1.76 (m, 2H), 2.27 (s, 3H), 2.85 (m, 2H), 3.18 (m, 2H), 3.59 (m, 1H), 7.67 (d, J=1.5 Hz, 1H), 8.07 (s, 1H), 8.96 (br s, 2H). HPLC (method A), Rt: 1.99 min (purity: 98.3%). M$^-$ (ESI): 358.10; M$^+$ (ESI): 360.10.

Example 46

N-{4-methyl-5-[5-(morpholin-4-ylsulfonyl)-3-thienyl]-1,3-thiazol-2-yl}acetamide (46)

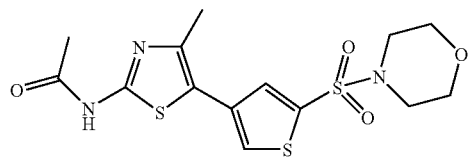

Step I: N-{5-[2-bromo-5-(morpholin-4-ylsulfonyl)-3-thienyl]-4-methyl-1,3-thiazol-2-yl}acetamide 4-[2-(acetylamino)-4-methyl-1,3-thiazol-5-yl]-5-bromothiophene-2-sulfonyl chloride, prepared as in Step III of Example 23 (136 mg; 0.33 mmol; 1 eq), is dissolved in DCM (10 ml). Morpholine (0.25 ml; 1.65 mmol; 5 eq) and DIEA (0.17 ml; 0.98 mmol; 3 eq) are added under a nitrogen atmosphere. After 3 hours, solvents are evaporated. The crude product is dissolved in DCM and washed with NH$_4$Cl saturated solution, water and dried over MgSO$_4$. After evaporation of the solvents, crude material is purified by flash chromatography using cyclohexane/EtOAc (1/1) as eluent, affording the expected compound as an oil (118 mg; 77%).

$^1$H NMR (DMSO-d$_6$, 300 MHz) δ 2.32 (s, 6H), 3.16 (m, 4H), 3.86 (m, 4H), 7.43 (s, 1H), 10.75 (m, 1H). M$^-$ (ESI): 466.1; M$^+$ (ESI): 468.1. HPLC (method A), Rt: 3.39 min (purity: 96%).

Step II: N-{4-methyl-5-[5-(morpholin-4-ylsulfonyl)-3-thienyl]-1,3-thiazol-2-yl}acetamide (46)

N-{5-[2-bromo-5-(morpholin-4-ylsulfonyl)-3-thienyl]-4-methyl-1,3-thiazol-2-yl}acetamide (54 mg; 0.12 mmol; 1 eq) is dissolved in dry THF (5 ml) at −70° C. under an inert atmosphere. n-Butyllithium (0.16 ml; 1.6 M; 0.26 mmol; 2.20 eq) is added slowly and reaction stirred at −70° C. for 25 minutes before being hydrolyzed with water (0.3 ml). Crude material is warmed up to room temperature before being concentrated to dryness. Residue is then taken up with water (2 ml) and EtOAc (10 ml). The organic phases are decanted, dried over MgSO$_4$, filtrated and evaporated. Crude material is purified by flash chromatography on silica gel using cyclohexane/EtOAc (10/90) as eluent, affording expected Compound (46) as an oil (30 mg; 67%).

$^1$H NMR (DMSO-d$_6$, 300 MHz) δ 2.29 (s, 3H), 2.44 (s, 3H), 3.14 (m, 4H), 3.81 (m, 4H), 7.56 (d, J=1.5 Hz, 1H), 7.62 (d, J=1.5 Hz, 1H). M$^-$ (ESI): 386.2; M$^+$ (ESI): 388.2. HPLC (method A), Rt: 3.05 min (purity: 94.4%).

Example 47

N-(5-{2-chloro-5-[(4-methylpiperazin-1-yl)sulfonyl]-3-thienyl}-4-methyl-1,3-thiazol-2-yl)acetamide (47)

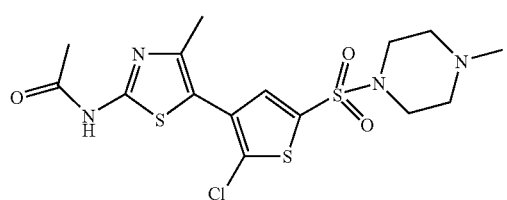

Step I: N-[5-(2-chloro-3-thienyl)-4-methyl-1,3-thiazol-2-yl]acetamide

N-[4-methyl-5-(3-thienyl)-1,3-thiazol-2-yl]acetamide, prepared as in Step I of Example 23 (600 mg; 2.52 mmol; 1 eq) is dissolved in ACN (20 ml) in presence of 100 μl of HClO$_4$ at room temperature. A solution of N-chlorosuccinimide (369.8 mg; 2.77 mmol; 1.10 eq) in ACN (2 ml) is added slowly at room temperature over a period of one hour. Reaction mixture is stirred at room temperature for 1 night before being quenched with water (1 ml). It is then concentrated under vacuo and expected compound extracted with EtOAc, washed with NH$_4$Cl saturated solution, water and dried over MgSO$_4$. After evaporation of the solvents, ACN (5 ml) is added, affording after precipitation, the title compound as a solid (600 mg; 95%).

$^1$H NMR (DMSO-$d_6$, 300 MHz) δ 2.40 (m, 6H), 7.10 (m, 1H), 7.38 (m, 1H). M$^-$ (ESI): 271.1; M$^+$ (ESI): 273.1. HPLC (method A), Rt: 3.56 min (purity: 91.4%).

Step II: N-(5-{2-chloro-5-[(4-methylpiperazin-1-yl)sulfonyl]-3-thienyl}-methyl-1,3-thiazol-2-yl)acetamide (47)

N-[5-(2-chloro-3-thienyl)-4-methyl-1,3-thiazol-2-yl]acetamide (105 mg; 0.38 mmol; 1 eq), prepared in Step I, is sulfonylated according to the procedure used in Step III of Example 23. It is then subsequently reacted with N-methyl piperazine (0.3 ml; 3.8 mmol; 10 eq) as described before in Step III of Example 23. Upon completion of the reaction, solvents are evaporated. The crude product is dissolved in DCM and washed with NH$_4$Cl saturated solution, water and dried over MgSO$_4$. After evaporation of the solvents, expected compound is precipitated using a mixture of DCM/Et$_2$O (1/1), affording Compound (47) as a white solid (65 mg; 35%).

$^1$H NMR (DMSO-$d_6$, 300 MHz) δ 2.16 (s, 3H), 2.25 (s, 3H), 2.78 (s, 3H), 2.97 (m, 2H), 3.01 (m, 2H), 3.18 (m, 2H), 3.48 (m, 2H), 7.83 (s, 1H), 10.93 (m, 1H). M$^-$ (ESI): 433.3; M$^+$ (ESI): 435.3. HPLC (method A), Rt: 2.55 min (purity: 99%).

Example 48

N-(5-{5-[(3-hydroxypiperidin-1-yl)sulfonyl]-3-thienyl}-methyl-1,3-thiazol-2-yl)acetamide (48)

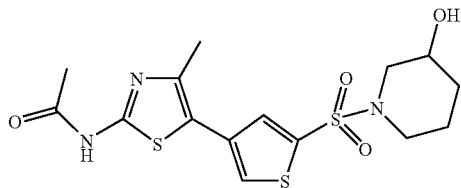

(48)

Step I: N-(5-{2-bromo-5-[(3-hydroxypiperidin-1-yl)sulfonyl]-3-thienyl}-4-methyl-1,3-thiazol-2-yl)acetamide 4-[2-(Acetylamino)-4-methyl-1,3-thiazol-5-yl]-5-bromothiophene-2-sulfonylchloride, prepared as in Step III of Example 23 (136 mg; 0.33 mmol; 1 eq), is dissolved in DCM (10 ml). 3-hydroxy piperidine (0.20 ml; 1.65 mmol; 5 eq) and DIEA (0.17 ml; 0.98 mmol; 3 eq) are added under a nitrogen atmosphere. After 2 hours reaction, solvents are evaporated. The crude product is dissolved in DCM and washed with NH$_4$Cl saturated solution, water and dried over MgSO$_4$. After evaporation of the solvents, crude material is purified by reverse preparative HPLC, affording N-(5-{2-bromo-5-[(3-hydroxypiperidin-1-yl)sulfonyl]-3-thienyl}-4-methyl-1,3-thiazol-2-yl)acetamide as an oil (31 mg; 20%).

$^1$H NMR (DMSO-$d_6$, 300 MHz) δ 1.53 (m, 2H), 1.90 (m, 2H), 2.21 (s, 3H), 2.23 (s, 3H), 2.99 (m, 2H), 3.28 (m, 2H), 3.83 (m, 1H), 7.15 (s, 1H). M$^-$ (ESI): 480.2; M$^+$ (ESI): 482.3. HPLC (method A), Rt: 3.15 min (purity: 97.2%).

Step II: N-(5-{5-[(3-hydroxypiperidin-1-yl)sulfonyl]-3-thienyl}-4-methyl-1,3-thiazol-2-yl)acetamide (48)

N-(5-{2-bromo-5-[(3-hydroxypiperidin-1-yl)sulfonyl]-3-thienyl}-4-methyl-1,3-thiazol-2-yl)acetamide obtained in Step I as described above (54 mg; 0.112 mmol; 1 eq), is dissolved in dry TBF (5 ml) at −70° C. under an inert atmosphere. n-Butyllithium (0.15 ml; 1.6 M; 0.24 mmol; 2.20 eq) is added slowly and reaction stirred at −70° C. for 1 hour before being hydrolyzed with water (0.3 ml). Reaction is warmed up to room temperature before being concentrated to dryness. Residue is taken up with water (2 ml) and EtOAc (10 ml). The organic phases are decanted, dried over MgSO$_4$, filtrated and evaporated. Title compound is purified by reverse preparative HPLC, affording expected Compound (48) as a white solid (20 mg; 43%).

$^1$H NMR (DMSO-$d_6$, 300 MHz) δ 1.48 (m, 1H), 1.71 (m, 1H), 1.89 (m, 2H), 2.48 (s, 3H), 2.51 (s, 3H), 2.82 (m, 1H), 3.93 (m, 1H), 3.29 (m, 1H), 3.45 (m, 1H), 7.50 (d, J=1.5 Hz, 1H), 7.61 (d, J=1.5 Hz, 1H). M$^-$ (ESI): 400.2; M$^+$ (ESI): 402.2. HPLC (method A), Rt: 2.78 min (purity: 99.7%).

Example 49

N-(5-{5-[(allylamino)sulfonyl]-3-thienyl}-4-methyl-1,3-thiazol-2-yl)acetamide (49)

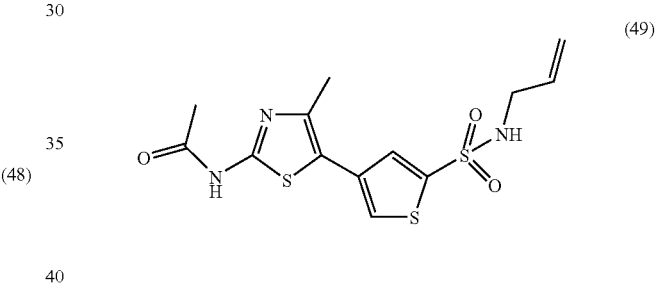

(49)

Step I: N-(5-{5-[(allylamino)sulfonyl]-2-bromo-3-thienyl}-4-methyl-1,3-thiazol-2-yl)acetamide 4-[2-(Acetylamino)-4-methyl-1,3-thiazol-5-yl]-5-bromothiophene-2-sulfonylchloride, prepared as in Step III of Example 23 (100 mg; 0.229 mmol; 1 eq) is dissolved in DCM (10 ml). Allyl amine (0.15 ml; 1.14 mmol; 5 eq) and DIEA (0.17 ml; 0.70 mmol; 3 eq) are added under a nitrogen atmosphere. After 2 hours reaction, solvents are evaporated. The crude product is dissolved in DCM and washed with NH$_4$Cl saturated solution, water and dried over MgSO$_4$. After evaporation of the solvents, crude material is purified by reverse preparative HPLC, affording N-(5-{5-[(allylamino)sulfonyl]-2-bromo-3-thienyl}-4-methyl-1,3-thiazol-2-yl)acetamide as a white solid (35 mg; 35%).

$^1$H NMR (DMSO-$d_6$, 300 MHz) δ 2.15 (s, 3H), 2.20 (s, 3H), 3.51 (t, J=6 Hz, 2H), 4.85 (dd, J=12 Hz and 3 Hz, 1H), 4.97 (dd, J=15 Hz and 3 Hz), 5.51 (dd, J=15 Hz and 12 Hz), 7.55 (s, 1H), 8.25 (m, 1H), 12.22 (m, 1H). M$^-$ (ESI): 436.2; M$^+$ (ESI): 438.2. HPLC (method A), Rt: 3.36 min (purity: 99.9%).

Step II: N-(5-{5-[(allylamino)sulfonyl]-3-thienyl}-4-methyl-1,3-thiazol-2-yl)acetamide (49)

N-(5-{5-[(allylamino)sulfonyl]-2-bromo-3-thienyl}-4-methyl-1,3-thiazol-2-yl)acetamide obtained in Step I as described above (35 mg; 0.08 mmol; 1 eq), is dissolved in dry TBF (5 ml) at −70° C. under an inert atmosphere. n-Butyllithium (0.18 ml; 1 M; 0.18 mmol; 2.20 eq) is added slowly and reaction stirred at −70° C. for 1 hour before being hydrolyzed with water (0.3 ml). Reaction is warmed up to room temperature before being concentrated to dryness. Residue is taken up with water (2 ml) and EtOAc (10 ml). The organic phases are decanted, dried over $MgSO_4$, filtrated and evaporated. Title compound is purified by reverse preparative HPLC, affording Compound (49) as a white powder (3 mg; 10%).

$^1$H NMR (DMSO-$d_6$, 300 MHz) δ 2.36 (s, 3H), 2.47 (s, 3H), 3.76 (m, 2H), 4.72 (t, J=6 Hz, 1H), 5.18 (dd, J=12 Hz and 1 Hz, 1H), 5.25 (dd, J=15 Hz and 1 Hz), 5.81 (dd, J=15 Hz and 12 Hz), 7.37 (d, J=1.5 Hz, 1H), 7.56 (d, J=1.5 Hz, 1H). M$^-$ (ESI): 356.2; M$^+$ (ESI): 358.2. HPLC (method A), Rt: 3.02 min (purity: 98.5%).

Example 50

Biological assays

The compounds of the present invention may be subjected to the following assays:

a) High Throughput PI3K Lipid Kinase Assay (Binding Assay):

The efficacy of compounds of the invention in inhibiting the PI3K induced-lipid phosphorylation may be tested in the following binding assay.

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 μl of the test compound of Formula (I) (solubilized in 6% DMSO; to yield a concentration of 100, 30, 10, 3, 1,0.3, 0.1, 0.03, 0.01, 01 μM of the test compound), the following assay components are added. 1) 5 μl (58 ng) of Human recombinant GST-PI3Kγ (in Hepes 40 mM, pH 7.4, DTT 1 mM and ethylenglycol 5%) 2) 10 μl of lipid micelles and 3) 10 μl of Kinase buffer ([$^{33}$P]γ-ATP 45 μM/60nCi, $MgCl_2$ 30 mM, DTT 1 mM, β-Glycerophosphate 1 mM, $Na_3VO_4$ 100 μM, Na Cholate 0.3%, in Hepes 40 mM, pH 7.4). After incubation at room temperature for 180 minutes, with gentle agitation, the reaction is stopped by addition of 60 μl of a solution containing 100 μg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in Table II below refer to the $IC_{50}$ (μM) with respect to PI3Kγ, i.e. the amount necessary to achieve 50% inhibition of said target. Said values show a considerable inhibitory potency of thiazole compounds with regard to PI3Kγ.

Examples of inhibitory activities for compounds of the invention are set out in Table II below.

TABLE II $IC_{50}$ values of thiazole derivatives against PI3Kγ.

| Example No | PI3Kγ $IC_{50}$ (μM) |
|---|---|
| 1 | 0.119 |
| 2 | 0.396 |
| 4 | 0.298 |
| 5 | 0.020 |
| 7 | 1.195 |
| 8 | 0.170 |
| 9 | 0.158 |
| 10 | 0.289 |
| 11 | 0.200 |
| 12 | 0.522 |
| 13 | 0.109 |
| 14 | 0.198 |
| 15 | 0.070 |
| 16 | 0.373 |
| 17 | 0.071 |
| 18 | 0.105 |
| 23 | 0.028 |
| 24 | 0.016 |
| 26 | 0.067 |
| 28 | 0.078 |
| 29 | 0.028 |
| 39 | 0.014 |
| 46 | 0.027 | b) Cell Based ELISA to Monitor PI3K Inhibition:

The efficacy of compounds of the invention in inhibiting the PI3K induced Akt/PKB phosphorylation may be tested in the following cell based assay.

Measurement of Akt/PKB phosphorylation in macrophages after stimulation with Complement 5a: Raw 264: Raw 264-7 macrophages (cultured in DMEM-F12 medium containing 10% Fetal Calf serum and antibiotics) are plated at 20'000 cells/well in a 96 MTP 24 h before cell stimulation. Prior to the stimulation with 50 mM of Complement 5a during 5 minutes, Cells are serum starved for 2 h, and pretreated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% $H_2O_2$ and 0.1% Sodium Azide in PBS/Triton and washed 3 times in PBS/Triton. Cells are then blocked by 60 minutes incubation with 10% fetal calf serum in PBS/Triton. Next, phosphorylated Akt/PKB is detected by an overnight incubation at 4° C. with primary antibody (anti phospho Serine 473 Akt IHC, Cell Signaling) diluted 800-fold in PBS/Triton, containing 5% bovine serum albumin (BSA). After 3 washes in PBS/Triton, cells are incubated for 60 minutes with a peroxidase conjugated goat-anti-rabbit secondary antibody (1/400 dilution in PBS/Triton, containing 5% BSA), washed 3 times in PBS/Triton, and 2 times in PBS and further incubated in 100 μl of luminescent substrate reagent solution (Pierce) for 2 minutes, followed by the reading (1 s/well).

The values indicated in Table III below reflect the percentage of inhibition of AKT phoshorylation as compared to basal level. Said values show a clear effect of the thiazole compounds on the activation of AKT phosphorylation in macrophages.

Examples of inhibitory activities for compounds of the invention are set out in Table III below.

TABLE III

IC$_{50}$ values of thiazole derivatives in Cell Assay

| Example No | Cell Assay (P-Akt, Elisa) IC$_{50}$ [µM] |
|---|---|
| 1 | 0.66 |
| 9 | 0.85 |
| 10 | 1.29 |
| 23 | 0.48 |
| 29 | 0.46 |
| 39 | 0.05 |
| 39 (re-testing) | 0.32 |
| 46 | >30 |
| 48 | 0.15 |

Example 51

Thioglycollate-Induced Peritoneal Cavity Cell Recruitment Model

The in vivo efficacy of compounds of the invention in inhibiting the migration of leukocytes upon intraperitoneal challenge of thioglycollate may be tested with the following assay.

Experimental Protocol:

8-10 weeks old female C3H mice are fasted during 18 hours. 15 minutes prior the intraperitoneal injection of thioglycollate (1.5%, 40 ml/kg), the mice are treated orally with Thiazoles of Formula (I). Control mice receive CMC/Tween as vehicle (10 ml/kg). The mice are then sacrificed by CO$_2$ inhalation and the peritoneal cavity is washed two times with 5 ml of ice-cold PBS/1 mM EDTA. The lavages are done 4 hours or 48 hours after thioglycollate challenge to evaluate neutrophils or macrophages recruitment, respectively. The white blood cells (neutrophils, lymphocytes or macrophages) are counted using a Beckman Coulter® A$^C$T 5 Diff™. Dexamethasone is used as reference drug.

Examples of inhibitory activities of for compounds of the invention are set out in the Table IV and Table V below.

TABLE IV

| Compound N. | [% inhibition of Neutrophil recruitment] at 10 mg/kg after 4 h |
|---|---|
| 9 | 48 |
| 10 | 58 |
| 29 | 28 |
| 39 | 48 |
| 46 | 36 |

TABLE V

| Compound N. | [% inhibition of Macrophage recruitment] at 10 mg/kg after 48 h |
|---|---|
| 39 | 43 |

Example 52

K/B×N Serum Transfer Model of Arthritis in Mice

Experimental Protocol

Mouse: Balb/c (Charles River) (8 weeks) received by iv route 150 µl of K/B×N serum, containing high level of auto-antibodies against glucose-6-phosphate isomerase. They evolved severe arthritis assessed with a clinical score (0-12) evaluating the presence of swelling, erythema, edema, joint rigidity and ankylosis. Compound 39 was orally administered twice a day as a suspension in 10 ml/kg CMC/Tween at the doses indicated in FIG. 1, starting from day 3. Results are expressed in terms of mean values of area under curve (AUC) all over the experimental period and the values are calculated as variations compared to the initial time point (day 1).

The final score was the sum of scores on individual paws. The swelling of ankle, fore paw and hind paw was measure using a celliper. The clinical score and the swelling were determined every day. At the end of experiment the legs were removed and fixed in formalin for X ray radiology and histology.

Examples 53

Collagen-Induced Arthritis, CIA (Mouse)

Experimental Protocol

Figure 2:
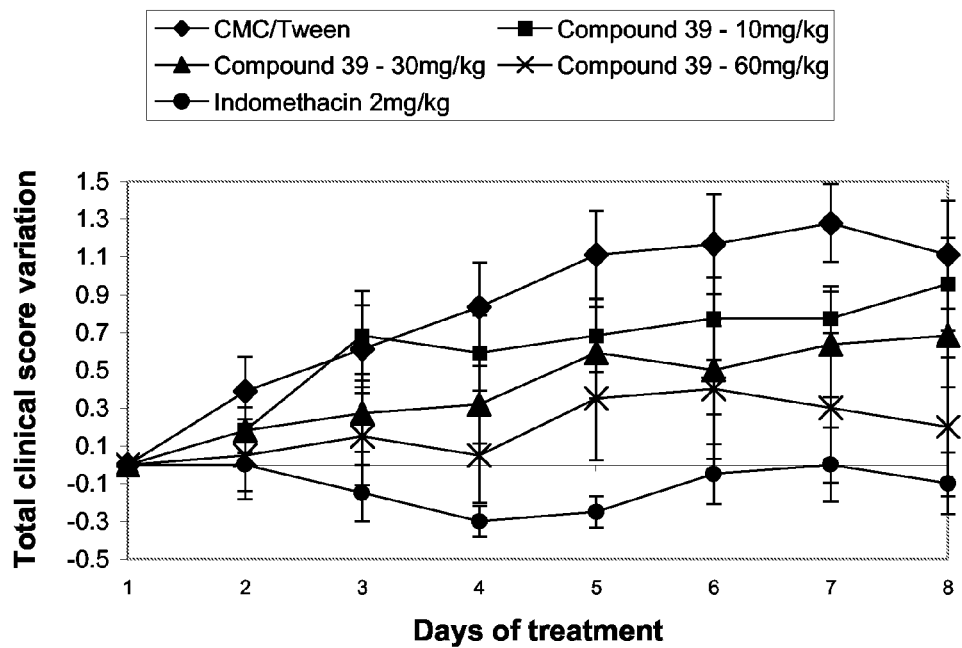
FIG. 2: Collagen-induced arthritis (mouse) after treatment with compound 39 Shows 39 shows the clinical score variation.

Male DBA/1 mice from the Japanese Charles River colony (widely accepted as an experimental model, the selected strain has documented susceptibility to CIA) are immunized on day 0 by injecting intradermally at the base of the tail 0.2 ml of an emulsion composed of 100 µg bovine type II collagen (Norwell Diagnostics, Zurich, Switzerland) in Complete Freund's Adjuvant (CFA, Difco, Detroit, U.S.A.) containing 0.4 mg of *Mycobacterium tuberculosis*. This procedure results, starting approximately at days 18-20, in the appearance of signs of inflammation affecting one or more limbs. Starting from day 19, the animals are individually graded for disease severity by means of a clinical score composed of number of inflamed fingers score (up to 2 in total) and the paw thickness score (up to 3 for each paw). Paw swelling of the first arthritic paw (the one that allowed clinical recruitment being the most involved one) is daily measured as well and considered as an index of disease progression. The treatment with compounds or vehicle starts for each animal at a total clinical score of ≧1.5 (curative treatment) and is continued for 7 consecutive days (8-10 animals per treatment group). Samples for histological analysis are taken at the end of the 7-day treatment periods. All animals are sacrificed 2 hours after the last treatment. Compound 39 was orally administered twice a day as a suspension in 10 ml/kg CMC/Tween at the doses indicated in FIG. 2. Results are expressed in terms of mean values of area under curve (AUC) all over the experimental period and the values are calculated as variations compared to the initial time point (day 1).

Table VI below shows reduction of clinical score in Collagen induced arthritis for Compound 39

TABLE VI

| Dose [mg/kg orally] | Reduction of total clinical score [%] |
|---|---|
| 10 | 30 |
| 30 | 50 |
| 60 | 75 |

Example 54

Preparation of a Pharmaceutical Formulation

Formulation 1

Tablets

A compound of Formula (I) is admixed as a dry powder with a dry gelatin binder in an approximate 1:2 weight ration. A minor amount of magnesium stearate is added as a lubricant. The mixture is formed into 240-270 mg tablets (80-90 mg) of active thiazole compound per tablet) in a tablet press.

Formulation 2

Capsules

A compound of Formula (I) is admixed as a dry powder with a starch diluent in an approximate 1:1 weight ratio. The mixture is filled into 250 mg capsules (125 mg of active thiazole compound per capsule).

Formulation 3

Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4

Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active thiazole compound) in a tablet press.

Formulation 5

Injection

A compound of Formula (I) is dissolved in a buffered sterile saline injectable aqueous medium to a concentration of approximately 5 mg/ml.

The invention claimed is:

1. A thiazole derivative according to Formula (I),

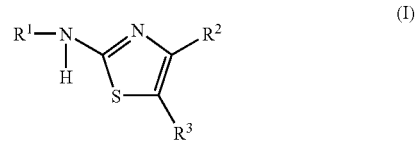

wherein:
$R^1$ is selected from H, acyl, or a substituted acyl;
$R^2$ is a $C_1$-$C_6$-alkyl, or substituted $C_1$-$C_6$-alkyl;
$R^3$ is selected from the following thienyl groups, defined as T1 and T2:

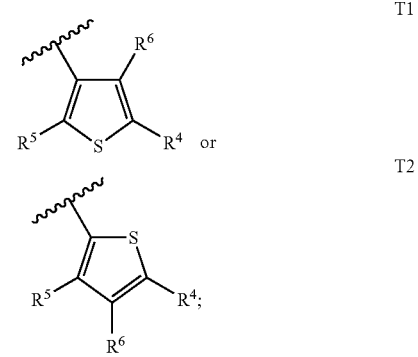

wherein:
$R^4$ is selected from:
a sulfonyl group $SO_2$—R, wherein R is selected from heteroaryl or heterocycloalkyl; and
$R^5$ and $R^6$ are independently selected from H, $C_1$-$C_6$-alkyl, $C_2$-$C_6$-alkenyl, $C_2$-$C_6$-alkynyl groups; a substituted $C_1$-$C_6$-alkyl, substituted $C_2$-$C_6$-alkenyl, substituted $C_2$-$C_6$-alkynyl groups or halogen;
and isomers, enantiomers, diastereomers, racemates or pharmaceutically acceptable salts thereof.

2. The thiazole derivative according to claim 1, wherein $R^1$ is acetyl.

3. The thiazole derivative according to claim 1, wherein $R^2$ is methyl.

4. The thiazole derivative according to claim 1, wherein $R^3$ is the thienyl group T1.

5. The thiazole derivative according to claim 1, wherein $R^3$ is the thienyl group T2.

6. The thiazole derivative according to claim 1, wherein $R^4$ is a $SO_2$—R and R is heteroaryl.

7. The thiazole derivative according to claim 1, wherein $R^4$ is $SO_2$—R and R is heterocycloalkyl.

8. The thiazole derivative according to claim 1, wherein $R^5$ and $R^6$ are H.

9. The thiazole derivative according to claim 1, said thiazole compound being selected from the following compounds:
N-(4-methyl-5-{5-[(prop-2-yn-1-ylamino)sulfonyl]-2-thienyl}-1,3-thiazol-2-yl)acetamide;
N-(5-{5-[(4-acetylpiperazin-1-yl)sulfonyl]-2-thienyl}-4-methyl-1,3-thiazol-2-yl)acetamide;
N-{5-[5-({2-(dimethylamino)ethyl]amino}sulfonyl)-2-thienyl]-4-methyl-1,3-thiazol-2-yl}acetamide;
N-[4-methyl-5-(5-{[(1-methylpiperidin-4-yl)amino]sulfonyl}-2-thienyl)-1,3-thiazol-2-yl]acetamide;

N-[5-(5-{[[2-(dimethylamino)ethyl](methyl)amino]sulfonyl}-2-thienyl)-4-methyl-1,3-thiazol-2-yl]acetamide;
5-(2-amino-4-methyl-1,3-thiazol-5-yl)-N-(2-morpholin-4-ylethyl)thiophene-2-sulfonamide;
methyl5-[4-methyl-5-(5-[(2-morpholin-4-ylethyl)amino]sulfonyl}-2-thienyl)-1,3-thiazol-2-yl]amino}-5-oxopentanoate;
N-(4-methyl-5-{5-[(4-methylpiperazin-1-yl)sulfonyl]-2-thienyl}-1,3-thiazol-2-yl)acetamide;
N-[4-methyl-5-(5-{[(2-morpholin-4-ylethyl)amino]sulfonyl}-2-thienyl)-1,3-thiazol-2-yl]acetamide;
N-{5-[5-({[3-(dimethylamino)propyl]amino}sulfonyl)-2-thienyl]-4-methyl-1,3-thiazol-2-yl}acetamide;
N-{4-methyl-5-[5-(piperazin-1-ylsulfonyl)-2-thienyl]-1,3-thiazol-2-yl}acetamide;
N2-({5-[2-(acetylamino)-4-methyl-1,3-thiazol-5-yl]-2-thienyl}sulfonyl)-N~1~-methylglycinamide;
N-{5-[5-({[2-(acetylamino)ethyl]amino}sulfonyl)-2-thienyl]-4-methyl-1,3-thiazol-2-yl]acetamide;
N-{5-[5-({[(2,2-dimethyl-1,3-dioxolan-4-yl)methyl]amino}sulfonyl)-2-thienyl]-4-methyl-1,3-thiazol-2-yl}acetamide;
methylN-({5-[2-(acetylamino)-4-methyl-1,3-thiazol-5-yl]-2-thienyl}sulfonyl)serinate;
N-({5-[2-(acetylamino)-4-methyl-1,3-thiazol-5-yl]-2-thienyl}sulfonyl)serine;
N-[5-(5-{[(2,3-dihydroxypropyl)amino]sulfonyl}-2-thienyl)-4-methyl-1,3-thiazol-2-yl]acetamide;
N-(5-{5-[(dimethylamino)sulfonyl]-2-thienyl}-4-methyl-1,3-thiazol-2-yl)acetamide;
N-{4-methyl-5-[5-({-methyl[2-(methylamino)ethyl]amino}sulfonyl)-2-thienyl]-1,3-thiazol-2-yl]acetamide;
N-[5-(5-{[[2-(diethylamino)ethyl](methyl)amino]sulfonyl}-2-thienyl)-4-methyl-1,3-thiazol-2-yl]acetamide;
N-[5-(5-{[(2-methoxyethyl)(methyl)amino]sulfonyl}-2-thienyl)-4-methyl-1,3-thiazol-2-yl]acetamide;
N-[5-(5-{[[2-(dimethylamino)ethyl](ethyl)amino]sulfonyl}-2-thienyl)-4-methyl-1,3-thiazol-2-yl]acetamide;
N-{5-[5-({[2-(dimethylamino)ethyl]amino}sulfonyl)-3-thienyl]-4-methyl-1,3-thiazol}-2-yl}acetamide;
N-[4-methyl-5-(5-{[(2-morpholin-4-ylethyl)amino]sulfonyl}-3-thienyl)-1,3-thiazol-2-yl]acetamide;
N-[4-methyl-5-(5-{[(2-piperidin-1-ylethyl)amino]sulfonyl}-3-thienyl)-1,3-thiazol-2-yl]acetamide;
N-{4-methyl-5-[5-(piperazin-1-ylsulfonyl)-3-thienyl]-1,3-thiazol-2-yl}acetamide;
N-{5-[5-({[3-(dimethylamino)propyl]amino 1 sulfonyl)-3-thienyl]-4-methyl-1,3-thiazol-2-yl}acetamide;
N-[4-methyl-5-(5-{[(1-methylpiperidin-4-yl)amino]sulfonyl}-3-thienyl)-1,3-thiazol-2-yl]acetamide;
N-(4-methyl-5-{5-[(4-methylpiperazin-1-yl)sulfonyl]-3-thienyl}-1,3-thiazol-2-yl)acetamide;
tert-butyl[1-({4-[2-(acetylamino)-4-methyl-1,3-thiazol-5-yl]-2 thienyl}sulfonyl)piperidin-4-yl]methylcarbamate;
N-(5-{5-[(3-hydroxypyrrolidin-1-yl)sulfonyl]-3-thienyl}-4-methyl-1,3-thiazol-2-yl)acetamide;
N-[5-(5-{[(3-hydroxypropyl)amino]sulfonyl}-3-thienyl)-4-methyl-1,3-thiazol-2-yl]acetamide;
N-[5-(5-{[(cis-4-hydroxycyclohexyl)amino]sulfonyl}-3-thienyl)-4-methyl-1,3-thiazol-2-yl]acetamide;
N-(5-{5-[(4-methoxypiperidin-1-yl)sulfonyl]-3-thienyl}-4-methyl-1,3-thiazol-2-yl)acetamide;
N-[4-methyl-5-(5-{[4-(methylamino)piperidin-1-yl]sulfonyl}-3-thienyl)-1,3-thiazol-2-yl]acetamide;
N-[5-(5-{[[2-(dimethylamino)ethyl](methyl)amino]sulfonyl}-3-thienyl)-4-methyl-1,3-thiazol-2-yl]acetamide;
N-[5-(5-{[(1S,5S,7S)-7-(hydroxymethyl)-6,8-dioxa-3-azabicyclo[3.2.1]oct-3-yl]sulfonyl}-3-thienyl)-4-methyl-1,3-thiazol-2-yl]acetamide;
N-[5-(5-{[(2-hydroxyethyl)amino]sulfonyl}-3-thienyl)-4-methyl-1,3-thiazol-2-yl]acetamide;
N-(5-{5-[(4-hydroxypiperidin-1-yl)sulfonyl]-3-thienyl}-4-methyl-1,3-thiazol-2-yl)acetamide;
N-[5-(5-{[(2,3-dihydroxypropyl)amino]sulfonyl}-3-thienyl)-4-methyl-1,3-thiazol-2-yl]acetamide;
N-(4-methyl-5-{5-[(1H-tetrazol-5-ylamino)sulfonyl]-3-thienyl}-1,3-thiazol-2-yl)acetamide;
N-{4-methyl-5-[5-(pyrrolidin-1-ylsulfonyl)-3-thienyl]-1,3-thiazol-2-yl}acetamide;
4-methyl-5-{5-[(4-methylpiperazin-1-yl)sulfonyl]-3-thienyl}-1,3-thiazol-2-amine;
methyl 5-[(4-methyl-5-{5-[(4-methylpiperazin-1-yl)sulfonyl]-3-thienyl}-1,3-thiazol-2-yl)amino}-5-oxopentanoate;
1-{[4-(2-amino-4-methyl-1,3-thiazol-5-yl)-2-thienyl]sulfonyl}piperidin-4-ol;
N-4-methyl-5-[5-methyl-(morpholin-4-ylsulfonyl)-3-thienyl]-1,3-thiazol-2-yl)acetamide;
N-(5-{2-chloro-5-[(4-methylpiperazin-1-yl)sulfonyl]-3-thienyl}-4-methyl-1,3-thiazol-2-yl)acetamide;
N-(5-{5-[(3-hydroxypiperidin-1-yl)sulfonyl]-3-thienyl}-4-methyl-1,3-thiazol-2-yl)acetamide;
N-(5-{5-[(allylamino)sulfonyl]-3-thienyl}-4-methyl-1,3-thiazol-2-yl)acetamide.

10. A pharmaceutical composition comprising a compound according to claim 1 and a pharmaceutically acceptable carrier, diluent or excipient thereof.

* * * * *

UNITED STATES PATENT AND TRADEMARK OFFICE
CERTIFICATE OF CORRECTION

PATENT NO. : 7,879,888 B2
APPLICATION NO. : 11/915521
DATED : February 1, 2011
INVENTOR(S) : Anna Quattropani et al.

It is certified that error appears in the above-identified patent and that said Letters Patent is hereby corrected as shown below:

Column 3,
Line 67, "PI3Ky)" should read --PI3Kγ)--.

Column 7,
Lines 45-46, "pancreatitis, multi or; multi-organ" should read --pancreatitis, multi-organ--.

Column 18,
Line 21, "pepper-mint" should read --peppermint--.
Line 40, "Pharma-ceutical" should read --Pharmaceutical--.
Lines 48-49, "pathways for the will be described" should read --pathways will be described--.

Column 20,
Line 11, "SchemE 1" should read --Scheme 1--.

Column 22,
Line 47, "X=50 Br, I" should read --X = Br, I--.

Column 29,
Line 66, "$M^+$ (ES): 239.01" should read --$M^+$ (ESI): 239.01--.

Column 30,
Line 17, "M"(ESI): 335.08" should read --$M^-$ (ESI): 335.08--.
Line 21, "sutronyl]" should read --sulfonyl]--.
Line 34, "(ES): 354.2" should read --(ESI): 354.2--.

Signed and Sealed this
Seventh Day of June, 2011

David J. Kappos
*Director of the United States Patent and Trademark Office*

Column 31,
Line 62,

" [chemical structure] " should read -- [chemical structure] --.

Column 38,
Line 33, "TBF (2 ml) should read --THF (2 ml)--.

Column 41,
Lines 41-42, "Trifluoroacetic Salt" should read --trifluoroacetic salt--.

Column 43,
Line 11, "Trifluoroacetic Salt" should read --trifluoroacetic salt--.
Lines 51-52, "ethylsutramoyl)" should read --ethylsulfamoyl)--.

Column 44,
Line 6, "thiophen-2-yl]" should read --thiophen-3-yl]--.
Line 8, "TBF (12 ml)" should read --THF (12 ml)--.

Column 45,
Line 61, "TBF (50 ml)" should read --THF (50 ml)--.

Column 46,
Line 56, "TBF (50 ml)" should read --THF (50 ml)--.

Column 47,
Line 51, "TBF (50 ml)" should read --THF (50 ml)--.

Column 48,
Line 53, "TBF (50 ml)" should read --THF (50 ml)--.

Column 50,
Lines 48-49, "sutronyl" should read --sulfonyl--.

Column 51,
Line 40, "TBF (20 ml)" should read --THF (20 ml)--.

Column 52,
Line 34, "TBF (10 ml)" should read --THF (10 ml)--.

Column 53,
Line 2, "sutronyl" should read --sulfonyl--.
Lines 18-19, "sutronyl" should read --sulfonyl--.
Line 25, "TBF (20 ml)" should read --THF (20 ml)--.

Column 57,
Lines 46-47, "sutronyl" should read --sulfonyl--.
Line 53, "TBF (150 ml)" should read --THF (150 ml)--.

Column 59,
Line 19, "sutronyl" should read --sulfonyl--.
Line 25, "TBF (20 ml)" should read --THF (20 ml)--.

Column 64,
Line 8, "TBF (5 ml)" should read --THF (5 ml)--.

Column 65,
Line 2, "TBF (5 ml)" should read --THF (5 ml)--.

Column 68,
Line 24, "celliper" should read --calliper--.
Line 44, "(Norwell" should read --(Morwell--.

Column 70,
Line 64, "N-{5-[5-([2-" should read --N-{5-[5-({[2--.

Column 71,
Line 6, "methyl5-[4-methyl-5-(5-{[2-morpholin" should read
    --methyl5-{[4-methyl-5-(5-{[2-morpholin--.
Line 17, "N2-({5-[2" should read --N~2~-({5-[2--.
Line 43, "1,3-thiazol}-2-yl}" should read --1,3-thiazol-2-yl}--.
Line 50, "amino 1 sulfonyl)" should read --amino} sulfonyl)--.

Column 72,
Line 36, "3-thienyl]" should read --3-thienyl}--.
Line 40, "N-4-methyl" should read --N-{4-methyl--.
Line 41, "thiazol-2-yl)acetamide" should read --thiazol-2-yl}acetamide--.
Line 45, "4-methyl-1,3-thiazol-2-yl)acetamide;" should read
    --4-methyl-1,3-thiazol-2-yl)acetamide; or--.